US012691030B2

(12) United States Patent
Kaufman et al.

(10) Patent No.: US 12,691,030 B2
(45) Date of Patent: Jul. 28, 2026

(54) SYSTEMS AND METHODS OF SYNCHRONIZING CHEST COMPRESSIONS WITH MYOCARDIAL ACTIVITY

(71) Applicant: ZOLL Medical Corporation, Chelmsford, MA (US)

(72) Inventors: Christopher L Kaufman, Somerville, MA (US); Gary A Freeman, Waltham, MA (US); Naveed Zaidi, Shrewsbury, MA (US); Joshua W Lampe, Groton, MA (US); Annemarie E Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 549 days.

(21) Appl. No.: 16/431,884

(22) Filed: Jun. 5, 2019

(65) Prior Publication Data

US 2019/0374428 A1     Dec. 12, 2019

Related U.S. Application Data

(60) Provisional application No. 62/682,070, filed on Jun. 7, 2018, provisional application No. 62/681,287, filed on Jun. 6, 2018.

(51) Int. Cl.
*A61H 31/00*     (2006.01)
*A61B 5/33*     (2021.01)
(Continued)

(52) U.S. Cl.
CPC ............. *A61H 31/005* (2013.01); *A61B 5/33* (2021.01); *A61B 5/349* (2021.01); *A61B 5/352* (2021.01);
(Continued)

(58) Field of Classification Search
CPC .... A61H 31/00; A61H 31/004; A61H 31/006; A61H 31/007
See application file for complete search history.

(56) References Cited

U.S. PATENT DOCUMENTS 4,393,877 A * 7/1983 Imran .................. A61N 1/3956
                                                                600/518
4,928,674 A 5/1990 Halperin et al.
(Continued)

FOREIGN PATENT DOCUMENTS

WO     WO-2004066901 A1 * 8/2004 ............. A61H 31/00
WO         2016201367       12/2016

OTHER PUBLICATIONS

Pan, Jiapu and Willis J. Tompkins, "A Real-Time QRS Detection Algorithm." IEEE Transactions on Biomedical Engineering, vol. BME-32, No. 3 (Mar. 1985): 230-36; (Year: 1985).*
(Continued)

*Primary Examiner* — Timothy A Stanis
*Assistant Examiner* — Christopher E Miller
(74) *Attorney, Agent, or Firm* — ZOLL Medical Corporation

(57) ABSTRACT

Systems and method for providing chest compressions to a patient during cardiopulmonary resuscitation may include at least one ECG sensor configured to obtain ECG signals, an automated chest compressor configured to provide chest compressions and at least one processor, memory and associated circuitry of a medical device communicatively coupled with the at least one ECG sensor and the automated chest compressor. The at least one processor may be configured to receive and analyze the ECG signals, determine, based on the analysis, whether the patient is in a condition of unconscious hypotension with organized ECG, analyze, in response to a determination that the patient is in the condition of unconscious hypotension with organized ECG, (Continued)

the received ECG signals to detect a QRS complex, and generate an output to apply a chest compression at a pre-determined time relative to the detected QRS complex.

44 Claims, 18 Drawing Sheets

(51) Int. Cl.
   *A61B 5/349* (2021.01)
   *A61B 5/352* (2021.01)
(52) U.S. Cl.
   CPC ... *A61H 31/006* (2013.01); *A61H 2201/5043* (2013.01); *A61H 2201/5048* (2013.01); *A61H 2230/04* (2013.01); *A61H 2230/207* (2013.01); *A61H 2230/25* (2013.01); *A61H 2230/30* (2013.01); *A61H 2230/65* (2013.01)

(56) References Cited

U.S. PATENT DOCUMENTS

| 5,020,516 | A | | 6/1991 | Biondi et al. | |
|---|---|---|---|---|---|
| 5,117,824 | A | * | 6/1992 | Keimel | A61N 1/3621 |
| | | | | | 607/4 |
| 5,490,820 | A | | 2/1996 | Schock et al. | |
| 5,496,257 | A | | 3/1996 | Kelly | |
| 5,496,351 | A | | 3/1996 | Plicchi et al. | |
| 5,514,079 | A | * | 5/1996 | Dillon | A61H 31/00 |
| | | | | | 601/151 |
| 5,697,378 | A | * | 12/1997 | Elghazzawi | A61B 5/7203 |
| | | | | | 128/901 |
| 5,709,215 | A | * | 1/1998 | Perttu | A61B 5/352 |
| | | | | | 600/521 |
| 5,772,613 | A | * | 6/1998 | Gelfand | A61H 31/00 |
| | | | | | 601/1 |
| 6,053,869 | A | | 4/2000 | Kawagishi et al. | |
| 6,070,097 | A | * | 5/2000 | Kreger | A61B 5/055 |
| | | | | | 600/521 |
| 6,179,793 | B1 | * | 1/2001 | Rothman | A61H 9/0078 |
| | | | | | 600/17 |
| 6,234,985 | B1 | | 5/2001 | Lurie et al. | |
| 6,298,267 | B1 | | 10/2001 | Rosborough et al. | |
| 6,351,671 | B1 | | 2/2002 | Myklebust et al. | |
| 6,480,733 | B1 | | 11/2002 | Turcott | |
| 6,620,116 | B2 | | 9/2003 | Lewis | |
| 6,752,771 | B2 | | 6/2004 | Rothman et al. | |
| 7,011,637 | B2 | | 3/2006 | Sherman et al. | |
| 7,220,235 | B2 | | 5/2007 | Geheb et al. | |
| 7,226,427 | B2 | | 6/2007 | Steen | |
| 7,270,639 | B2 | | 9/2007 | Jensen et al. | |
| 7,565,194 | B2 | | 7/2009 | Tan et al. | |
| 7,645,247 | B2 | | 1/2010 | Paradis | |
| 7,650,181 | B2 | | 1/2010 | Freeman et al. | |
| 7,805,203 | B2 | | 9/2010 | Ben-David et al. | |
| 8,219,210 | B2 | | 7/2012 | Arcot-Krishnamurthy et al. | |
| 8,527,043 | B2 | | 9/2013 | Dupelle et al. | |
| 8,870,797 | B2 | | 10/2014 | Paradis | |
| 8,942,800 | B2 | | 1/2015 | Thiagrajan et al. | |
| 9,126,055 | B2 | | 9/2015 | Abdeen et al. | |
| 9,259,543 | B2 | | 2/2016 | Paradis et al. | |
| 9,833,378 | B2 | | 12/2017 | Paradis et al. | |
| 10,159,811 | B2 | | 12/2018 | Silver et al. | |
| 2002/0069878 | A1 | * | 6/2002 | Lurie | A61M 16/022 |
| | | | | | 128/204.18 |
| 2003/0060723 | A1 | | 3/2003 | Joo et al. | |
| 2004/0116969 | A1 | | 6/2004 | Owen et al. | |
| 2006/0100556 | A1 | | 5/2006 | Hargens et al. | |
| 2006/0149157 | A1 | * | 7/2006 | Weil | A61B 5/7207 |
| | | | | | 600/518 |
| 2006/0190045 | A1 | | 8/2006 | Marcus et al. | |
| 2006/0270952 | A1 | | 11/2006 | Freeman et al. | |
| 2007/0161916 | A1 | * | 7/2007 | Zantos | A61M 60/515 |
| | | | | | 600/517 |
| 2008/0140159 | A1 | * | 6/2008 | Bornhoft | A61B 5/0006 |
| | | | | | 607/60 |
| 2008/0215102 | A1 | * | 9/2008 | Myklebust | G09B 23/288 |
| | | | | | 607/6 |
| 2009/0062701 | A1 | * | 3/2009 | Yannopoulos | A61H 31/006 |
| | | | | | 601/41 |
| 2009/0228057 | A1 | * | 9/2009 | Allavatam | A61B 5/0245 |
| | | | | | 607/5 |
| 2010/0319691 | A1 | * | 12/2010 | Lurie | A61M 16/201 |
| | | | | | 128/203.12 |
| 2011/0301513 | A1 | * | 12/2011 | Freeman | A61H 31/006 |
| | | | | | 601/43 |
| 2011/0319780 | A1 | * | 12/2011 | Frank | A61B 5/7239 |
| | | | | | 600/521 |
| 2012/0016179 | A1 | * | 1/2012 | Paradis | A61H 31/005 |
| | | | | | 600/17 |
| 2012/0277599 | A1 | * | 11/2012 | Greenhut | A61B 5/0215 |
| | | | | | 600/485 |
| 2012/0302860 | A1 | * | 11/2012 | Volpe | A61B 5/341 |
| | | | | | 600/512 |
| 2014/0336546 | A1 | * | 11/2014 | Chapman | A61H 31/005 |
| | | | | | 601/41 |
| 2015/0265497 | A1 | * | 9/2015 | Kaufman | A61H 31/006 |
| | | | | | 601/41 |
| 2016/0045117 | A1 | * | 2/2016 | Liu | A61B 5/02405 |
| | | | | | 600/502 |
| 2016/0073919 | A1 | * | 3/2016 | Roessler | A61B 5/0816 |
| | | | | | 600/407 |
| 2016/0317385 | A1 | * | 11/2016 | Salcido | A61H 31/006 |
| 2017/0035650 | A1 | * | 2/2017 | Taylor | A61B 5/113 |
| 2017/0105898 | A1 | * | 4/2017 | Taylor | G06T 7/0012 |
| 2017/0274213 | A1 | * | 9/2017 | Ghosh | A61N 1/0573 |
| 2017/0354827 | A1 | * | 12/2017 | Zhang | A61B 5/363 |
| 2018/0185240 | A1 | * | 7/2018 | Von Schenck | A61H 31/008 |
| 2018/0207437 | A1 | * | 7/2018 | Zhang | A61N 1/3987 |
| 2019/0336025 | A1 | * | 11/2019 | Qu | G16H 40/63 |
| 2019/0336083 | A1 | * | 11/2019 | Gill | A61B 5/361 |

OTHER PUBLICATIONS

Aufderheide, Tom P.. et al., "Electrocardiogramacteristics in EMD", Resuscitation, 1989 vol. 17 183-193.
Bonnemeier, H. et al., "Automated Continuous Chest Compression for in-hospital cardiopulmonary resuscitation of patients with pulse-less electrical activity: A report of five cases" International Journal of Cardiology, Elsevier, Amsterdam, NL, vol. 136, No. 2 Aug. 14, 2009.
Stueven, Harlan A. et al., "Electromechanical Dissociation: Six Years Prehospital Experience", Resuscitation, 1989 vol. 17 173-182.
Stueven, Harlan A. et al., "Defining Electromechanical Dissociation: Morphologic Presentation", Resuscitation, 1989 vol. 17 195-203.
Vanags, Brunoe et al., "Intervention is the Therapy of Electrome-chanical Dissociation", Resuscitation, 1989 vol. 17 163-171.
Skjeflo, Gunnar Waage et al., "ECG Changes During Resuscitation of Patients with Initial Pulseless Electrical Activity are Associated with Return of Spontaneious Circulation", Resuscitation, 2018 vol. 127 31-36.

* cited by examiner

322

400 — SET DEFAULT PEAK AMPLITUDE AND REFRACTORY PERIOD

401 — PRE-PROCESS THE ECG SIGNALS TO FILTER NOISE

402 — RECEIVE ECG DATA

404 — ANALYZE AND PROCESS ECG DATA TO DETECT Q-WAVE OR R-WAVE OF THE QRS COMPLEX

406 — SET THRESHOLD TO FACTOR OF R-WAVE AND THRESHOLD DECAY RATE

408 — SET REFRACTORY PERIOD BASED ON INTRINSIC HEARTRATE OF PATIENT

SYSTEMS AND METHODS OF SYNCHRONIZING CHEST COMPRESSIONS WITH MYOCARDIAL ACTIVITY

CLAIM OF PRIORITY

This application claims priority under 35 USC § 119(e) to U.S. Patent Application Ser. No. 62/681,287, filed on Jun. 6, 2018 and U.S. Patent Application Ser. No. 62/682,070, filed on Jun. 7, 2018, the entire contents of both are hereby incorporated by reference.

BACKGROUND

Cardiac arrest and other cardiac conditions are a major cause of death in the United States and around the world. Various resuscitation techniques, such as cardiopulmonary resuscitation (CPR), aim to maintain and/or restore a patient's circulatory and respiratory systems during cardiac arrest.

In general, during the administration of CPR, a patient's chest is repeatedly compressed so as to facilitate blood circulation throughout the patient's body. Additionally, periodic ventilations may also be provided to supply oxygen to the lungs and other organs within the body. Additionally, depending on the patient's medical condition, rescuers may administer shock therapies and/or medications to assist in the restoration of cardiopulmonary function to the patient.

SUMMARY

One category of cardiac condition is referred to as pseudo-pulseless electrical activity (p-PEA) or pulseless electrical activity (PEA), which may also be known as electromechanical dissociation (EMD). Potentially, a more generalized description of the symptoms of p-PEA, PEA, or EMD, would be unconscious hypotension with an organized ECG (electrocardiogram) activity. If there is a mechanical contraction of the heart muscle (as determined by echocardiogram), the condition would be considered p-PEA, but if there is no mechanical contraction the condition would be considered EMD, PEA or true-PEA. That is, unconscious hypotension with an organized ECG describes a series of symptoms which may encompass conditions such as pseudo-PEA and PEA. In general, all of the condition may be characterized by unconsciousness and/or unresponsiveness of the patient, and weak (or non-existent) hemodynamics in the presence of some organized electrical activity of the heart of the patient. During unconscious hypotension with an organized ECG, the heart will typically have an organized rhythm, but these rhythms do not correlate with life-sustaining mechanical activity of the heart. That is, there is detectable organized electrical activity of the myocardium, but weak or non-existent contractions of the heart muscle resulting in poor blood circulation that is generally not life-sustaining. Such a state of unconscious hypotension with organized ECG activity is life-threatening if left untreated.

An example of a system for providing chest compressions to a patient during cardiopulmonary resuscitation may comprise at least one ECG sensor configured to obtain ECG signals of the patient, an automated chest compressor configured to provide chest compressions to the patient, and at least one processor, memory and associated circuitry of a medical device communicatively coupled with the at least one ECG sensor and the automated chest compressor. The at least one processor may be configured to receive and ana-lyze the ECG signals of the patient, determine, based on the analysis, whether the patient is in a condition of unconscious hypotension with organized ECG, analyze, in response to a determination that the patient is in the condition of unconscious hypotension with organized ECG, the received ECG signals to detect a QRS complex, and generate an output to apply a chest compression at a predetermined time relative to the detected QRS complex.

Implementations of such a system may include one or more of the following features. The system may include an automated chest compressor that is configured to apply the chest compression such that a target depth of the chest compression is achieved within the predetermined time relative to the QRS complex. The system may be implemented such that the predetermined time relative to the QRS complex is a range approximately 125 milliseconds before a peak of an R-wave to 150 milliseconds after the peak of the R-wave. The system may be implemented such that the predetermined time relative to the QRS complex is a range approximately 100 milliseconds before a peak of an R-wave to 100 milliseconds after the peak of the R-wave. The system may be implemented such that the predetermined time relative to the QRS complex is a range approximately 75 milliseconds before a peak of an R-wave to 75 milliseconds after the peak of the R-wave. The system may be implemented such that target depth is a compression depth between 2 inches and 2.4 inches.

The system may be implemented such that the predetermined time relative to the QRS complex is a range from approximately 125 milliseconds before the peak of the R-wave of the QRS complex to 150 milliseconds after the peak of the R-wave. The system may be implemented such that the predetermined time relative to the QRS complex is a range from approximately 100 milliseconds before the peak of the R-wave to 100 milliseconds after the peak of the R-wave. The system may include at least one processor that is configured to generate the output to apply the chest compression synchronized with the R-wave within 100 milliseconds or less after the peak of the R-wave. The system may include at least one processor that is configured to generate the output to apply the chest compression synchronized with the R-wave within 50 milliseconds or less after the peak of the R-wave. The system may include at least one processor that is configured to generate the output to apply the chest compression synchronized with the R-wave within 125 milliseconds or less after the peak of the R-wave. The system may include at least one processor which is configured to generate the output to apply the chest compression synchronized with the R-wave less than 15 milliseconds or less after the peak of the R-wave. The system may include at least one processor that is configured to generate the output to apply the chest compression synchronized with the R-wave less than 5 milliseconds or less after the peak of the R-wave.

The system may include at least one processor that is configured to detect the QRS complex by identification of at least one of a Q-wave, a P-wave, and a leading edge of the R-wave prior to the occurrence of the peak of the R-wave. The system may include at least one processor that is further configured to generate the output to apply the chest compression synchronized with the R-wave 80 milliseconds or less before the peak of the R-wave. The system may include at least one processor is configured to generate the output to apply the chest compression synchronized with the R-wave 15 milliseconds or less before the peak of the R-wave. The system may include at least one processor that is configured to generate the output to apply the chest compression synchronized with the R-wave 10 milliseconds or less before the peak of the R-wave. The system may include at least one processor is configured to analyze the QRS complex to identify the R-wave prior to the peak of the R-wave, in order to generate the output synchronized at the peak of the R-wave.

The system may include at least one hemodynamic activity sensor configured to detect hemodynamic activity of the patient. The system may include at least one hemodynamic activity sensor that includes at least one of an invasive blood pressure sensor, pulse oximetry sensor, a Doppler ultrasonography sensor, a plethysmography sensor, a phonocardiography sensor, an echocardiography sensor, and a transthoracic impedance sensor. The system may include at least one hemodynamic activity sensor that includes a radio frequency sensor. The system may include an automated chest compressor that comprises a compression belt and a belt tensioner configured to tighten the compression belt around the thorax of the patient in order to compress the thorax of the patient at a resuscitative rate. The system may include a piston-based chest compressor that comprises a piston, a piston driver, support structures for supporting the piston and piston driver, and a compression pad affixed to the piston. The system may include a patient monitor, the patient monitor including an output device to generate audible or visual feedback to a rescuer.

The system may include visual feedback of at least one of a patient's heart rate, blood pressure, ECG waveform, aortic pressure (AOP), right atrial Pressure (RAP), intracranial pressure (ICP), carotid blood flow, jugular blood flow, and an indication of an applied chest compression. The system may include at least one processor that is configured to generate the output to apply the chest compression synchronized with the fiducial point within a range from approximately 125 milliseconds before the fiducial point to 150 milliseconds after the fiducial point. The system may include at least one processor that is configured to generate the output to apply the chest compression synchronized with the fiducial point within 125 milliseconds or less after the fiducial point. The system may include at least one processor that is configured to generate the output to apply the chest compression synchronized with the fiducial point within 100 milliseconds or less after the fiducial point. The system may include at least one processor that is configured to generate the output to apply the chest compression synchronized with the fiducial point within 100 milliseconds or less before the fiducial point.

An example of a system for providing chest compressions to a patient during cardiopulmonary resuscitation may comprise at least one ECG sensor configured to obtain ECG signals of the patient, a user interface including an input for receiving a hemodynamic status of the patient from a rescuer, an automated chest compressor communicatively coupled to the at least one processor that provides chest compressions to the patient in response to an output generated by the processor, at least one processor including memory and communicatively coupled with the at least one ECG sensor and the input for receiving hemodynamic status. The at least one processor may be configured to receive the ECG signals of the patient and the hemodynamic status of the patient, analyze the received ECG signals and the hemodynamic status to determine whether the patient is in a condition of unconscious hypotension with organized ECG, analyze, in response to a determination that the patient is in the condition of unconscious hypotension with organized ECG, the received ECG signals to detect a QRS complex, determine a QRS fiducial point based on the detected QRS complex, and generate an output to apply a chest compression at a predetermined time relative to the QRS fiducial point.

Implementations of such a system may include one or more of the following features. The system may include an automated chest compressor that is configured to apply the chest compression such that a target depth of the chest compression is achieved within the predetermined time relative to the QRS complex. The system may be implemented such that the predetermined time relative to the QRS complex is a range approximately 125 milliseconds before a peak of an R-wave to 150 milliseconds after the peak of the R-wave. The system may be implemented such that the predetermined time relative to the QRS complex is a range approximately 100 milliseconds before a peak of an R-wave to 100 milliseconds after the peak of the R-wave. The system may be implemented such that the predetermined time relative to the QRS complex is a range approximately 75 milliseconds before a peak of an R-wave to 75 milliseconds after the peak of the R-wave. The system may be implemented such that target depth is a compression depth between 2 inches and 2.4 inches.

The system may be implemented such that a predetermined time relative to the QRS fiducial point is a range from approximately 125 milliseconds before the peak of the R-wave to 150 milliseconds after the peak of the R-wave. The system may be implemented such that the at least one processor is configured to generate the output to apply the chest compression synchronized with the R-wave less than 50 milliseconds or less after the peak of the R-wave. The system may be implemented such that the at least one processor is configured to generate the output to apply the chest compression synchronized with the R-wave within 125 milliseconds or less after the peak of the R-wave. The system may be implemented such that the at least one processor is configured to generate the output to apply the chest compression synchronized with the R-wave within 100 milliseconds or less after the peak of the R-wave. The system may be implemented such that the at least one processor is configured to generate the output to apply the chest compression synchronized with the R-wave less than 15 milliseconds or less after the peak of the R-wave. The system may be implemented such that the at least one processor is configured to generate the output to apply the chest compression synchronized with the R-wave less than 5 milliseconds or less after the peak of the R-wave.

The system may be implemented such that the at least one processor is configured to detect the QRS complex by identification of a rising edge of the R-wave prior to the occurrence of the peak of the R-wave. The system may be implemented such that the at least one processor is configured to generate the output to apply the chest compression synchronized with the R-wave 35 milliseconds or less before the peak of the R-wave. The system may be implemented such that the at least one processor is configured to generate the output to apply the chest compression synchronized with the R-wave 15 milliseconds or less before the peak of the R-wave. The system may be implemented such that the at least one processor is configured to generate the output to apply the chest compression synchronized with the R-wave 10 milliseconds or less before the peak of the R-wave. The system may be implemented such that the at least one processor is configured to generate the output to apply the chest compression synchronized with the R-wave 5 milliseconds or less before the peak of the R-wave. The system may be implemented such that the at least one processor is configured to analyze the QRS complex to identify the R-wave prior to the peak of the R-wave, in order to generate the output synchronized at the peak of the R-wave.

The system may include an automated chest compressor that comprises a compression belt and a belt tensioner configured to tighten the compression belt around the thorax of the patient in order to compress the thorax of the patient at a resuscitative rate. The system may include a piston-based automated chest compressor that comprises a piston, a piston driver, support structures for supporting the piston and piston driver, and a compression pad affixed to the piston.

The system may include a patient monitor, the patient monitor including an output device to generate audible or visual feedback to a rescuer. The system may include a ventilator to provide ventilations to the patient during cardiopulmonary resuscitations. The system may include a ventilator that is configured to synchronize ventilations with the chest compressions of the automated chest compressor. The system may include at least one processor that is configured to generate the output to initiate the chest compression at a time from approximately 125 milliseconds before the peak of the R-wave to 150 milliseconds after the peak of the R-wave. The system may include at least one processor that is configured to generate the output to apply the chest compression such that the deepest point of the chest compression occurs at a time from approximately 125 milliseconds before the peak of the R-wave to 150 milliseconds after the peak of the R-wave.

An example of a method for providing chest compressions to a patient during cardiopulmonary resuscitation, the method may method comprise providing ECG signals of the patient from one or more ECG sensors to a patient monitor, providing an indication of hemodynamics of the patient to the patient monitor, analyzing the ECG signals and indication of hemodynamics to detect myocardial activity of the patient, and determining, based on the provided ECG signals an indication of hemodynamics, whether the patient is in a condition of unconscious hypotension with organized ECG. The method may include steps of: in response to a determination that the patient is in the condition of unconscious hypotension with organized ECG, detecting a QRS complex in the ECG signals, determining a QRS fiducial point in the QRS complex based on the detected QRS complex, and applying a chest compression at a predetermined time relative to the QRS fiducial point.

Implementations of such a system may include one or more of the following features. The method may include causing the chest compression to chest compressor to apply the such that a target depth of the chest compression is achieved within the predetermined time relative to the QRS complex. The method may be implemented such that the predetermined time relative to the QRS complex is a range approximately 125 milliseconds before a peak of an R-wave to 150 milliseconds after the peak of the R-wave. The method may be implemented such that the predetermined time relative to the QRS complex is a range approximately 100 milliseconds before a peak of an R-wave to 100 milliseconds after the peak of the R-wave. The method may be implemented such that the predetermined time relative to the QRS complex is a range approximately 75 milliseconds before a peak of an R-wave to 75 milliseconds after the peak of the R-wave. The method may be implemented such that the target depth is a compression depth between 2 inches and 2.4 inches.

The method may be implemented such that the at least one processor is configured to generate the output to apply the chest compression synchronized with the R-wave less than 50 milliseconds or less after the peak of the R-wave. The method may be implemented such that the at least one processor is configured to generate the output to apply the chest compression synchronized with the R-wave within 125 milliseconds or less after the peak of the R-wave. The method may be implemented such that the at least one processor is configured to generate the output to apply the chest compression synchronized with the R-wave within 100 milliseconds or less after the peak of the R-wave. The method may be implemented such that the at least one processor is configured to generate the output to apply the chest compression synchronized with the R-wave less than 15 milliseconds or less after the peak of the R-wave. The method may be implemented such that the at least one processor is configured to generate the output to apply the chest compression synchronized with the R-wave less than 5 milliseconds or less after the peak of the R-wave. The method may be implemented such that the at least one processor is configured to detect the QRS complex by identification of a rising edge of the R-wave prior to the occurrence of the peak of the R-wave.

The method may be implemented such that the at least one processor is configured to generate the output to apply the chest compression synchronized with the R-wave 35 milliseconds or less before the peak of the R-wave. The method may be implemented such that the at least one processor is configured to generate the output to apply the chest compression synchronized with the R-wave 15 milliseconds or less before the peak of the R-wave. The method may be implemented such that the at least one processor is configured to generate the output to apply the chest compression synchronized with the R-wave 10 milliseconds or less before the peak of the R-wave. The method may be implemented such that the at least one processor is configured to generate the output to apply the chest compression synchronized with the R-wave 5 milliseconds or less before the peak of the R-wave. The method may be implemented such that the at least one processor is configured to analyze the QRS complex to identify the R-wave prior to the peak of the R-wave, in order to generate the output synchronized at the peak of the R-wave. The method may be implemented such that the least one processor that is configured to generate the output to initiate the chest compression at a time from approximately 125 milliseconds before the peak of the R-wave to 150 milliseconds after the peak of the R-wave. The method may be implemented such that the at least one processor that is configured to generate the output to apply the chest compression such that the deepest point of the chest compression occurs at a time from approximately 125 milliseconds before the peak of the R-wave to 150 milliseconds after the peak of the R-wave.

An example of a system for providing chest compressions to a patient during cardiopulmonary resuscitation may comprise at least one ECG sensor configured to obtain ECG signals of the patient, an automated chest compressor communicatively coupled to an at least one processor that provides chest compressions to the patient in response to the output generated by the processor, at least one processor, memory and associated circuitry communicatively coupled with the at least one ECG sensor and the automated chest compressor. The at least one processor may be configured to receive and analyze the ECG signals of the patient, determine, based on the analysis, whether the patient is in a condition of unconscious hypotension with an organized ECG, analyze, in response to a determination that the patient is in the condition of unconscious hypotension with an organized ECG, the received ECG signals to determine a window relative to the detected QRS complex during which a chest compression is to be applied, and generate an output to apply a chest compression during the determined window.

Implementations of such a system may include one or more of the following features. The system may include an automated chest compressor that is configured to apply the chest compression such that a target depth of the chest compression is achieved within the predetermined time relative to the QRS complex. The system may be implemented such that the predetermined time relative to the QRS complex is a range approximately 125 milliseconds before a peak of an R-wave to 150 milliseconds after the peak of the R-wave. The system may be implemented such that the predetermined time relative to the QRS complex is a range approximately 100 milliseconds before a peak of an R-wave to 100 milliseconds after the peak of the R-wave. The system may be implemented such that the predetermined time relative to the QRS complex is a range approximately 75 milliseconds before a peak of an R-wave to 75 milliseconds after the peak of the R-wave. The system may be implemented such that target depth is a compression depth between 2 inches and 2.4 inches.

The system may be implemented such that the at least one processor is configured to generate the output to apply the chest compression synchronized with the R-wave less than 50 milliseconds or less after the peak of the R-wave. The system may be implemented such that the at least one processor is configured to generate the output to apply the chest compression synchronized with the R-wave within 125 milliseconds or less after the peak of the R-wave. The system may be implemented such that the at least one processor is configured to generate the output to apply the chest compression synchronized with the R-wave within 100 milliseconds or less after the peak of the R-wave. The system may be implemented such that the at least one processor is configured to generate the output to apply the chest compression synchronized with the R-wave less than 15 milliseconds or less after the peak of the R-wave. The system may be implemented such that the at least one processor is configured to generate the output to apply the chest compression synchronized with the R-wave less than 5 milliseconds or less after the peak of the R-wave.

The system may be implemented such that the at least one processor is configured to detect the QRS complex by identification of a rising edge of the R-wave prior to the occurrence of the peak of the R-wave. The system may be implemented such that the at least one processor is configured to generate the output to apply the chest compression synchronized with the R-wave 35 milliseconds or less before the peak of the R-wave. The system may be implemented such that the at least one processor is configured to generate the output to apply the chest compression synchronized with the R-wave 15 milliseconds or less before the peak of the R-wave. The system may be implemented such that the at least one processor is configured to generate the output to apply the chest compression synchronized with the R-wave 10 milliseconds or less before the peak of the R-wave. The system may be implemented such that the at least one processor is configured to generate the output to apply the chest compression synchronized with the R-wave 5 milliseconds or less before the peak of the R-wave. The system may be implemented such that the at least one processor is configured to analyze the QRS complex to identify the R-wave prior to the peak of the R-wave, in order to generate the output synchronized at the peak of the R-wave. The system may include an automated chest compressor that comprises a compression belt and a belt tensioner configured to tighten the compression belt around the thorax of the patient in order to compress the thorax of the patient at a resuscitative rate.

The system may include a piston-based automated chest compressor that comprises a piston, a piston driver, support structures for supporting the piston and piston driver, and a compression pad affixed to the piston. The system may include a patient monitor, the patient monitor including an output device to generate audible or visual feedback to a rescuer. The system may include a ventilator to provide ventilations to the patient during cardiopulmonary resuscitations. The system may include a ventilator that is configured to synchronize ventilations with the chest compressions of the automated chest compressor. The system may include at least one processor that is configured to generate the output to initiate the chest compression at a time from approximately 125 milliseconds before the peak of the R-wave to 150 milliseconds after the peak of the R-wave. The system may include at least one processor that is configured to generate the output to apply the chest compression such that the deepest point of the chest compression occurs at a time from approximately 125 milliseconds before the peak of the R-wave to 150 milliseconds after the peak of the R-wave.

An example of a system for providing chest compressions to a patient during cardiopulmonary resuscitation may comprise at least one ECG sensor configured to obtain ECG signals of the patient, a user interface including an input for receiving a hemodynamic status of the patient from a rescuer, an automated chest compressor communicatively coupled to the at least one processor that provides chest compressions to the patient in response to the output generated by the processor, and at least one processor including memory and communicatively coupled with the at least one ECG sensor and the input for receiving hemodynamic status. The at least one processor may be configured to receive the ECG signals of the patient and the hemodynamic status of the patient, analyze the received ECG signals and the hemodynamic status to determine whether the patient is in a pulseless electrical activity condition, in response to a determination that the patient is in the pulseless electrical activity condition, analyze the received ECG signals to detect a QRS complex and determine a window relative to the detected QRS complex during which a chest compression is to be applied, and generate an output to apply a chest compression during the determined window.

Implementations of such a system may include one or more of the following features. The system may include an automated chest compressor that is configured to apply the chest compression such that a target depth of the chest compression is achieved within the predetermined time relative to the QRS complex. The system may be implemented such that the predetermined time relative to the QRS complex is a range approximately 125 milliseconds before a peak of an R-wave to 150 milliseconds after the peak of the R-wave. The system may be implemented such that the predetermined time relative to the QRS complex is a range approximately 100 milliseconds before a peak of an R-wave to 100 milliseconds after the peak of the R-wave. The system may be implemented such that the predetermined time relative to the QRS complex is a range approximately 75 milliseconds before a peak of an R-wave to 75 milliseconds after the peak of the R-wave. The system may be implemented such that target depth is a compression depth between 2 inches and 2.4 inches.

The window may be from approximately 125 milliseconds before the peak of the R-wave to 150 milliseconds after the peak of the R-wave. The system may include at least one processor that is configured to identify the R-wave prior to the peak of the R-wave, generate an output indicating the R-wave is identified, and determine synchronization based on the generated out. The starting point for the window relative to the detected QRS complex may include generated output. The system may include a patient monitor, the patient monitoring including at least one audible or visual output. The visual output may display the QRS complex and the window relative to the detected QRS complex during which a chest compression is to be applied.

The timing and bounds of the window may be displayed on a display device of the patient monitor and may be adjustable by rescuers. The timing and bounds of the window may be displayed on the display device may be adjusted via a touchscreen interface. The system may include at least one processor is configured to generate the output to apply the chest compression within the determined window and 100 milliseconds or less before the peak of the R-wave. The system may include at least one processor that is configured to generate the output to apply the chest compression within the determined window and 50 milliseconds or less before the peak of the R-wave. The system may include at least one processor that is configured to analyze the QRS complex to identify the R-wave prior to the peak of the R-wave, in order to generate the output synchronized at the peak of the R-wave.

The system may include at least one hemodynamic activity sensor configured to detect hemodynamic activity of the patient. The at least one hemodynamic activity sensor may include at least one sensor for detecting pulse oximetry, Doppler ultrasonography, plethysmography, phonocardiography, echocardiography, and transthoracic impedance. The system may include at least one hemodynamic activity sensor is a radio frequency sensor. The system may include an automated chest compressor that comprises a compression belt and a belt tensioner configured to tighten the compression belt around the thorax of the patient in order to compress the thorax of the patient at a resuscitative rate. The system may include an automated chest compressor is a piston-based system that comprises a piston, a piston driver, support structures for supporting the piston and piston driver, and a compression pad affixed to the piston.

The system may include a patient monitor, the patient monitor including an output device to generate audible or visual feedback to a rescuer. The visual feedback may include at least one of a patient's heart rate, blood pressure, ECG waveform, aortic pressure (AOP), right atrial Pressure (RAP), intracranial pressure (ICP), carotid blood flow, jugular blood flow, and generated output to apply a chest compression. The system may include a ventilator to provide ventilations to the patient during cardio pulmonary resuscitations. The ventilator may synchronize ventilations with the chest compressions of the automated chest compressor. The system may include at least one processor that is configured to generate the output to initiate the chest compression at a time from approximately 125 milliseconds before the peak of the R-wave to 150 milliseconds after the peak of the R-wave. The system may include at least one processor that is configured to generate the output to apply the chest compression such that the deepest point of the chest compression occurs at a time from approximately 125 milliseconds before the peak of the R-wave to 150 milliseconds after the peak of the R-wave.

An example of a method for providing chest compressions to a patient during cardiopulmonary resuscitation may comprise providing ECG signals of the patient from one or more ECG sensors to a patient monitor, providing an indication of hemodynamics of the patient to the patient monitor, analyzing the ECG signals and indication of hemodynamics to detect myocardial activity of the patient, determining, based on the provided ECG signals and indication of hemodynamics, whether the patient is in a pulseless electrical activity condition, and in response to a determination that the patient is in the pulseless electrical activity condition, determining a QRS fiducial point, applying, via an automated chest compressor, a chest compression after the QRS fiducial point and within a predetermined time period.

Implementations of such a system may include one or more of the following features. The method may include causing the chest compression to chest compressor to apply the such that a target depth of the chest compression is achieved within the predetermined time relative to the QRS complex. The method may be implemented such that the predetermined time relative to the QRS complex is a range approximately 125 milliseconds before a peak of an R-wave to 150 milliseconds after the peak of the R-wave. The method may be implemented such that the predetermined time relative to the QRS complex is a range approximately 100 milliseconds before a peak of an R-wave to 100 milliseconds after the peak of the R-wave. The method may be implemented such that the predetermined time relative to the QRS complex is a range approximately 75 milliseconds before a peak of an R-wave to 75 milliseconds after the peak of the R-wave. The method may be implemented such that the target depth is a compression depth between 2 inches and 2.4 inches.

The method may be implemented such that the at least one processor is configured to generate the output to apply the chest compression synchronized with the R-wave less than 50 milliseconds or less after the peak of the R-wave. The method may be implemented such that the at least one processor is configured to generate the output to apply the chest compression synchronized with the R-wave within 125 milliseconds or less after the peak of the R-wave. The method may be implemented such that the at least one processor is configured to generate the output to apply the chest compression synchronized with the R-wave within 100 milliseconds or less after the peak of the R-wave. The method may be implemented such that the at least one processor is configured to generate the output to apply the chest compression synchronized with the R-wave less than 15 milliseconds or less after the peak of the R-wave. The method may be implemented such that the at least one processor is configured to generate the output to apply the chest compression synchronized with the R-wave less than 5 milliseconds or less after the peak of the R-wave. The method may be implemented such that the at least one processor is configured to detect the QRS complex by identification of a rising edge of the R-wave prior to the occurrence of the peak of the R-wave.

The method may be implemented such that the at least one processor is configured to generate the output to apply the chest compression synchronized with the R-wave 35 milliseconds or less before the peak of the R-wave. The method may be implemented such that the at least one processor is configured to generate the output to apply the chest compression synchronized with the R-wave 15 milliseconds or less before the peak of the R-wave. The method may be implemented such that the at least one processor is configured to generate the output to apply the chest compression synchronized with the R-wave 10 milliseconds or less before the peak of the R-wave. The method may be implemented such that the at least one processor is configured to generate the output to apply the chest compression synchronized with the R-wave 5 milliseconds or less before the peak of the R-wave. The method may be implemented such that the at least one processor is configured to analyze the QRS complex to identify the R-wave prior to the peak of the R-wave, in order to generate the output synchronized at the peak of the R-wave. The method may be implemented such that the least one processor that is configured to generate the output to initiate the chest compression at a time from approximately 125 milliseconds before the peak of the R-wave to 150 milliseconds after the peak of the R-wave. The method may be implemented such that the at least one processor that is configured to generate the output to apply the chest compression such that the deepest point of the chest compression occurs at a time from approximately 125 milliseconds before the peak of the R-wave to 150 milliseconds after the peak of the R-wave.

An example of a system for providing chest compressions to a patient during cardiopulmonary resuscitation may comprise at least one ECG sensor configured to obtain ECG signals of the patient, at least one hemodynamic activity sensor configured to detect hemodynamic activity of the patient, an automated chest compressor configured to provide chest compressions to the patient, and at least one processor, memory and associated circuitry of a medical device communicatively coupled with the at least one ECG sensor, the at least one hemodynamic activity sensor, and the automated chest compressor. The at least one processor may be configured to receive and analyze the ECG signals of the patient and the hemodynamic activity of the patient, determine, based on the analysis, whether the patient is in a condition of unconscious hypotension with organized ECG, analyze, in response to a determination that the patient is in the condition of unconscious hypotension with organized ECG, the received ECG signals to detect a QRS complex, and generate an output to apply a chest compression within a predetermined time relative to the detected QRS complex, receive and analyze the motions signals motion signals of the patient to determine a chest compression depth and cause the automated chest compressor to apply the chest compressions such that a target depth is achieved within the predetermined time.

Implementations of such a system may include one or more of the following features. The system may include an automated chest compressor that is configured to apply the chest compression such that a target depth of the chest compression is achieved within the predetermined time relative to the QRS complex. The predetermined time relative to the QRS complex may include a range approximately 125 milliseconds before a peak of an R-wave to 150 milliseconds after the peak of the R-wave. The predetermined time relative to the QRS complex may include a range approximately 100 milliseconds before a peak of an R-wave to 100 milliseconds after the peak of the R-wave. The predetermined time relative to the QRS complex may include a range approximately 75 milliseconds before a peak of an R-wave to 75 milliseconds after the peak of the R-wave. The target depth may include a compression depth between 2 inches and 2.4 inches.

The predetermined time relative to the QRS complex may include a range from approximately 125 milliseconds before the peak of the R-wave to 150 milliseconds after the peak of the R-wave. The predetermined time relative to the QRS complex may include a range from approximately 100 milliseconds before the peak of the R-wave to 100 milliseconds after the peak of the R-wave. The system may include at least one processor that is configured to generate the output to apply the chest compression synchronized with the R-wave within 50 milliseconds or less after the peak of the R-wave. The system may include at least one processor that is configured to generate the output to apply the chest compression synchronized with the R-wave within 125 milliseconds or less after the peak of the R-wave. The system may include at least one processor that is configured to generate the output to apply the chest compression synchronized with the R-wave within 100 milliseconds or less after the peak of the R-wave. The system may include at least one processor that is configured to generate the output to apply the chest compression synchronized with the R-wave 15 milliseconds or less after the peak of the R-wave. The system may include at least one processor that is configured to generate the output to apply the chest compression synchronized with the R-wave 5 milliseconds or less after the peak of the R-wave. The system may include at least one processor that is configured to detect the QRS complex by identification of at least one of: a Q-wave and the leading edge of the R-wave prior to occurrence of the peak of the R-wave. The system may include at least one processor that is configured to generate the output to apply the chest compression synchronized with the R-wave 80 milliseconds or less before the peak of the R-wave. The system may include at least one processor that is configured to generate the output to apply the chest compression synchronized with the R-wave 15 milliseconds or less before the peak of the R-wave.

The system may include at least one processor that is configured to generate the output to apply the chest compression synchronized with the R-wave 10 milliseconds or less before the peak of the R-wave. The system may include at least one processor that is configured to analyze the QRS complex to identify the R-wave prior to the peak of the R-wave, in order to generate the output synchronized at the peak of the R-wave.

The system may include at least one hemodynamic activity sensor configured to detect hemodynamic activity of the patient. The at least one hemodynamic activity sensor may include at least one of: an invasive blood pressure sensor, pulse oximetry sensor, a Doppler ultrasonography sensor, a plethysmography sensor, a phonocardiography sensor, an echocardiography sensor, and a transthoracic impedance sensor. The at least one hemodynamic activity sensor may include a radio frequency sensor. The system may include an automated chest compressor that comprises a compression belt and a belt tensioner configured to tighten the compression belt around the thorax of the patient in order to compress the thorax of the patient at a resuscitative rate. The system may include an automated chest compressor that is a piston-based system that comprises a piston, a piston driver, support structures for supporting the piston and piston driver, and a compression pad affixed to the piston. The system may include a patient monitor, the patient monitor including an output device to generate audible or visual feedback to a rescuer. The visual feedback may include at least one of a patient's heart rate, blood pressure, ECG waveform, aortic pressure (AOP), right atrial Pressure (RAP), intracranial pressure (ICP), carotid blood flow, jugular blood flow, and an indication of an applied chest compression

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
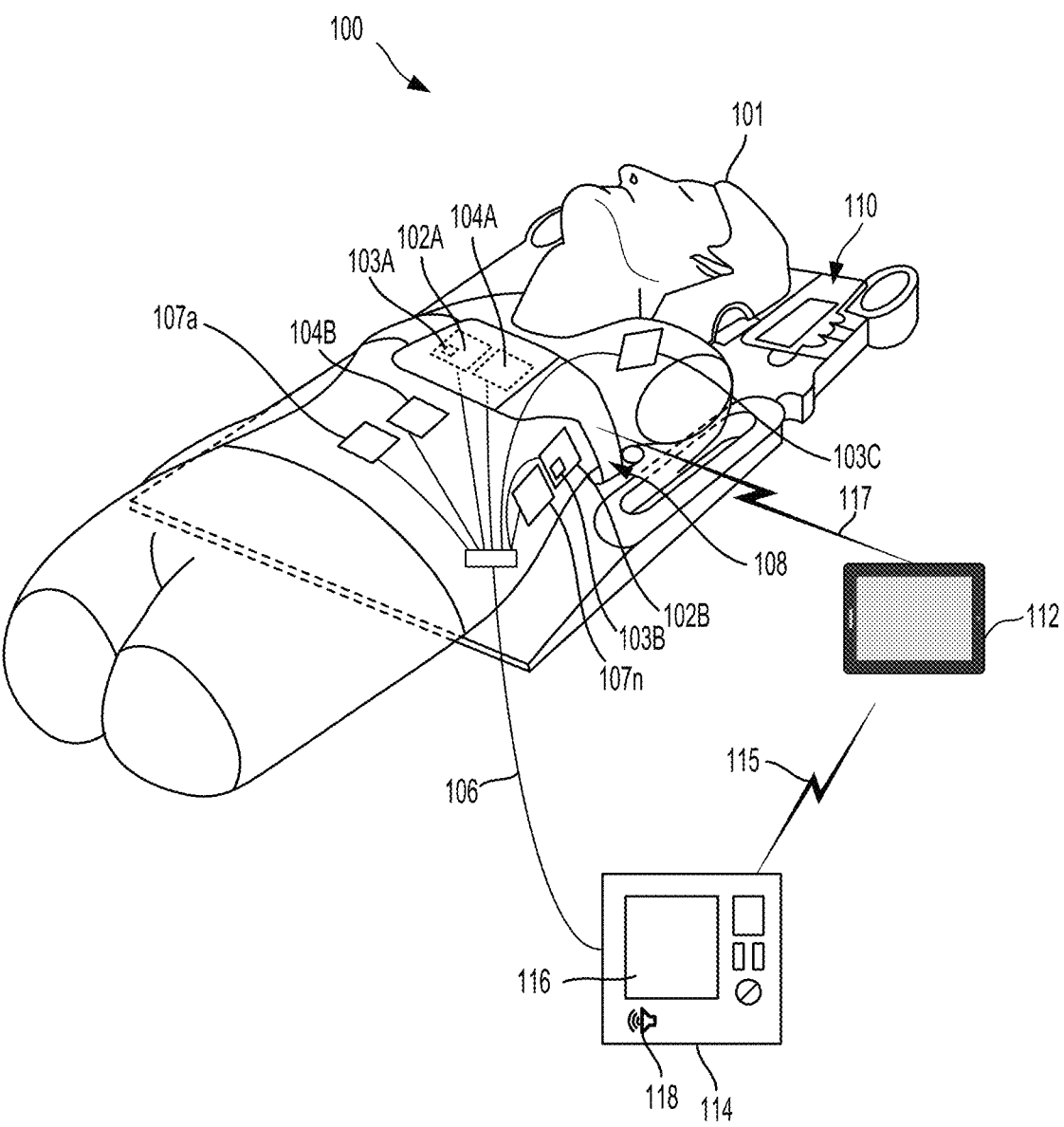
FIG. 1A is a schematic diagram of an illustrative embodiment of a medical system including a patient monitor and an automated chest compression device.

The presently disclosed systems and methods relate to techniques and devices that may be used to increase cardiac output for patient(s) suffering from cardiac ailments, where the patient appears to be lifeless, yet has some electrical heart activity and may further include some residual mechanical heart activity. This condition may be described as unconscious hypotension with organized electrocardiogram (ECG) activity, which may include conditions commonly referred to as pulseless electrical activity (PEA), electromechanical disassociation (EMD), or pseudo-PEA. A patient suffering from unconscious hypotension with organized ECG activity may have some electrical activity of the heart, but weak (or no) corresponding mechanical activity. The systems and methods of the present disclosure increase cardiac output in such patients by sensing electrical signals that are indicative of a patient's beating heart and synchronize resuscitative therapies, such as chest compressions, with myocardial heart wall motion.

In various embodiments described herein, once unconscious hypotension with an organized ECG is detected, one or more chest compression protocols may be applied to the patient (e.g., via an automated mechanical chest compressor, via an active compression-decompression device, or via manual chest compressions) according to a timing and synchronization. In one example, the timing is such that a target or maximum depth of the chest compression is reached within 125 milliseconds before a peak of an R-wave to 150 ms after the peak of the R-wave. Research performed by a portion of the inventors has found that such timing results in enhanced forward blood flow from the heart toward peripheral tissues. The timing of such chest compressions may be such that the chest compressions are effectively applied upon detection of the R-wave in a QRS complex. For example, the chest compressions may be initiated after the detection of a QRS complex (e.g., detection on the leading edge of the Q-wave or R-wave) or after determination of a QRS fiducial point.

In one implementation, the chest compression will be initiated such that the chest compression is synchronized with the R-wave and such that a target depth is reached within 150 milliseconds or less before or after the peak of the R-wave. Once the target depth is achieved, the medical devices and/or the chest compressor may initiate a "hold" portion of the chest compression cycle, followed by an upstroke (or release) portion of the compression cycle. For some embodiments, the target depth of the compression will be reached within 150 milliseconds or less, or within 100 milliseconds or less after the peak of the R-wave. Or, in certain embodiments, the target depth of compression may be reached prior to the peak of the R-wave. Additionally, in some embodiments, the target depth will be determined to have been achieved so long as 90% of the target depth of the chest compression is reached. Or, put another way, the actual depth of compression may be within approximately 10% of the target depth. Illustrated by way of example, if the target depth of the compressor is 2.0 inches, then the actual depth of compression may be between approximately 1.8-2.2 inches. In one embodiment, the target depth is based on current American Heart Association (AHA) guidelines which are currently: approximately 2.0-2.4 inches for an adult, approximately one-third the diameter of the chest of a child or (e.g., about 2.0 inches, and 1.5 inches, respectively).

In some cases, as further described below, the chest compressions may be initiated on, or before, the peak of the R-wave of the detected QRS complex, so that the target depth is reached within a preferred period of time (e.g., within 150 ms) before or after the peak of the R-wave. As an example, the R-wave may be detected on its initial rising edge (or falling edge, depending on whether the R-wave is above or below the baseline) prior to the actual occurrence of the R-wave peak. A QRS fiducial point is set, from which a delay may or may not be implemented before a chest compression is applied by a chest compressor. If such a delay is smaller than the time duration from the QRS fiducial that precedes the R-wave to the occurrence of the R-wave itself, then the chest compression may be initiated before the R-wave reaches its peak. As a result, there may be a relatively short period elapsed between the peak of the R-wave and the time at which the target depth of compression is reached.

Figure 10A:
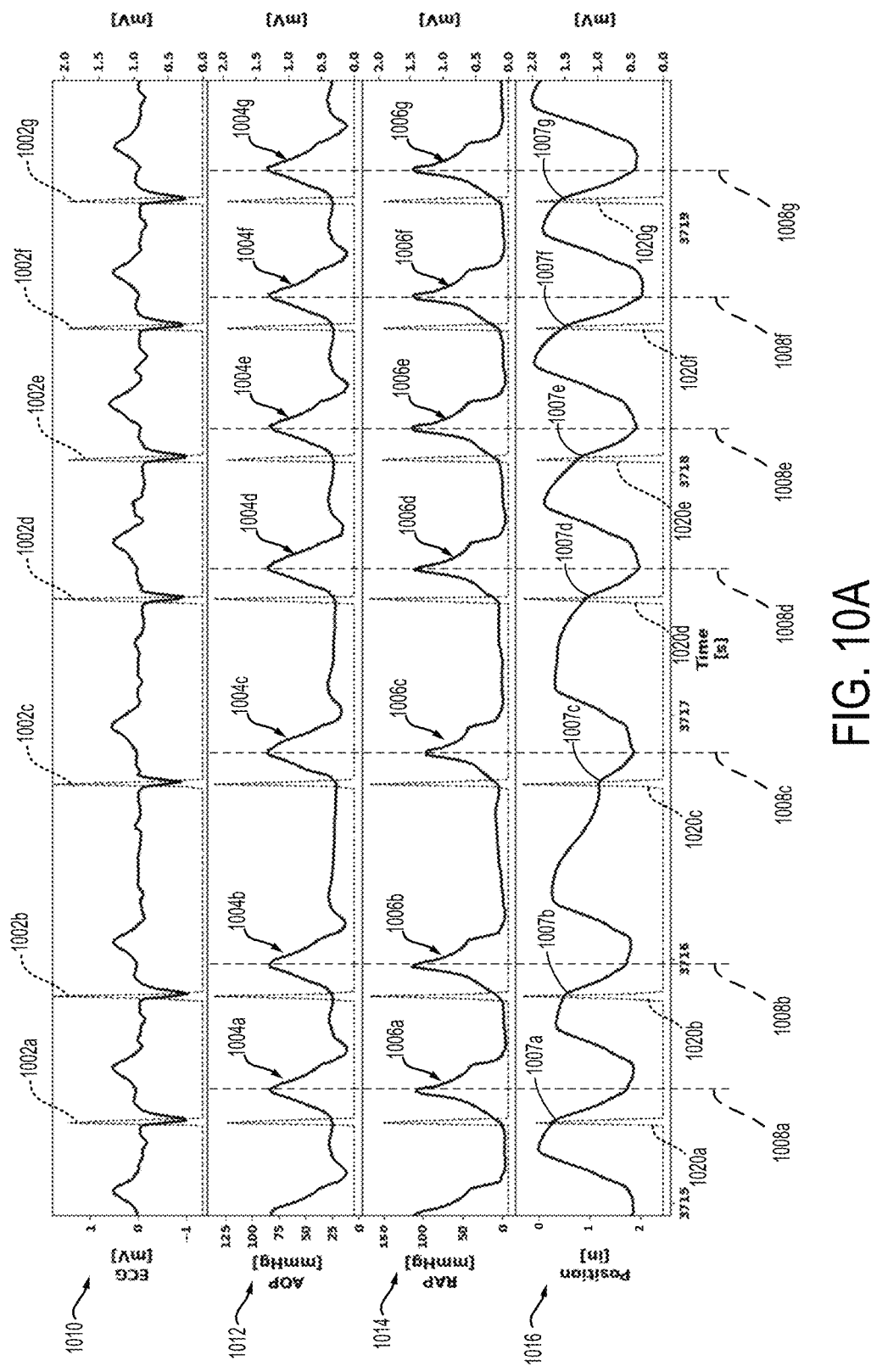
FIGS. 10A and 10B illustrate waveforms from the study detailed in FIGS. 9A-9C, and illustrates various relationships between a detected QRS complex, the initiation of a chest compression and associated pressure measurements.
Figure 10B:
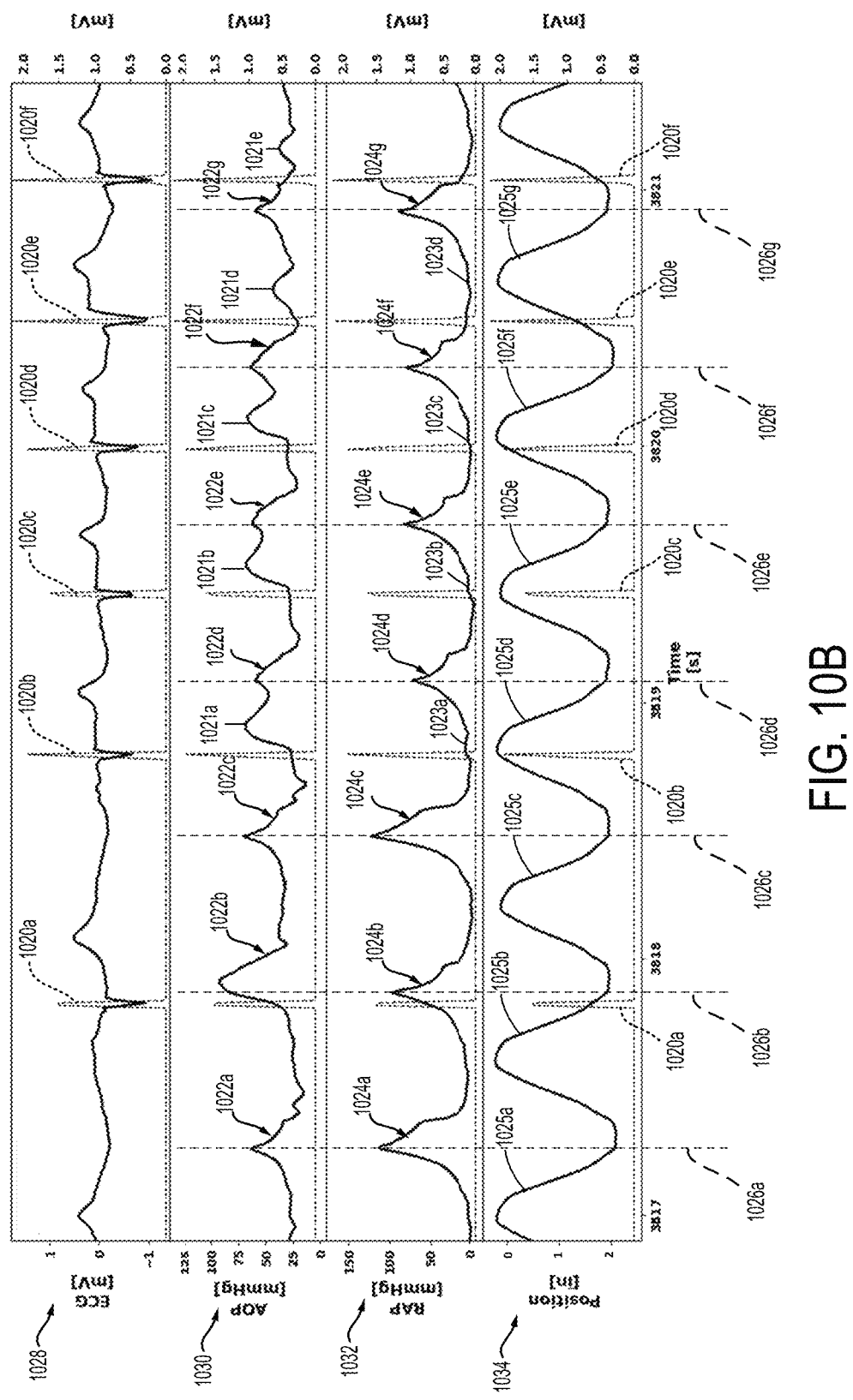

On the other hand, a relatively long delay after the peak of the R-wave (e.g., target depth reached after 150 milliseconds from the peak of the R-wave) may result in a comparatively weak hemodynamic output as compared to chest compressions applied earlier in time (as detailed in FIG. 10B, for example). Additionally, synchronized chest compressions may be implemented to avoid the occurrence of chest compressions during periods of diastole, which is the phase of the cardiac cycle during which the heart refills with blood after the emptying done during systole (i.e., when the heart muscle contracts). Applying chest compressions during diastole may result in ineffective perfusion or possibly damage the patient's heart. Accordingly, applying chest compressions according to synchronized timings discussed herein may result in enhanced hemodynamic output and help avoid potential damage to the patient's heart (as detailed in FIG. 10B).

At one end of such a hemodynamic spectrum is normal spontaneous circulation. This is where the cardiac activity is normal and left ventricular mechanical and pumping function are normal. Below that level is hypotension and then compensated shock. In such cases, the blood pressure and the patient's pulse are still palpable and there may be good cardiac output. However, for various reasons, the cardiac output is unable to meet the metabolic demands of the body and homeostasis is at risk. This is evident by parameters such as decreasing urine output and increasing serum lactate, which are markers of inadequate organ function.

The state of uncompensated shock occurs after compensated shock and is a more severe condition. This is a state in which the myocardium and the cardiovascular system are no longer able to provide adequate amounts of blood flow, oxygen, and nutrients to meet the needs of vital organs, and the function of those organs is affected to the extent that they are beginning to become damaged. Blood pressures in this state might be, for example, 70/30 mmHg. systolic over diastolic. Also, urine output may cease, and the patient may become confused because of inadequate cerebral function. Importantly, as shock progresses, the pathways to multiorgan system failure are initiated.

Following classical uncompensated shock is what might be called "extreme shock" which borders on cardiac arrest. In this case, the patient exhibits some residual myocardial function including some left ventricular ejection, but cardiac output is wholly inadequate to meet the needs of vital organs. For example, cardiac output might be less than 1 liter per minute, blood pressure might be 50/20 mmHg, urine output may be minimal or absent, and the patient may be stuporous or comatose. Further, the patient may appear to be near death with significantly impaired cerebral function and stupor bordering on coma. If untreated, extreme shock will result in true cardiac arrest in a timeframe of minutes. Generally, it is not possible to palpate arterial pulses manually in this range, and such patients may be classified as PEA (or p-PEA) by clinical personnel even though their heart continues to beat, albeit weakly.

Following the state of extreme shock is pulseless electrical activity (PEA) cardiac arrest, which importantly also has a spectrum of conditions and a range of hemodynamics. For example, at its upper end, PEA has both left ventricular mechanical function and cardiac output, but the output is not sufficient enough to be detected at a peripheral radial or femoral pulse. This upper end is often referred to as pseudo-PEA. However, a more appropriate description may be unconscious hypotension with an organized ECG, which describes an unconscious patient, suffering from hypotension, but has an organized ECG.

If an intra-arterial catheter were placed into the patient, the blood pressure might be only 45/25 mmHg, with blood pressure measurable only in major arteries of the chest, neck or groin. A Doppler probe placed over the neck or groin may detect forward blood flow. Blood flow is so profoundly inadequate that the patient will generally appear lifeless and their pupils may dilate and become fixed. Further, they appear to be in cardiac arrest despite the presence of residual pump function and minimal forward blood flow. The high end of PEA dynamics overlaps the low end of "extreme shock." In such cases, the clinical personnel (e.g., rescuers) may not be able to distinguish the difference.

Following the "high end" stage of PEA is electromechanical dissociation (or EMD) with almost absent left ventricular mechanical function. The blood pressure measured by intravascular catheters just above the aortic valve will show aortic pulsations, but the blood pressures measured are on the order of 25/15 mmHG, and there will be almost no associated forward blood flow. Without the application of CPR, oxygen delivered will be essentially absent and irreparable injury to organs such as the brain occurs within minutes.

The final stage of PEA is an organized electrical rhythm but no left ventricular mechanical function. This is true cardiac arrest. Catheter measuring pressure above the aortic valve will detect no pressure pulse and echocardiography will show no cardiac movement. Further, the cardiac output is non-existent and the patient is in complete global ischemia and cardiac arrest. Without the application of CPR, no blood or oxygen is circulated and irreparable injury to vital organs (e.g., the brain) can occur within minutes.

In a typical implementation, the present system is used to detect electrical and mechanical activity (if present) and to synchronize intrinsic cardiac activity with resuscitation techniques, such as those used in CPR (including chest compressions/decompressions and/or ventilation). Hence, the present system may be utilized in any pathophysiologic state including, cardiac arrest, PEA, pseudo-PEA, unconscious hypotension with an organized ECG, and through the various stages of shock, and/or in any state in which residual myocardial function with and without mechanical cardiac output exists. By synchronizing chest compressions with the intrinsic heartbeats of the patent, intrinsic cardiac output is augmented, and overall cardiac output and organ profusion may be increased, thereby improving the blood flow of patients with impaired hemodynamics.

Further illustrated by way of example, one situation that often occurs and is particularly challenging for physicians, is when patients are progressing from shock to PEA. In the earlier stages of this process, physicians tend to treat such patients with intravenous medications and possibly controlled ventilation. While drugs such as antibiotics may be administered to patients in states such as septic shock, pressor drugs such as dopamine continue to be a mainstay of treatment. Pressors, however, have generally not been shown to improve the outcome of such patients despite raising the blood pressure. This may be because they improve blood pressure but also raise vital organ oxygen utilization, such that the overall balance between oxygen supply and demand is not improved. Pressor drugs also have significant direct vital organ toxicity.

If, however, these parenteral therapies do not stabilize the patient, then the patient may progress towards more and more extreme states (e.g., cardiac arrest). Many medical practitioners in emergency medicine and critical care continue to be unsure—and the medical literature remains unclear—as to what point a patient whose blood pressure is dropping should begin to receive chest compressions. Indeed, physicians generally do not apply techniques such as external chest compress before subjective loss of vital signs. This is because CPR, and in particular chest compressions, can interfere with intrinsic cardiac function and in particular cardiac filling if applied in an unsynchronized manner. For instance, a patient whose blood pressure is 60/40 who begins to receive chest compressions out of synchronization with heart function could rapidly progress into full cardiac arrest. More specifically, in performing CPR without synchronization, application of the compression phase when the left ventricle is trying to fill may significantly decrease cardiac output on the next ejection secondary to the Frank Starling Law of the heart. Hence, by detecting myocardial mechanical function and/or electrical activity, chest compressions can be synchronized with the ejection phase so that patients in shock may be treated without exacerbating their condition and causing the patient to progress further toward cardiac arrest.

Hence, the issue as to when chest compressions should begin when a patient is progressing through the stages of shock may be addressed by synchronizing chest compressions, and possibly other mechanical adjuncts, with the ejection and relaxation phases, so that the clinician may be more confident that chest compressions are assisting and not interfering with residual circulatory function. In this way, the clinician does not need to be as concerned with the question as to when to begin chest compressions. In this manner, the present system may allow the use of external mechanical adjuncts in the treatment of any form of shock in a manner similar to the methods by which intra-aortic balloon counterpulsation has been applied in cardiogenic shock. The present system may thus allow the application of such adjuncts in the pre-hospital, and Emergency Department environments.

Another advantage of using synchronization is that it may be performed as an adjunct to therapies directed at the cause of the shock, such as antibiotics or thrombolysis, enhancing vital organ perfusion while these therapies are being administered. Indeed, improved hemodynamics may not only stave off organ injury, but it may also improve the efficacy of parenteral therapies. Further, synchronized chest compressions are unlikely to have significant organ toxicity, unlike pressor drugs.

As described above, one particular application of the present system is in connection with those suffering from pulseless electrical activity (PEA). PEA is one of the three broad-types of cardiac arrest, the other two being ventricular fibrillation and asystole. PEA is also referred to as electro-mechanical disassociation (EMD). PEA has been described as "the presence of organized electrical activity on the electrocardiogram but without palpable pulses." Rosen P, Baker F J, Barkin R M, Braen G R, Dailey R H, Levy R C. Emergency Medicine Concepts and Clinical Practice. 2nd ed. St Louis: C V Mosby, 1988. Unlike ventricular fibrillation, which can be specifically reversed with electrical countershock, PEA does not have a specific countermeasure. This may explain the traditionally worse outcome of patients in PEA compared to ventricular fibrillation. Unfortunately, the incidence of PEA is increasing, possibly because early risk modification is changing the natural history of cardiovascular disease. It is now reported by some authorities that the majority of patients in cardiac arrest are in PEA at the time of EMS arrival. Additionally, a significant fraction of patients that are shocked out of ventricular fibrillation, or resuscitated from asystole, will experience PEA at some point during their resuscitation. The combination of these circumstances means that a large majority of patients receiving advanced life support for the treatment of cardiac arrest will have PEA at some time during resuscitation. Hence, now or in the near future, PEA may supersede classical ventricular fibrillation in importance.

Many patients suffering from unconscious hypotension with an organized ECG may have some residual cardiac mechanical activity, and many have detectable blood pressures. In such cases, the patient may appear lifeless (e.g., unconscious) and without a pulse. However, there often remains some degree of residual left ventricular function. Hence, one important feature of the present system is to sense when the patient still has some myocardial function and then to synchronize phasic resuscitation therapies, especially compression of the chest, with the heart's residual mechanical function. In this way, the compression phase of CPR may occur during the ejection phase, and the relaxation phase can allow elastic recoil of the chest—with associated decreases in intrathoracic pressure when the left ventricle is trying to fill. In this way, synchronizing phasic resuscitative therapies with residual ventricular ejection and filling may improve hemodynamics, the rate of a return to spontaneous circulation (ROSC), and long term survival.

The present system may incorporate various non-invasive sensing technologies to acquire real-time data describing the pattern of myocardial wall and or valve motion so as to allow synchronization of chest compressions and other therapies. If, however, invasive indicators of hemodynamics, such as intra-arterial pressure or flow monitors, are present, then the present system may act as an interface between those inputs and phasic resuscitative therapies as exemplifies by external chest compression. To apply proper synchronization between the forces of external devices, on or around the chest or body, and the ejection and filling phases of residual left ventricular function, a variety of devices may be used. The decision that residual myocardial activity exists may be made from a logic circuit with inputs from multiple sensing modalities. The present system may utilize sensing technology to collect the data on myocardial wall function, myocardial valve motion, blood flow in vascular structures, vital organ oxygen or energy status, or exhaled pulmonary gas, and this data may be passed through logic circuits and a controlling output signal passed to the devices that deliver therapies. Because the pattern of mechanical residual wall function may be variable over time, the present system may be designed to promptly identify the residual function and to vary therapeutics based on feedback to a logic circuit. Also, the synchronizing of external chest compressions may be used with other techniques, such as with abdominal counter pulsations, phasic limb compression, ventilation, and electrical stimulation, among others, to augment cardiac ejection and filling. In this way, the patient may be stabilized to allow sufficient time for primary therapies, such as thrombolysis, to be effective.

A wide variety of equipment and devices may be used to provide chest compressions. For example, various types of automated compression systems may be used to compress the chest. These include systems, such as the AutoPulse Resuscitation System, by ZOLL Medical Corporation, the Thumper manufactured by Michigan Instruments, or the LUCAS device, to list a few examples. Further, the present system is not limited to automated compression systems, but may be used with manual techniques as well. For example, the present system may be used to provide an audio and/or visual signals to indicate to a rescuer as to when to manually apply chest compressions to the patient.

In addition to synchronizing chest compressions with residual heart function, the present system may also be used to synchronize ventilations with residual heart function. For example, inspiration and expiration may be synchronized with residual myocardial function so as to increase cardiac output. For instance, inspiration may be synchronized to systole and expiration with diastole. To apply ventilations, the present system may use a traditional ventilator or ventilations may be provided manually, such as by using a ventilator bag. In the latter case, an audio and/or visual signal may be provided to the rescuer as to when to apply proper ventilations.

With both chest compressions and ventilations, the timing, frequency and/or duration may be varied depending on the particular treatment. For example, chest compressions may occur during the entire systole phase, or only during a portion of it. Further, chest compressions may occur every systole phase or during only certain systole phases. A similar scenario may occur with ventilations. The controller may use one or more sensory inputs, and a logic circuit utilizing an indicator or indicators of efficacy, to optimize the effect of synchronization on hemodynamics.

The system disclosed herein may be utilized with any therapy that may benefit from synchronization with residual myocardial mechanical function in apparently lifeless patients. Chest compression and decompression, abdominal counter-pulsation, ventilation, phasic limb-compression, myocardial electrical stimulation, intravascular fluid shifting, intravascular or intra-pericardial balloon inflation-deflation, application of transthoracic electromagnetic irradiation, among others. The controller logic circuit may vary the pattern (or protocol) of synchronization among multiple therapies so as to determine the optimal pattern with respect to increasing hemodynamics.

Myocardial electrical stimulation is, for example, external electrical shocks delivered through metal paddles or electrodes applied to the chest, or electrical signals applied directly to the heart from an internal pacemaker modified to synchronize myocardial electrical stimulations to, for example, myocardial wall function or detected pulsatile blood flow. Embodiments described herein may be used in accordance with the disclosure provided in U.S. Pat. No. 9,833,378, entitled "NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION," which is hereby incorporated by reference herein in its entirety.

FIG. 1A is a schematic diagram of an exemplary embodiment of a medical system 100 including a medical device 114 (e.g., a patient monitor, defibrillator-monitor, or defibrillator) and an automated chest compressor (chest compressor) 108. In this embodiment, the medical device 114 receives and processes signals obtained from electrocardiogram sensors/electrodes 103A, 103B (ECG sensors), which are attached to a patient 101. Optionally, additional sensors 107a-n may also be attached to other body parts of the patient 101 such as the patient's arms and legs (and include other types of sensors, such as motion sensors or accelerometers for measure chest depth/displacement during chest compressions). Additionally, or alternatively, these sensors 107a-n may be additional ECG electrodes or other sensors (e.g., capnography, pulse oximeter, blood pressure monitor, etc.). Hemodynamic activity sensors 104A to 104n (hereinafter, collectively referred to as hemodynamic sensor(s) 104) obtain information related to hemodynamic activity (e.g., blood circulation) within the patient 101. Similarly, one or more hemodynamic sensors may be placed on various parts of the patient's body to measure one or more of a blood pressure of the patient, $CO_2$ of the patient, SPO2 of the patient, an ETCO2 value, or other measure of blood flow of the patient.

The additional ECG sensors 103C to 103n are typically not tethered or connected to the band/belt of the automated chest compressor 108 so as to avoid creating artifacts in the measured ECG signals that might hinder detections of QRS complexes or the determination of the QRS fiducial point (discussed in detail below). In general, the ECG sensors 103A to 103n measure the electrical activity of the heart by measuring electrical charges associated with the depolarizing and repolarizing during each heartbeat of the patient 101. The hemodynamic sensors 104 are attached to the patient 101 in order to measure hemodynamic activity (e.g., blood flow, myocardial pump activity, or myocardial mechanical activity at regions to which the hemodynamic sensors are attached). Taking inputs together from the ECG sensors 103a to 103n and the hemodynamic sensor 104, at least one processor (e.g., reference numeral 123 in FIG. 2) may be configured to determine whether the patient 101 is suffering from a cardiac condition (e.g., asystole, unconscious hypotension with an organized ECG, p-PEA, PEA, ventricular fibrillation, and ventricular tachycardia).

The medical device 114 may be, for example, but not limited to, one or more of, a patient monitor, a defibrillator, a mechanical chest compression device (e.g., an automated chest compression device, a belt-based chest compression device, a piston-based chest compression device (illustrated in FIG. 1B), a hand-held chest compression device for mechanically assisted chest compressions, an active compression-decompression device, or combinations thereof), a ventilator, an intravenous cooling device, and/or combinations thereof. The medical device 114 may be a wearable device. The medical device 114 may include or be coupled to a patient monitor. The ventilator may be a mechanical ventilator. The mechanical ventilator may be a portable, battery-powered ventilator. The intravenous cooling device may deliver cooling therapy and/or may sense a patient's temperature. The medical device 114 may provide, for example, but not limited to, one or more of electrical therapy (e.g., defibrillation, cardiac pacing, synchronized cardioversion, diaphragmatic stimulation, phrenic nerve stimulation, etc.), ventilation therapy, therapeutic cooling, temperature management therapy, invasive hemodynamic support therapy (e.g., extracorporeal membrane oxygenation (ECMO)), and/or combinations thereof.

As illustrated, the medical device 114 incorporates and/or couples (e.g., mechanically, electrically, and/or communicatively) to one or more sensors (e.g., ECG sensors 103C to 103$n$ and hemodynamic sensors 104. The sensors obtain patient parameters. The sensors may include, for example, but not be limited to, cardiac sensing electrodes, chest compression sensor(s), ventilation sensor(s), and/or one or more sensors capable of providing signals indicative of one or more of vital sign(s), electrocardiogram (ECG), blood pressure (e.g., invasive blood pressure (IBP), non-invasive blood pressure (NIBP)), heart rate, pulse oxygen level, respiration rate, heart sounds, lung sounds, respiration sounds, end tidal CO2, saturation of muscle oxygen (SMO2), arterial oxygen saturation (SpO2), cerebral blood flow, electroencephalogram (EEG) signals, brain oxygen level, tissue pH, tissue oxygenation, tissue fluid levels, and/or one or more sensors capable of providing signals indicative of one or more parameters determined via ultrasound, near-infrared reflectance spectroscopy, pneumography, cardiography, ocular impedance, spirometry, tonometry, plethysmography, eye tracking, chest compression parameters (e.g., compression depth, compression rate, compression release, release velocity, distance of active release for active compression-decompression, etc.), ventilation parameters, respiratory parameters, drug delivery parameters, fluid delivery parameters, transthoracic impedance, blood sampling, venous pressure monitoring (e.g., CVP), temperature, pulse oximetry, non-invasive hemoglobin parameters, and/or combinations thereof. In various implementations, the one or more sensors may also provide therapy.

In a typical implementation, one or more rescuers (e.g., reference numeral 105 in FIG. 2) provide treatment and/or care to the patient 101. The treatment may include, for example, assessing the patient's condition, treatment of wounds, administration of medications, performance of intubation for ventilation purposes, or performance of CPR, to list a few examples. In the illustrated example, the patient 101 is positioned on the support and housing 110 of the automated chest compressor 108, such as the AutoPulse Resuscitation System provided by ZOLL Medical Corporation of Chelmsford, Mass. The AutoPulse Resuscitation System is a battery powered, belt-based, automated chest compressor capable of providing high-quality automated CPR to victims of cardiac arrest. In operation, the belt is positioned around the thorax of the patient, and through the automated constriction of the belt, the AutoPulse Resuscitation System provides chest compressions to the patient 101 by constriction of the belt around the patient thorax in a manner that improves blood flow to the heart, brain, and other body extremities.

In one example, the medical device 114 is a defibrillator or monitor-defibrillator capable of providing ECG shock analysis and defibrillation to the patient. Examples of such monitor-defibrillators include R-SERIES or X-SERIES manufactured by ZOLL Medical Corporation of Chelmsford, Mass. Likewise, other examples of medical device 114 could include the M-SERIES, E-SERIES, or Propaq MD, also manufactured by ZOLL Medical Corporation of Chelmsford, Mass. In yet another alternative embodiment, the medical device 114 may also be an automated external defibrillator (AED) such as the AED PLUS or AED PRO, both of which are manufactured by ZOLL Medical Corporation.

Electrode pads 102A, 102B, which include the electrocardiogram (ECG) sensors 103A, 103B, respectively are attached to the patient 101. Proper placement of the electrode pads 102A, 102B on the patient 101 is important to ensure the effectiveness of the therapy. In adults, one electrode pad is typically placed on the patient's right chest above their right nipple and the second electrode pad is typically placed on the left lateral side of the patient opposite placement of the first electrode pad. In pediatric patients, who are comparatively lighter in weight than adults, one electrode pad is typically placed on the front right chest wall and the second electrode pad is typically placed on the back of the thorax.

In a typical implementation, the medical device 114 further includes an input/output interface such as a touchscreen visual display 116 that provides a visual display of the patient parameters, feedback related to resuscitation, and/or enables user input by the rescuer(s). Additionally, the medical device 114 may include one or more speakers 118 to provide audible feedback (e.g. alarms, prompts, alerts). The medical device 114 may include other methods of inputs such as programmable soft keys, buttons, or dials, for example. In yet another alternative embodiment, the medical device 114 may include a microphone to receive voice commands from the rescuer.

In various implementations, the one or more hemodynamic sensors 104 are communicatively coupled to the medical device 114 and placed on the patient. The hemodynamic sensor(s) may provide a measure of the flow of blood within tissues of the patient's body. In an example in which the medical device is the R-SERIES or X-SERIES manufactured by ZOLL Medical Corporation, the hemodynamic sensor 104 may be an invasive blood pressure (IBP) monitor, which may be inserted into one or more of the patient's arteries (e.g., the Aorta, Brachial Artery, Femoral Artery, Pulmonary Artery, or Radial Artery) to provide a direct measurement of arterial pressure of the patient. Such invasive sensors allow direct and continuous monitoring of the patient's blood pressure beat-by-beat, and this method enables precise measurements of blood pressure, even at relatively low blood pressures.

A dynamic pressure sensor may be used to detect pulsatile flow by sensing the oxygen content in a peripheral vein. Similarly, a pulse oximetry sensor may also be used to detect the oxygen content in a blood vessel in, for example, the toes, fingers or ear lobes. The oxygen content is directly related to the flow of blood and may be used to determine when to initiate and terminate CPR and mechanical or electrical cardiac stimulation. For example, if the pulse oximetry sensor detects pulsatile flow and an oxygen content above a threshold, the system may reduce the force of chest compressions applied by the automated chest compression or terminate chest compressions. Similarly, if the pulse oximetry sensor detects no pulsatile flow or an oxygen level falling below a threshold, the system may initiate manual chest compressor or electrical cardiac stimulation. The system may adjust various parameters of phasic therapies based on trends in the sensed oxygen status. While the pulse oximeter's primary purpose is to measure oxygen saturation of the patient, pulse oximeters are often also able to determine heart rate and provide an indication of perfusion through the body via such measurements.

To sense myocardial wall function, a variety of noninvasive devices and technologies may be used. For example, Doppler ultrasonography may be implemented. Doppler ultrasound uses the Doppler shift of ultrasonic waves produced from a transducer and reflected from body tissues to quantify the blood flow in peripheral vessels. This may be applied with the transducer positioned on the neck for providing a measure of carotid flow, the groin for measuring femoral flow, or a transthoracic or intraesophageal transducer for measuring aortic flow. A Doppler probe may also be placed at the cardiac point of a maximum impulse to detect movement of blood within the myocardium. An array of Doppler probes may be used to determine the vector of residual myocardial mechanical function and align chest compression and relation with that vector.

The data regarding pulses in peripheral blood vessels may be utilized to estimate residual myocardial mechanical function, such as the cardiac ejection phase, based on stored information regarding the delay between the myocardial mechanical function and pulse pressure or pulsatile flow in the peripheral blood vessel.

A further sensing technique that may be used is plethysmography. Plethysmography may be applied by measuring changes in the transthoracic AC electrical impedance with heart motion. A further technique that may be used is phonocardiography, which records the acoustical energy detected by a stethoscope over the heart. Still, a further technique that may be used is echocardiography. With echocardiography, ultrasound imaging of the heart, left ventricular ejection can be quantified. In some cases, echocardiograph detection of heart function may be combined with ECG. Also, sensitivity may be improved through the use of intravenously injected microbubbles or other ultrasound enhancing technologies.

It may be optimal to combine a number of these detection systems so as to increase the sensitivity and specificity of detecting residual myocardial mechanical function. Additionally, it may be optimal to incorporate a logic circuit which compares combinations of sensing technologies to an indicator of actual cardiac output, such as end-tidal carbon dioxide or aortic flow. In this manner, the present system could determine which combination of sensing technologies are most predictive of improvements derived from synchronization.

Additionally, the logic circuit of the present system might be capable of varying the synchronized therapeutics against indicators of actual cardiac output so as to determine which pattern of synchronized therapy is most effective. It may vary synchronization within one therapeutic device or multiple therapeutic devices so as to identify the optimal pattern.

In some embodiment, it may be optimal to combine a number of these detection systems so as to increase the sensitivity and specificity of detecting residual myocardial mechanical function. Additionally, it may be optimal for the processor (123 in FIG. 2) to implement software and/or the logic circuit to compare combinations of sensing technologies to determine which combination is most sensitive, accurate, or predictive of improvements derived from synchronization of chest compressions.

In yet another embodiment, a radio frequency (RF) sensor may be used to measure the patient's blood pressure. In operation, a radio frequency wave is directed toward a patient's artery and part of the reflected radio waves are received by a detector. The detected energy is then processed using one or more signal processing algorithms to extract information directed to the type, location, size, and relative movement of the tissues and organs and consequently blood flow. One example is of an RF sensor is the μCor non-invasive fluid status monitor by Kyma Medical Technologies of Tel Aviv, Israel or the LifeWave Cardio Connect sensor by LifeWave Biomedical, Inc. of Los Altos, CA.

In still another alternative example, evidence of hemodynamic flow (e.g., patient's pulse) may be determined and inputted by the rescuer. For example, the rescuer may check the carotid artery in the patient's neck or the radial artery in the patient wrist or may use a stethoscope to listen for sounds of the heart and/or blood vessels that are indicative of hemodynamic flow. In this embodiment, the rescuer would manually input the hemodynamic status of the patient into the medical device 114 via an input, such as a touch-screen interface displayed on the display 116 of the medical device 114.

In the illustrated embodiment, the ECG and hemodynamic sensor(s) are connected to the medical device 114 via a wired connection 106. In an alternative embodiment, however, the connection may be wireless (e.g., wireless communication 115 or 117). Likewise, in some embodiments, the automated chest compressor 108 and/or the ECG sensors 103A to 103n and hemodynamic sensors 104 may be able to communicate wirelessly with an external computing device 112. Such wireless communication may be accomplished via Bluetooth, BLE (i.e., Bluetooth Low Energy), near field communication (NFC), 3G/4G/5G wireless networks, or Wi-Fi networks, to list a few examples.

The external computing device 112 may be a tablet or other mobile computing devices such as smartphones, wearable devices (e.g., smart watches or smart glasses), laptop computers, personal digital assistants. Additionally, the external computing device 112 may include a touchscreen interface, as illustrated, or include alternative means of input such as a keyboard and mouse. In yet another embodiment, the external computing device may utilize voice commands as input. While the illustrated example shows the external computing device 112 as being at the scene with the patient 101, the external computing device may be a personal computer and located remotely and operated by a remote user (e.g., a doctor at a hospital).

Figure 1B:
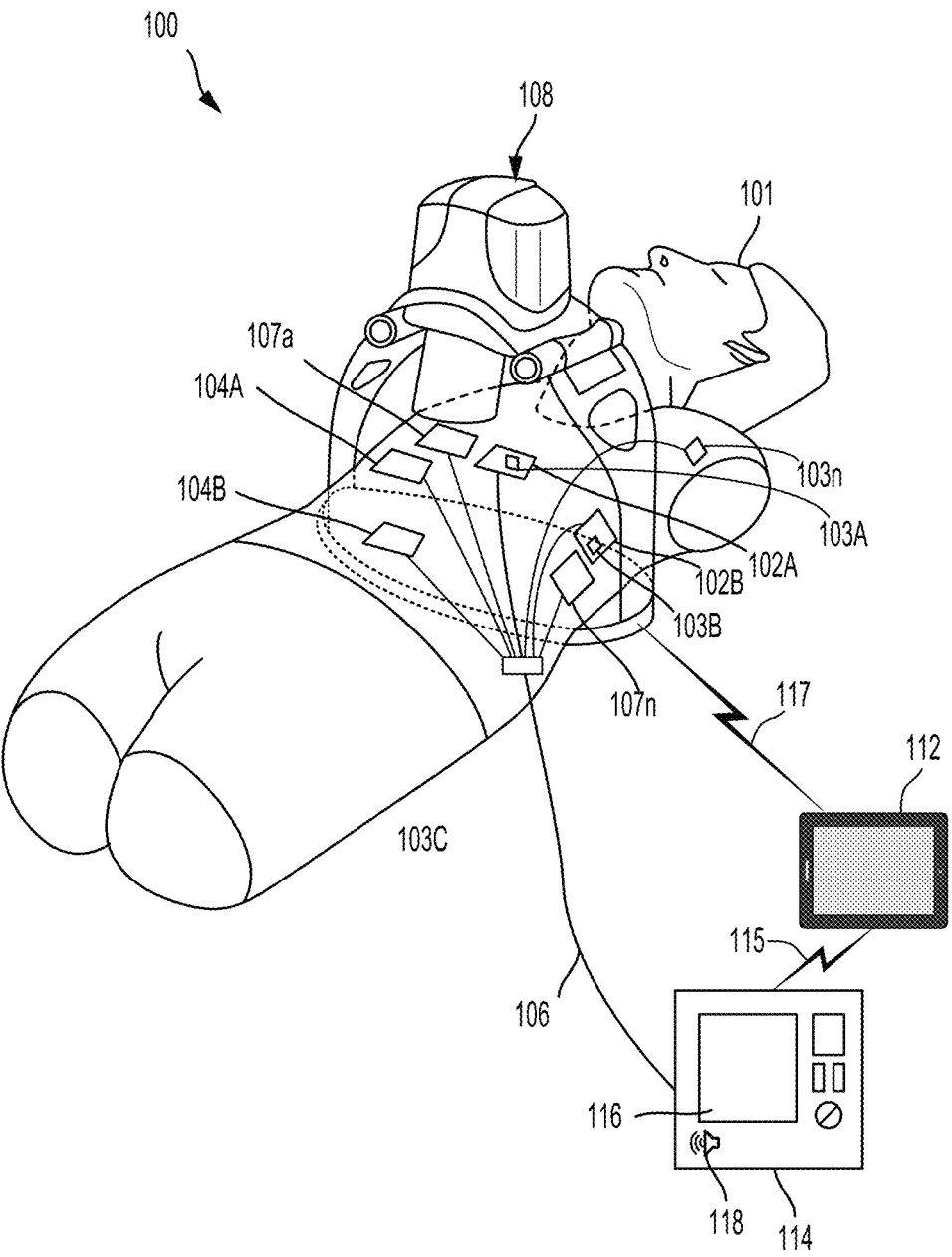
FIG. 1B is a schematic diagram of an illustrative embodiment of a medical system including a medical device and an alternative automated chest compression device.

FIG. 1B is a schematic diagram of a medical system 100 including a medical device 114 and a piston-based automated chest compressor 108. In general, the system and operation of FIG. 1B are similar to the embodiment described with respect to FIG. 1A. In this embodiment, however, the automated chest compressor 108 is a piston-based chest compressor such as the Lucas chest compression device stem by Physio-Control Corporation of Redmond, WA With the LUCAS system, the piston is rigidly locked in place relative to the back plate via rigid legs. A piston and piston driving mechanism are attached to support arms. In operation, the piston is installed such that the piston contacts the chest of the patient and compressions are generated via the vertical motion of the piston which forces compression of the patient's chest.

Figure 2:
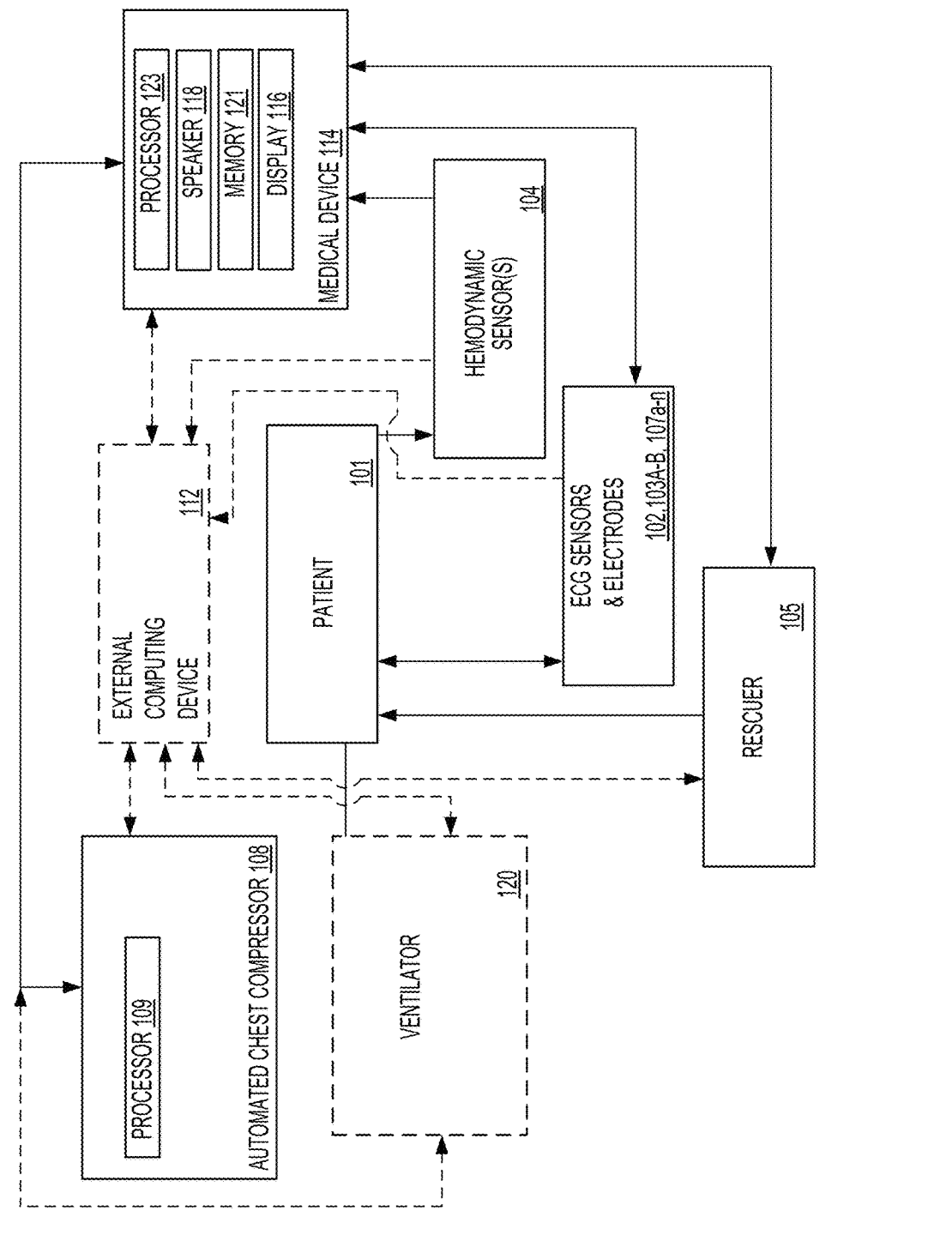
FIG. 2 is a block diagram illustrating the relationship between the components of the systems described in FIGS. 1A and 1B, according to one embodiment.

FIG. 2 is a block diagram illustrating the relationship between the components of the medical systems 100 described in FIGS. 1A and 1B, according to one embodiment. This figure also illustrates a rescuer 105, an optional ventilator 120, and the components of the medical device 114. These components include one or more processors 123 and memory 121, a speaker 118, and a display 116. In one embodiment, the at least one processor 123 comprises a first processor configured to process the ECG signals corresponding to the ECG of the heart and a second processor configured to control the chest compressor to provide the chest compressions to the patient 101. In another embodiment, the at least one processor 123 comprises a single processor configured to process the ECG signals corresponding to the ECG of the heart and control the chest compressor to provide the chest compressions to the patient.

In yet another embodiment, the at least one processor 123 comprises a first processor and a second processor configured to process the ECG signals corresponding to the ECG of the heart and control the chest compressor to provide the chest compressions to the patient 101. In still another embodiment, the at least one processor 123 comprises a first processor configured to process the ECG signals corresponding to the ECG of the heart and control the chest compressor to provide the chest compressions. Additionally, the at least one processor 123 comprises a second processor configured to control the chest compressor to provide the chest compressions to the patient.

In one example the optional ventilator 120 may be a portable mechanical ventilator that provides mechanical ventilation to a patient. An example may include the EMV+, AEV, Eagle II, and/or Eagle II MRI, all of which are manufactured by ZOLL Medical Corporation. Alternatively, the ventilator could be a BVM (bag-valve-mask) device that requires manual operation of the bag to provide ventilations to the patient 101.

Exemplary components of the medical device 114 include one or more processors 123, memory 121, which may include hard disk drive (either solid state magnetic based), RAM, or flash memory for example. The display 116 may be a touch screen interface that enables user input to be entered on the display 116. Alternative embodiments may use other display technology, such as light emitting diodes (LED), liquid crystal display (LCD) or organic light emitting diodes (flexible OLED), to list a few examples.

Additionally, the medical device 114 may further include one or more speakers 118 capable of providing audible feedback. For example, the speaker 118 may provide an alarm in response to a deteriorating heartbeat, deteriorating ventilations, or deteriorating end tidal CO2. The speaker may also provide verbal instructions for the rescuer 105 to carry out one or more shock therapy protocols.

Figure 3:
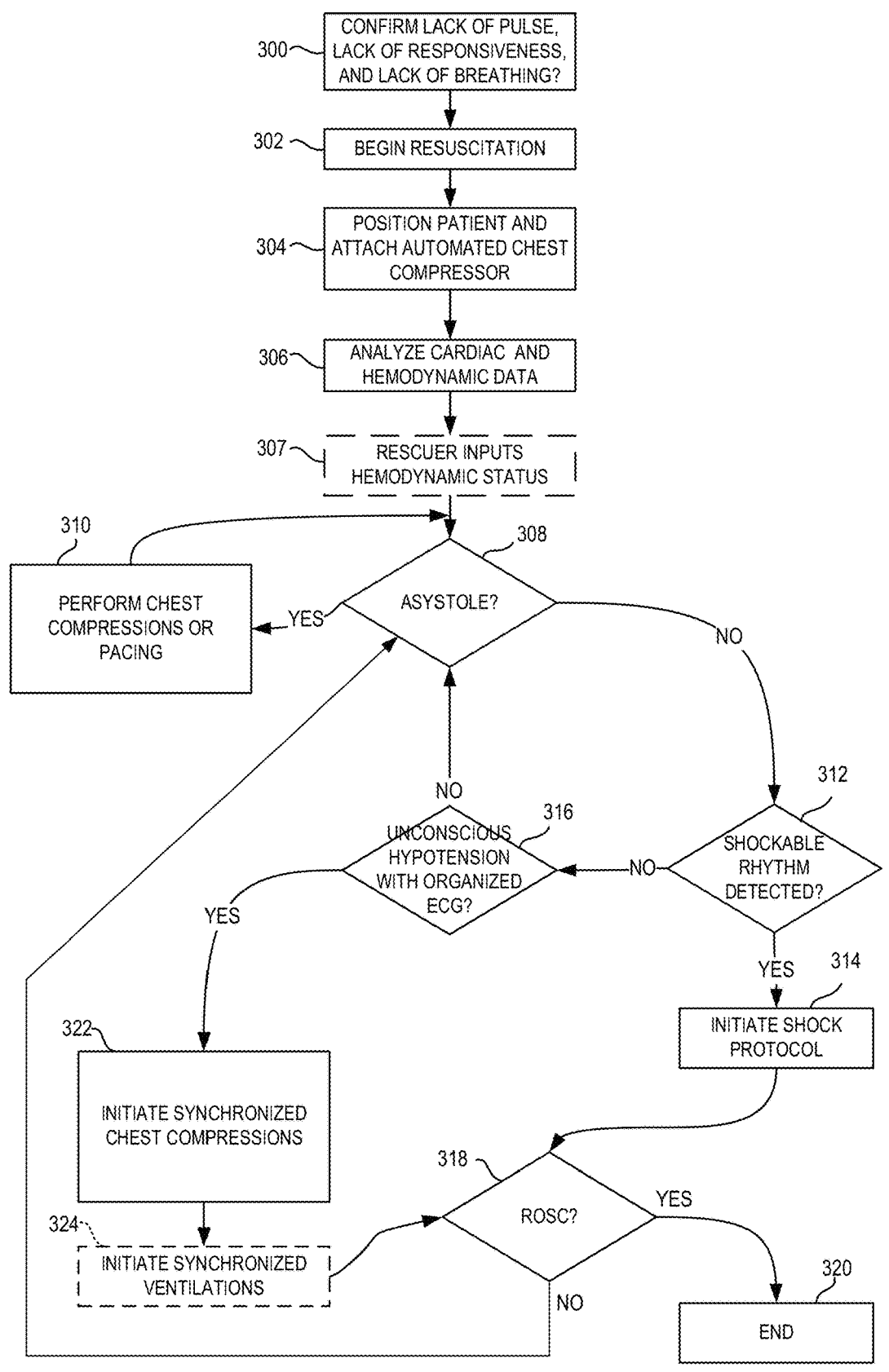
FIG. 3 is a flow chart illustrating steps for implementing the medical system of the present disclosure, according to one embodiment.

FIG. 3 is a flow chart illustrating steps for implementing an exemplary method of treating a patient by the medical system 100 comprising administering chest compressions that are synchronized with the intrinsic cardiac electrical activity (i.e., heartbeats) of the patient. Part or all of such a treatment method may be implemented in one or more algorithms to aid a rescuer in providing synchronized chest compressions when it is determined that the patient is suffering from unconscious hypotension yet still maintains an organized ECG.

In the first step 300, the rescuer 105 checks the patient and confirms a lack of pulse, responsiveness, and breathing. This step may include the rescuer's initial assessment of the patient's condition as well as the process of manually examining the patient to identify any injuries or other symptoms. In the next step 302, the rescuer 105 begins an exemplary resuscitation protocol, an example of which is illustratively provided below in the following steps.

Next, in step 304, the rescuer 105 positions the patient 101 so that an automated chest compressor 108 may be properly coupled to the patient 101. This step typically involves placing the patient 101 on a platform or support structure of the automated chest compressor. In the case of a belt-based chest compression device, the rescuer places the straps (or belts) of the automated chest compressor 108 around the chest of the patient 101. In examples of the treatment method that utilize a piston-based automated chest compressor, the patient is placed on a backboard and the piston and piston driving mechanism are positioned so as to apply compressions to the patient's sternum.

Additionally, the rescuer 105 also attaches electrode pads 102A, 102B, which include ECG sensors 103A, 103B, and one or more hemodynamic sensors 104 to the patient. These ECG sensors 103A, 103B enable the medical device 114 to acquire and analyze cardiac data in the form of electrical activity (e.g., ECG waveforms/ECG data) and the hemodynamic sensors 104 provide an indication of blood flow throughout the patient's body. In a typical implementation, the medical device 114 may perform a sensor validation procedure to ensure that the ECG 103A to 103n and hemodynamic sensors 104 are operating properly and that the received cardiac and hemodynamic data is accurate.

The processor 123 of the medical device 114 then analyzes the cardiac and hemodynamic data generated by the ECG sensors 103A, 103B and hemodynamic sensor 104, respectively, in step 306. This analysis typically includes a calculation of the patient's intrinsic electrical and mechanical activity (e.g., the patient's blood pressure and/or intrinsic heart rate, if present). A typical heart rate for a healthy adult is usually in the range of 60-80 beats per minute. A person's intrinsic heart rate is typically dependent on the patient's age, gender, and fitness level. Older patients who might have concomitant heart disease may be taking certain medications that artificially lowers their intrinsic heart rate.

In certain examples, in optional step 307, the rescuer 105 may input the hemodynamic status of the patient. The option to allow the rescuer to input patient hemodynamic status at this step may be desirable when the system cannot obtain hemodynamic data, for example, when a hemodynamic sensor is not available or not working properly (e.g., failed validation). In such exemplary methods and systems, the rescuer 105 may manually check for a pulse and then enter the information into the medical device 114. In one example, the display 116 of the medical device 114 is a touchscreen that displays the information and is configured to allow the rescuer to interactive with the touchscreen of the display to manipulate and/or analyze the displayed information. Additionally, the medical device 114 may implement one or more soft keys that enable user input. For example, a plurality of soft keys or buttons are positioned adjacent to the display 116 of the medical device 114 and the first key or button is pressed if the rescuer has detected a heartbeat of the patient and the second button is pressed if the rescuer has not detected a heartbeat of the patient 101.

In some embodiments, the user input of the hemodynamic status may act as an override of any determination made by the medical device 114. In embodiments, the rescuer 105 may want to provide the input of hemodynamic flow directly to the medical device 114. For example, the hemodynamic sensor(s) may be malfunctioning or may be taking a longer than desirable time to provide conclusive hemodynamic information to the medical device 114. In such cases, the rescuer can provide a direct manual input of the state of the hemodynamics of the patient 101. In another embodiment, the rescuer 105 may not utilize a medical system 100 with hemodynamic sensors. In such a scenario, the rescuer 105 inputs the hemodynamic status after determining the patient's hemodynamic status (e.g., check for a pulse at one or more arteries).

Next, in step 308, the processor 123 determines whether the patient is in asystole (i.e., the absence of any cardiac activity). If the patient is in asystole, then the medical device 114 transmits a signal to the automated chest compressor 108 to immediately begin delivering chest compressions and/or the medical device 114 may also provide pacing in step 310. While the embodiment is described with respect to an automated chest compressor 108, the chest compressions could be provided manually. In such a case, the medical device 114 displays one or more prompts that provide an indication of when to provide the chest compressions. Likewise, the medical device 114 may further provide visual and/or audible feedback to the rescuer to provide step-by-step instructions on how to adjust the chest compressions (e.g., faster, slower, deeper, shallower).

As will be detailed below, the chest compressor 108 utilizes an algorithm for the activation of synchronized chest compressions to provide one or more chest compression protocols. According to the treatment method disclosed herein, when the patient is in asystole, such as when no electrical or mechanical activity is present, the rescuer delivers chest compressions according to a standard chest compression protocol, such as a protocol according to the American Heart Association's current CPR guidelines.

Returning to step 308, if the patient 101 is not in asystole, then the processor 123 of the medical device 114 analyzes the received ECG waveform to determine if the waveform is indicative of a shockable cardiac rhythm (e.g., ventricular fibrillation or ventricular tachycardia) in step 312. If a shockable rhythm is detected in step 312, then the medical device 114 initiates a shock protocol in step 314 (e.g., applying one or more therapeutic shocks). Additionally, the medical device 114 will also check for ROSC (Return of Spontaneous Circulation) in subsequent step 318. In general, ROSC may be determined based on one or more of: a regular, organized heartbeat, consciousness of the patient, a palpable pulse of the patient, a measurable blood pressure, and unassisted breathing, for example. If the patient has achieved ROSC, then the treatment is discontinued in step 320. Additionally, in some embodiments, a patient may need supportive synchronized chest compressions post-ROSC. For example, in some cases, the PEA condition is found in cardiac arrest victims who have been defibrillated often following extended periods of fibrillation or asystole. The extended periods of fibrillation or asystole result in the myocardium being depleted of its energy stores, which results in its contractility being degraded causing a PEA condition. This is particularly the case when ROSC occurs as a direct result of electrical defibrillation.

If a shockable rhythm is not detected in step 312, then the processor 123 determines if the patient 101 is suffering from unconscious hypotension with an organized ECG (e.g., PEA) in step 316. Two conditions are determined at this step: 1) organized ECG, and 2) unconscious hypotension.

Determination of whether or not the ECG is organized may be determined via certain methods, for instance, such as: first detecting the R-waves (e.g. relevant descriptions provided by Pan J, Tompkins W. A real-time QRS detection algorithm. IEEE Trans Eng Biomed Eng. 1985; 32(3):230-236); then measuring ECG heart rate, morphologic and amplitude characteristics for at least three R-R intervals of the ECG; then performing statistical analysis and/or decision rule determination to determine variability of at least one of the above characteristics. If the variability for at least one of the characteristics is below a threshold, then the ECG may be considered "organized." Some examples of ECG heart rate characteristics include R-R interval, average heart rate over a predefined interval, and heart rate variability. Morphologic characteristics include QRS width, R-wave sharpness or other frequency domain analysis of the R-wave, Q-wave presence, P-wave presence. Amplitude characteristics include R-wave, P-wave, Q-wave, T-wave amplitudes. In one example, when the variability is less than 10%, then the ECG may be considered organized.

The patient condition of unconscious hypotension may be determined, for example, via a blood pressure sensor or SpO2 sensor. The blood pressure sensor may be an invasive blood pressure sensor or a non-invasive cuff-based oscillometric blood pressure sensor. In some examples, when mean arterial pressure (MAP) falls below 40 mmHg or SpO2 falls below 85%, the patient condition of unconscious hypotension may be satisfied. In general, a patient suffering from unconscious hypotension with an organized ECG or PEA will have a low blood pressure of 45/25 mmHg or lower (e.g., as low as 25/15 mmHg). Likewise, blood flow may be measured via Doppler ultrasonography may be implemented to determine unconscious hypotension. Doppler ultrasound uses the Doppler shift of ultrasonic waves produced from a transducer and reflected from body tissues to quantify the blood flow in peripheral vessels.

The condition of unconscious hypotension may be estimated by analysis of the ECG alone without additional blood pressure, blood flow or perfusion measurements. For instance, ECGs for patients suffering from unconscious hypotension with an organized ECG typically have common characteristics such as a repeatable R-wave; a lack of P and/or Q-waves; the amplitudes of the ECG may be reduced; and the ECG may have wider and more rounded characteristics as compared to normal sinus rhythm. Thus, detection of one or more of these ECG morphologic characteristics (or lack thereof in the case of the P and Q waves), without the need for a blood pressure measurement, may be sufficient to indicate a patient is suffering from unconscious hypotension with an organized ECG (e.g., PEA).

In some examples, for the cases of post-defibrillation shock, unconscious hypotension may be determined based solely on ECG heart rate. Following a defibrillation shock, a time period (e.g. 10, 20, 30 or 60 seconds) of ECG is analyzed. If the heart rate falls below 40 BPM in the interval post-shock defibrillation, then the patient may be determined to be in unconscious hypotension. In some examples, the heart rate may be measured as the average heart rate, the minimum, or the trend in the interval.

As detailed previously, unconscious hypotension with an organized ECG may also be referred to as PEA (or pseudo-PEA) in that the patient is unconscious (or unresponsive) and has low blood pressure, but the patient 101 may have an organized ECG. If the unconscious hypotension with an organized ECG is not detected or otherwise determined in step 316, then the medical device returns to step 308 to re-check for asystole. Alternatively, the medical device 114 may also display a prompt or warning/alert indicating alternative treatment options should be considered (e.g., reconsider CPR, checking for other trauma such as blood loss, checking for an airway blockage, or suggesting the rescuer may need to consider administration of drugs or medications).

In the present processes, the processor 123 is configured to identify a particular cardiac condition based on waveform characteristics. For example, as shown in FIGS. 5B and 5C, the QRS complex for sinus rhythm (FIG. 5B) may be markedly different from the QRS complex of a patient suffering from unconscious hypotension with an organized ECG (or PEA, EMD, p-PEA) as shown in FIG. 5C. Additionally, other measurable characteristics of the waveform are also different. Specifically, a patient suffering from unconscious hypotension with an organized ECG (or PEA, EMD, p-PEA) may have a reduced intrinsic heart rate (e.g., lower than 60-70 beats per minute). Conversely, a patient with ventricular fibrillation will exhibit rapid irregular contractions.

In another example, the ECG for a patient suffering from unconscious hypotension with an organized ECG (or PEA, EMD, p-PEA) may be missing P and/or Q-waves. Additionally, during PEA, the amplitudes of the ECG may be reduced. For example, the R-wave, which has the highest amplitude of all the waves, is typically between 0.3 and 0.5 millivolts compared to 1 millivolt for a normal sinus rhythm (e.g., generally ½ to ⅓ of the normal height during sinus rhythm). Lastly, during PEA, the QRS complex may have wider and more rounded characteristics as compared to normal sinus rhythm. For instance, a normal QRS complex typically may last 80 and 120 milliseconds and has relatively sharper peaks and valleys, as compared with the QRS complex of a patient suffering from unconscious hypotension with an organized ECG (or PEA, EMD, p-PEA). The QRS complexes of patients suffering from unconscious hypotension with an organized ECG (or PEA, EMD, p-PEA) may last more than 120 milliseconds and can be as long as 220 milliseconds, with the R-wave and S-wave having much more rounded peaks and valleys.

Returning to step 316, if the patient 101 is suffering from unconscious hypotension with an organized ECG, then the processor 123 initiates synchronized chest compressions in step 322 (further detailed below). While this step is illustrated as a discrete step, in an alternative embodiment, the medical device 114 may utilize this chest compression protocol whenever the medical device and chest compressor are operating. That is, for such an embodiment, the protocol would be implemented by default. Lastly, in optional step 324, ventilations from the ventilator 120 may be synchronized with the chest compressions from the automated chest compressor 108 to increase cardiac output. For example, in one embodiment inspiration and expiration may be synchronized to systole and diastole, respectively. In another example, the ventilations may occur after a predefined number of compressions.

Figure 4:
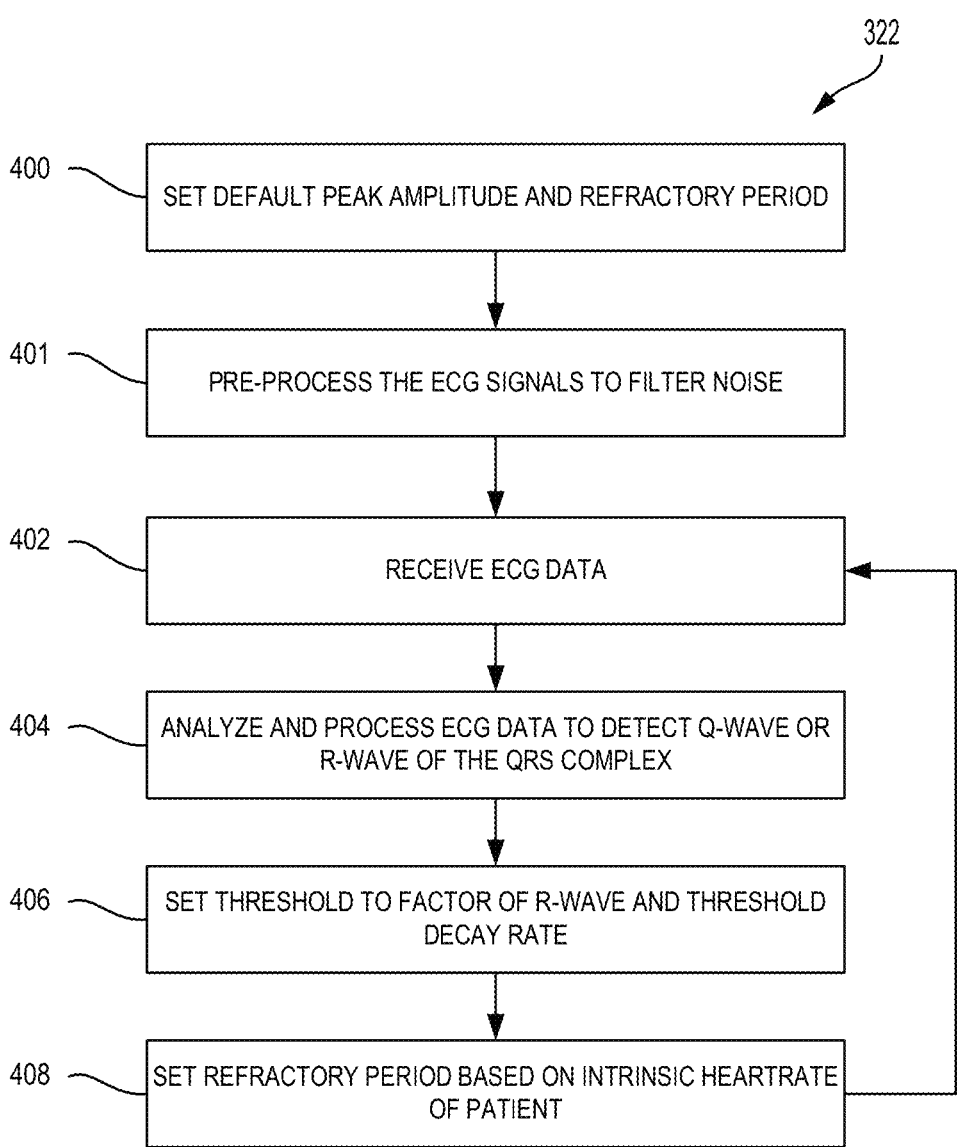
FIG. 4 is a flowchart illustrating steps for detecting QRS fiducial points in a QRS complex according to one embodiment.

FIG. 4 is a flowchart illustrating steps for determining fiducial points (e.g., 519, 519a, 519b in FIGS. 5D-5F) for initiating the synchronized chest compressions.

In this embodiment, the fiducial point is determined immediately upon detecting the presence of the R-wave. However, other embodiments may implement methods to identify other components (e.g., the P or Q-waves if present). The following steps may be performed so as to enable real-time detection of the R-waves of QRS complexes within ECG data for synchronization of chest compressions from the automated chest compressor 108 to the patient's intrinsic heartbeat. Specifically, the chest compressions may be synchronized to the peak of the R-wave of the patient's heartbeat. In order to synchronize a compression (e.g., the compression is timed such that the target depth of the compression will be reached within 150 milliseconds or less after the peak of the R-wave, or within 150 milliseconds or less before the peak of the R-wave), the medical device 114 must be able to identify the R-wave prior to the peak.

In more detail, a QRS complex for normal sinus rhythm is typically 80-100 milliseconds long. Whereas the QRS complex for a patient suffering from unconscious hypotension with an organized ECG (or similar conditions such as p-PEA or PEA) can be 120 milliseconds long or longer. Moreover, during conditions such as unconscious hypotension with an organized ECG, the length of time from the base of the R-wave to the peak can often be 90 milliseconds or more. Accordingly, systems and methods described herein may be able to detect a waveform feature such as a Q-wave, peak of an R-wave, an R-wave on the rising (or leading edge) slope. As such, the fiducial point (e.g., 519, 519a, 519b), and possibly the initiation of the synchronized compressions, may occur before the peak of the R-wave. Upon detection of the R-wave, the detection signal is sent from the medical device 114 to the chest compressor 108. However, in some scenarios, the detection signal may be delayed (timed) so as to coordinate the chest compression with a specific portion of the R-wave (e.g., just before the peak, with the peak, or just after the peak).

One exemplary algorithm for detecting QRS complexes is detailed by Pan, Jiapu and Willis J. Tompkins, "A Real-Time QRS Detection Algorithm." IEEE TRANSACTIONS ON BIOMEDICAL ENGINEERING, VOL. BME-32, NO. 3 (March 1985): 230-36; such an algorithm may be implemented in embodiments of the present disclosure.

In one specific example, in a first step 400, a default peak amplitude and refractory period are set. These default values are automatically adjusted later based on received and analyzed waveforms to more accurately set the peak amplitude threshold and refractory period. However, the values are initially set such that very few peaks, if any, within the ECG data are filtered out. As the processor 123 of the medical device 114 has not analyzed any ECG data or identified any QRS complexes, the processor 123 is not yet able to reliably identify QRS complexes and filter out unwanted noise. As mentioned previously, a waveform for someone suffering from PEA might have a peak amplitude that is only 30% (e.g., 0.3 millivolts) compared to a normal sinus waveform of a healthy patient. However, that peak value could be higher or lower. Thus, the default value needs to be low enough to detect weak signals. For example, the default value may be set as low as 0.15 millivolts, 0.10 millivolts, or even 0.05 millivolts. This ensures that weak R-waves are not inadvertently filtered out. The refractory period is based on the patient's heart rate. Until multiple QRS waveforms are received and analyzed, the processor 123 may be unable to calculate the patient's heart rate. A typical refractory period for a person with a heart rate of 60 beats per minute is 200 milliseconds. To ensure that signals are not ignored, the default refractory period may be as low as 10-20 milliseconds. In general, the refractory period is designed to help the processor filter out (i.e., ignore) peaks that might appear to be R-wave or QRS complexes, but cannot possibly be, due to the signals being detected to close to a previous heartbeat. Thus, a very short initial refractory period ensures very few signals are filtered out. This refractory period will be updated as more ECG data is analyzed and QRS complexes are identified.

In the next step 401, the processor pre-processes the ECG data to filter out high-frequency noise (e.g., muscle movements and power line noise between 50-60 Hertz). The processor 123 may perform the filtering or the medical device 114 may implement a digital signal processor, which is a processor optimized for signal processing. One embodiment of the present system implements a bandpass filter that has a passband between 5 and 15 Hertz. In step 402, the processor 123 of the medical device 114 receives ECG data measured by the ECG sensors 103A, 103B. The ECG sensors 103A, 103B detect electrical changes in voltage over time, which result from the repeated depolarization and repolarization of the myocardium during each heartbeat.

In step 404, the processor 123 analyzes and processes the ECG data to identify an R-wave of the initial QRS complex. Typical steps for detecting an R-wave in a QRS complex may include one or more of the following steps. Performing a differentiation to obtain information about the slope of the ECG waveform over time. The signal may then be squared or the absolute value is taken to allow for the detection of both positive and negative slopes. If the signal is squared, then the peak with the highest amplitude (which is generally the R-wave) to become even larger and more accentuated relative to other peaks. Lastly, integration may be performed to produce a resulting signal that includes information about both the slope and width of the QRS complex. In general, the end result of this processing is one peak that is significantly larger than the other peak, which is then identified as the R-wave by the medical device 114. The data may then be input to a threshold detector, which causes a detection signal to be generated if the threshold is exceeded (i.e., an R-wave of the QRS complex is considered to have been detected).

In the next step 406, the processor 123 sets a threshold value to a factor of the peak amplitude of the filtered ECG at the point of detection or at the maximum occurring peak of the R-wave (e.g., 60-70%) and also sets a threshold decay rate. This decay rate may be a linear rate of decline from the threshold value or another predetermined or variable decay function. This threshold decay rate minimizes false positives by filtering out noise and peaks below the threshold that mimic the characteristics of the QRS complex, but have values that are too small or too close in time after the detection to the R-wave to be the R-waves of subsequent heartbeats.

In step 408, the processor 123 sets the refractory period based on the intrinsic heart rate of the patient 101. The refractory period is simply a period in which signals that would otherwise be interpreted as artifacts are ignored. The signals are ignored because there is a period of time, for example between 200-240 milliseconds (for a heart rate of 60 beats per minute), in which subsequent heartbeats cannot physically occur. Thus, any detected peaks (e.g., noise, an artifact from chest compression, or T-waves) that might be mistaken as an R-wave during the refractory period are ignored. The refractory period helps filter out these potential false positives, which arrive too soon after a chest compression to possibly be another R-wave. Often these false positives are T-waves, which occur after the R-wave. The refractory period is automatically adjusted by the processor 123 based on the intrinsic heart rate of the patient. A faster heart rate results in a smaller refractory period, and a slower heart rate results in a longer refractory period.

The end result of such processing techniques is an output indicating a detected Q- or R-wave in the QRS complex. This signal processing may take place over a relatively short delay, for example between 5-15 milliseconds (as detailed in FIG. 5D), with a typical delay being approximately 8-10 milliseconds. Hence, there may be a short lag, from the acquisition of the ECG data from the ECG sensors 103A, 103B until the detection of the R-wave and QRS complex by the processor 123. However, the time from the processor(s) to the detection of the R-wave of a QRS complex until the signal is received by the chest compressor 108 is negligible. As discussed herein, it may be possible for the chest to be compressed almost immediately upon detection of the presence of the R-wave, without an appreciable time lag, particularly if the processing time for detection of the R-wave, determination of the fiducial point, and control of the chest compressions is minimal. Accordingly, in some instances, when the R-wave is detected on the rising edge, the synchronized chest compression may be applied before the peak of the R-wave, or shortly (e.g., within milliseconds) thereafter.

Figure 5A:
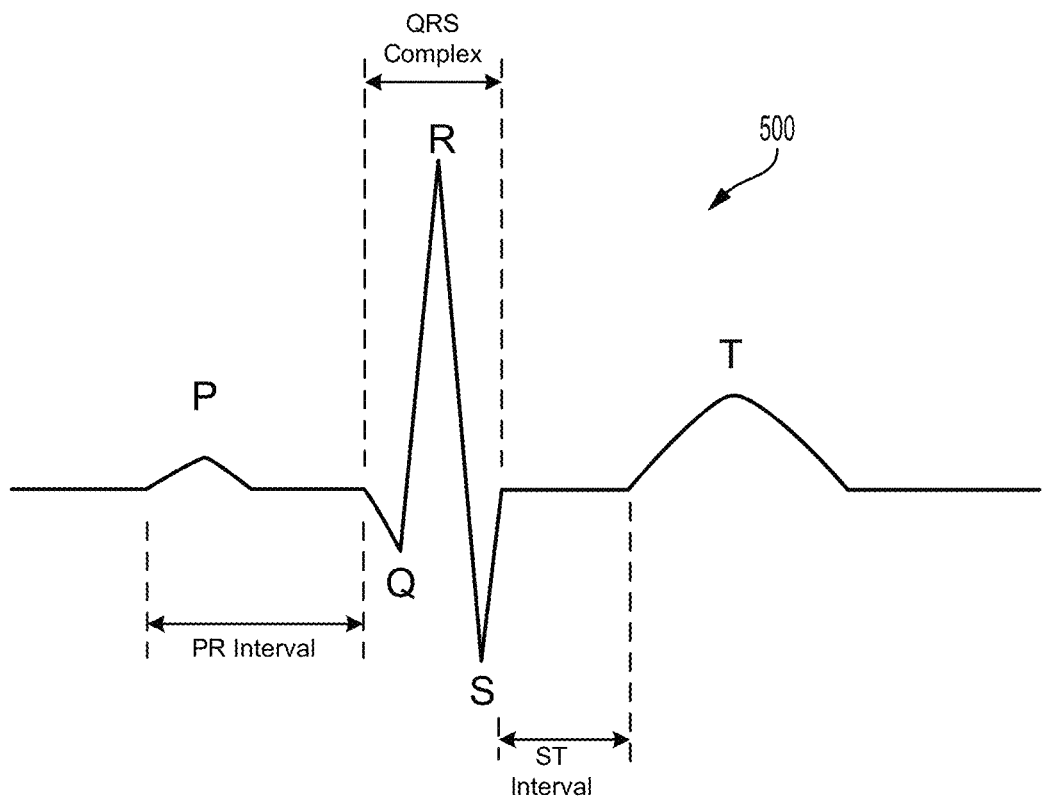
FIG. 5A illustrates an example of a QRS complex of an electrocardiogram (ECG) waveform for a patient with a normal sinus rhythm.
Figure 5B:
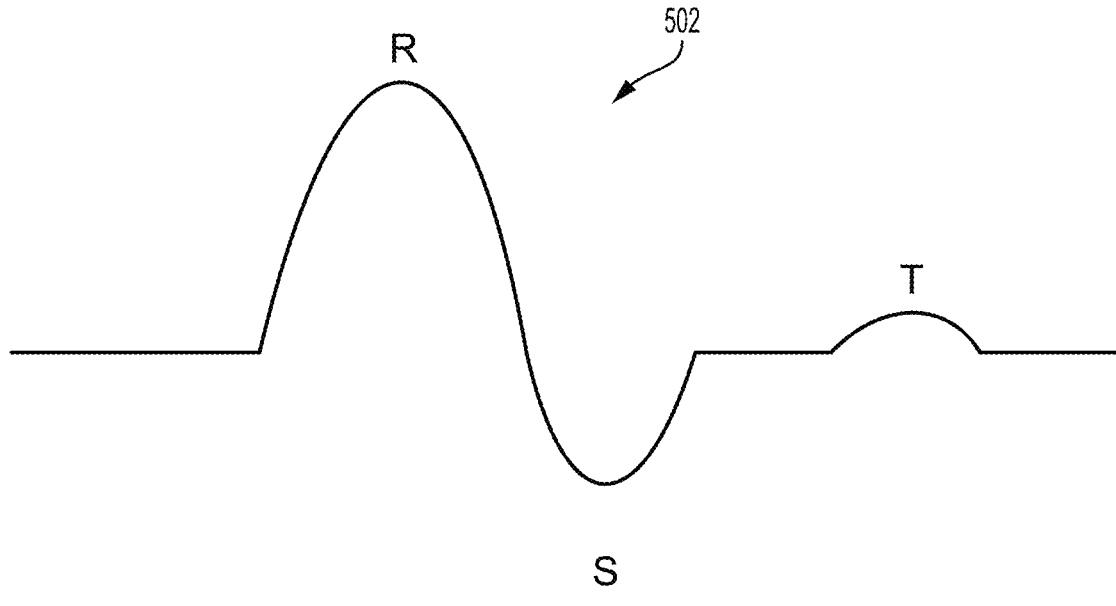
FIG. 5B illustrates an example of a QRS complex of an ECG waveform for a patient with unconscious hypotension with an organized ECG, which may have similar characteristics to pulseless electrical activity (PEA) or pseudo pulseless electrical activity.
Figure 5C:
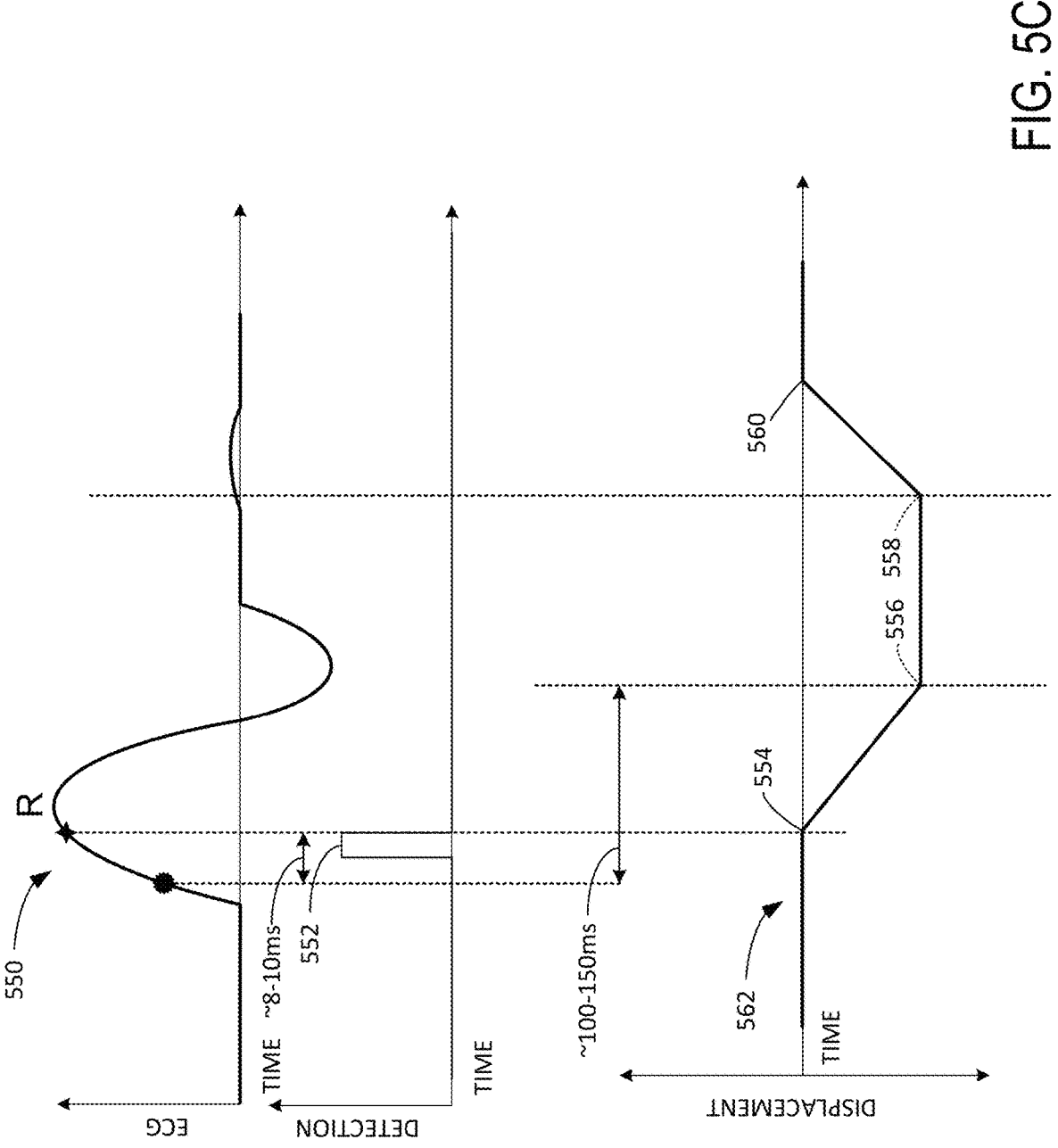
FIG. 5C illustrates a schematic diagram illustrating the timing and relationship between a detected QRS complex, the initiation of a chest compression, and the initiation of chest compression, in accordance with certain embodiments.

FIGS. 5A and 5B illustrate ECG waveforms, including QRS complexes for sinus rhythm and a PEA rhythm, respectively. These figures illustrate the differences between a typical sinus rhythm (FIG. 5A) and a rhythm associated with someone suffering from PEA (FIG. 5B). Additionally, a patient suffering from unconscious hypotension with an organized ECG may exhibit a heart rhythm similar to PEA (FIG. 5B).

An ECG waveform, which includes the QRS complex, for normal sinus rhythm 500 is depicted in FIG. 5A. The first wave is the P-wave, which represents atrial depolarization. The PR-interval is the period of time from the start of the P-wave to the start of the Q wave. The QRS-complex represents depolarization of the ventricles and contraction of the ventricular muscles. The ST-segment is the period of time that starts at the end of the S-wave and finishes at the start of the T-wave. And the T-wave represents ventricular repolarization. Typically, the QRS complex for sinus rhythm is approximately 80-100 milliseconds (however, it is also possible for the rhythm to be as long as 120 milliseconds). Additionally, as illustrated, the peaks and valleys of the waves in the QRS complex are characterized by relatively sharp peaks and valleys. While not illustrated, the amplitude the R-wave is approximately 1 millivolt.

FIG. 5B illustrates an example of an ECG waveform 502 for a patient suffering from unconscious hypotension with organized ECG, which may have similar characteristics as a PEA or p-PEA waveform. As compared to a normal sinus rhythm, the length of the time of the QRS complex is generally greater (e.g., 120-220 milliseconds). Additionally, the P-wave and Q-wave are oftentimes not present and the R and S-waves appear to be more rounded in a waveform form unconscious hypotension with organized ECG. This rounding is sometimes the result of electro-mechanical uncoupling between the electrical signals and corresponding mechanical contractions, which may occur during unconscious hypotension with organized ECG. While not specifically illustrated, the peak of the R-wave during unconscious hypotension with organized ECG may be between 0.3 and 0.5 millivolts (compared to 1 millivolt for sinus rhythm) in amplitude, which indicates a comparatively weak signal to a normal cardiac rhythm.

FIG. 5C is a schematic diagram illustrating the timing and relationship between a QRS complex 550 of an ECG signal, the detection signal 552 generated in response to the identification of the QRS complex 550, and a chest compression, which is shown via a displacement waveform 562. It should be appreciated that the illustrated QRS complex is only one representative example of a PEA waveform, and the PEA waveforms could look different in other examples.

As detailed in step 402 (of FIG. 5A) the medical device 114 receives ECG signals (data), which includes QRS complexes. Typically, there may be some small delay between the detection of the ECG signal by the sensors and the generation of the detection signal 552 due to the time it takes to receive and process the ECG by the medical device 114 (as detailed in FIG. 4, for example). In one implementation, the delay from the medical device 114 receiving the ECG data, the detection of the R-wave, and the generation of the detection signal 552 is approximately 8-10 milliseconds. Though, it can be appreciated that the delay between detection of the R-wave to initiation of the chest compression may vary; for example, the delay may be small such that the initiation of a chest compression is almost immediate from when the R-wave is detected. Alternatively, the delay may be longer in time.

In general, the detection signal 552 is an output signal generated by the medical device 114. This output signal is then transmitted to the chest compressor 108 to initiate the chest compression, which is shown by the chest compression displacement waveform 562. In this embodiment, the start of the downstroke (point 554, where the chest compression is initiated, to point 556, where the target compression depth is reached) begins just before the peak of the R-wave. For detecting when a target depth has been reached, the system may determine the target depth was reached upon the measured depth having reached or exceeded approximately 90% of the target depth (i.e., a 90% point). This 90% point operates as a tolerance and provides a small range for which the measured depth is determined to have reached the target depth regardless of whether the pre-specified target depth (e.g., 2.0-2.4 inches) is actually reached. In alternative embodiments, the target depth may be determined to have been reached when the actual measured depth has met or exceeded approximately 75%, 80%, 85%, 95%, 98%, 99% of the target depth. Illustrated by way of example, if the target depth is 2.0 inches, then the 90% point will be 1.8 inches (90% of 2.0 inches) and the target depth will be determined to have reached the target depth upon exceeding 1.8 inches.

Similarly, the start of the hold (point 556, from where the target compression depth is reached, to point 558, where the upstroke is initiated) and release/upstroke (point 558 where the upstroke is initiated to point 560 where the chest is released) are also illustrated. As will be detailed in detail below, in general, the chest compression downstroke (point 554 to point 556) is ideally synchronized with the R-wave (i.e., the ejection phase of the heartbeat) and the release (558 to 560) is similarly synchronized with diastole (i.e., the relaxation phase of the heartbeat). This synchronization of the chest compression to intrinsic phases of the heart provides a more efficient chest compression compared to unsynchronized chest compressions because each phase of the intrinsic heartbeat is augmented by the chest compression, resulting in increased forward blood flow.

Figure 5D:
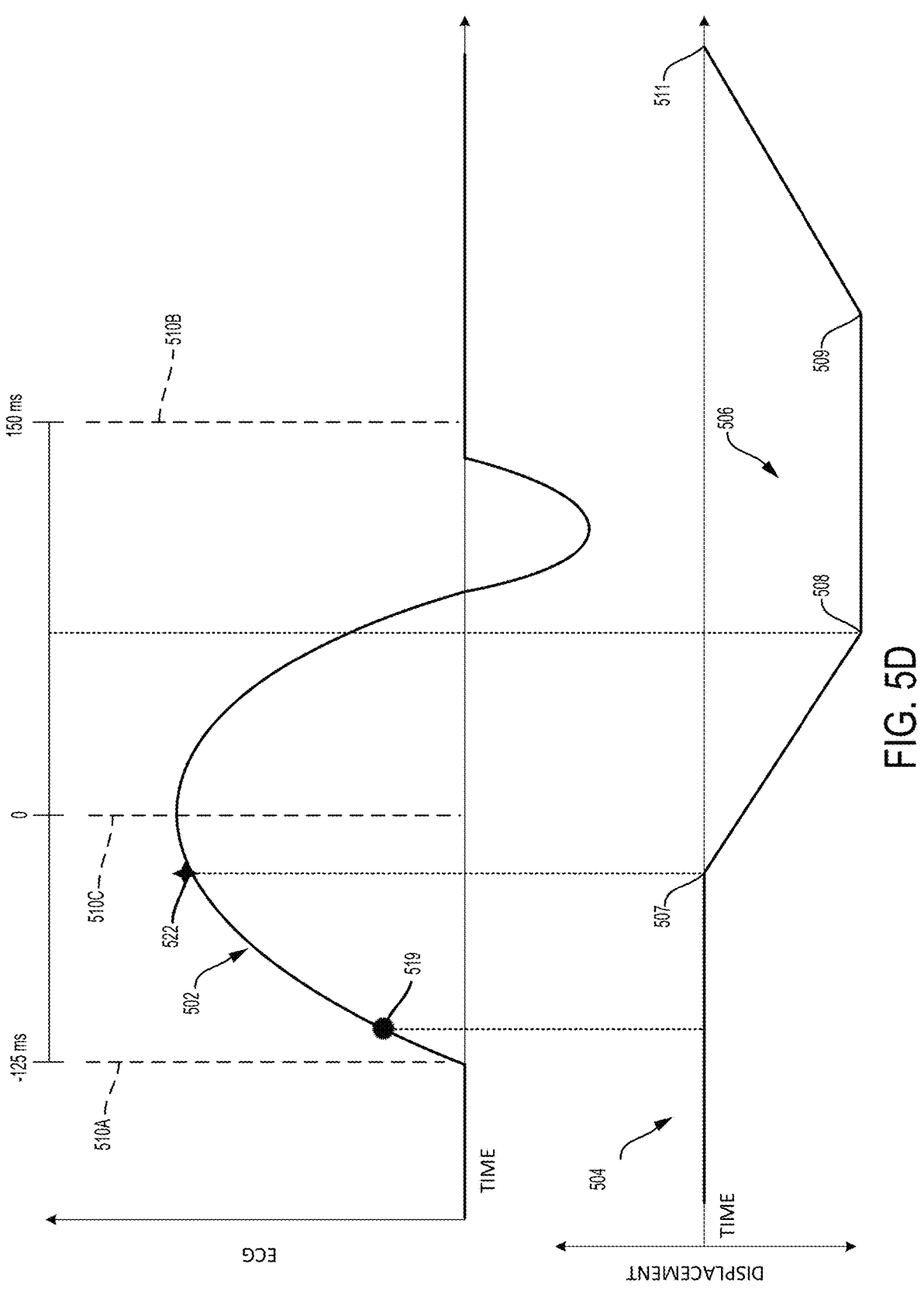
FIG. 5D illustrates an example schematic for synchronizing chest compressions to a QRS fiducial point that is determined prior to the peak of the R-wave according to one embodiment.

FIG. 5D is an illustrative embodiment showing one schematic representation of the QRS complex 502 for a patient suffering from unconscious hypotension with an organized ECG. FIG. 5D further illustrates a determined QRS fiducial point 519 on the leading edge of the R-wave, the detection signal 522 which is transmitted to the automated chest compressor 108, and the chest compression displacement waveform 504 showing a chest compression cycle 506 (e.g., downstroke, hold, release/upstroke).

More specifically, this figure illustrates an example of the timing and synchronization of a chest compression 520 after a determined QRS fiducial point 519. As illustrated, at point 519, the medical device 114 detects the R-wave. In this example, the detection signal 522 is delayed by the medical device 114 such that the generation of the signal does not occur until just before the peak of the R-wave 510C. The purpose of this delay is to synchronize the downstroke point 507 to point 508) of the chest compression with the peak of the R-wave 510C. Specifically, the initiation of the chest compression is timed such that the target depth of the compression will be reached within 150 milliseconds or less after the peak of the R-wave. In some exemplary embodiments, the target depth of the compression will be reached within 100 milliseconds or less after the peak of the R-wave. However, it can be appreciated that a delay between the QRS complex detection indicated by QRS fiducial point 519 and the detection signal 522 may not be necessary, as the chest compression may be initiated immediately upon detection of the QRS complex, given by the QRS fiducial point 519.

The peak of the R-wave 510C is referred to in FIG. 5D as a reference point "time zero." The start of the R-wave and the time window is at −125 milliseconds and is reference numeral 510A. The end of the time window, in which the chest compression should occur, is at approximately 150 milliseconds after the peak of the R-wave and is identified by reference numeral 510B. The peak of the R-wave 510C is the reference point for time zero because the effectiveness of the chest compression may decrease the farther away from the peak of the R-wave the chest compression occurs (in either direction). In certain embodiments, the peak of the R-wave may be determined as the highest point (voltage) recorded during the detected QRS complex. While one example of a QRS complex and time window are illustrated, the width of the QRS and time window may vary, e.g., from 120 milliseconds to 220 milliseconds (possibly as wide as 300 or 400 milliseconds in some scenarios). Accordingly, the time window would also be widened or shortened to correspond to the wider or narrower QRS complexes.

For some QRS detection schemes, the R-wave may be identified on the leading edge and prior to the occurrence of the peak of the R-wave, and may even be detected on the Q-wave, which immediately proceeds the R-wave. Upon detection of the QRS complex, the QRS fiducial point 519 may be determined. Then, upon determination of the QRS fiducial point, the processor 123 of the medical device 114 generates a detection signal that is transmitted to the automated chest compressor 108, which causes the chest compressor to apply a synchronized chest compression to the patient 101.

In the illustrated example, the chest compression is initiated prior to the peak of the R-wave. One benefit of initiating the chest compression prior to the peak of the R-wave is that the downstroke coincides with the heart's natural ejection phase to provide the most efficient chest compression to the patient. If the compression is initiated too soon or too late, then the compression may be less effective (as shown in FIG. 10B). In some embodiments, the QRS fiducial point and delay are user-programmable. In alternative embodiments, upon determination of the QRS fiducial point, the delay from the QRS fiducial point to when the target depth is reached may be: 120 milliseconds prior to the peak of the R-wave, 115 milliseconds prior to the peak of the R-wave, 110 milliseconds prior to the peak of the R-wave, 105 milliseconds prior to the peak of the R-wave, 100 milliseconds prior to the peak of the R-wave, 95 milliseconds prior to the peak of the R-wave, 90 milliseconds prior to the peak of the R-wave, 85 milliseconds prior to the peak of the R-wave, 80 milliseconds prior to the peak of the R-wave, 75 milliseconds prior to the peak of the R-wave, 60 milliseconds prior to the peak of the R-wave, 55 milliseconds prior to the peak of the R-wave, 50 milliseconds prior to the peak of the R-wave, 45 milliseconds prior to the peak of the R-wave, 40 milliseconds prior to the peak of the R-wave, 35 milliseconds prior to the peak of the R-wave, 30 milliseconds prior to the peak of the R-wave, 25 milliseconds prior to the peak of the R-wave, 20 milliseconds prior to the peak of the R-wave, 15 milliseconds prior to the peak of the R-wave, 10 milliseconds prior to the peak of the R-wave, 5 milliseconds prior to the peak of the R-wave, or synchronized to the peak of the R-wave.

Figure 5E:
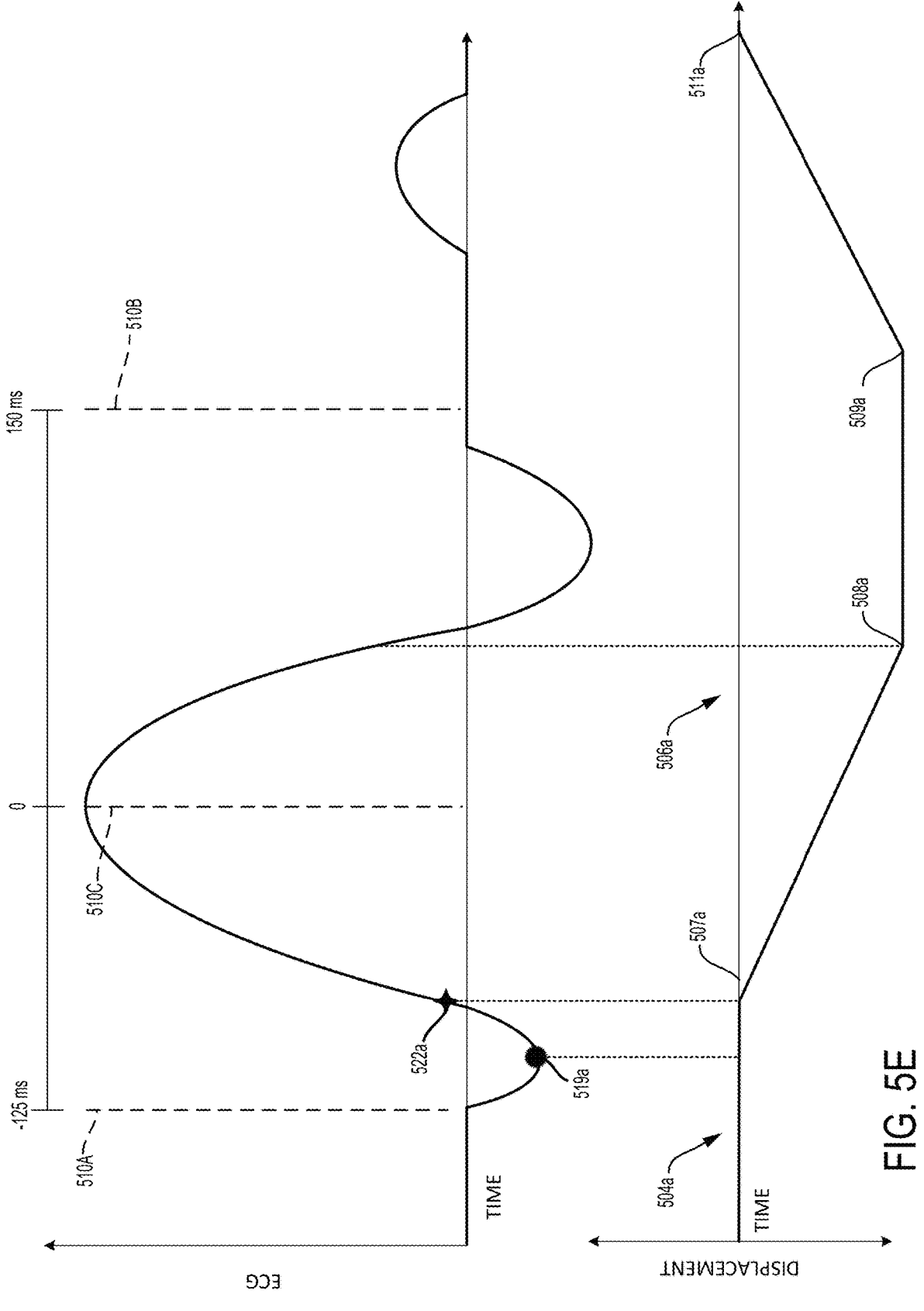
FIG. 5E illustrates an alternative example for synchronizing chest compressions to a QRS fiducial point that is determined during the Q-wave according to another embodiment.

FIG. 5E illustrates an example of synchronizing chest compressions to a QRS fiducial point 519a, which is based on detecting a Q-wave according to another embodiment.

Similar to FIG. 5D, the peak of the R-wave 510C is referred to in FIG. 5E as the reference point "time zero." The start of the time window is at the start of the Q-wave and −125 milliseconds (reference numeral 510A). And the end of the time window is at approximately 150 milliseconds and is identified by reference numeral 510B. Likewise, a displacement waveform 504a illustrates chest compression cycle 506a.

As described previously, some instances of unconscious hypotension with an organized ECG include patients with weak heartbeats. In these situations, the patients have organized electrical activity and some amount of mechanical myocardial function. Hence, in some scenarios, the patient 101 will have ECG waveforms that include P, Q, R, S, and T-waves (albeit weaker than in a healthy patient). Implementing, for example, the QRS detection process similar to the one described with respect to FIG. 4, it may be possible to detect a P-wave or Q-wave. Upon detection of the Q-wave, the at least one processor 123 is able to determine the QRS fiducial point 519a, which may be on the Q-wave or the R-wave.

In this example, the intentional delay is minimized such that the chest compression is timed to coincide with the R-wave and entire ejection phase of the patient's intrinsic heartbeat. Because the chest compression 506a was initiated well ahead of the peak of the R-wave, the medical device 114 may be able to adjust the shape of the chest compression.

For example, as illustrated, the slope of the downstroke (point 507a to point 508a) in this embodiment is much longer and not as steep compared to the embodiment of FIG. 5D. Likewise, the hold time (point 508a to point 509a) and release (509a to 511a) were lengthened. These changes to the compression parameters may be made to further synchronize the ejection and relaxation phases of a slower heartbeat, which may translate to more efficient chest compressions for the patient 101.

Like the previous embodiment, the delay from the QRS fiducial point 519a to initiation of chest compression 507a may be user-programmable. The delay from the peak of the R-wave until the target depth is reached may also be: 120 milliseconds prior to the peak of the R-wave, 115 milliseconds prior to the peak of the R-wave, 110 milliseconds prior to the peak of the R-wave, 105 milliseconds prior to the peak of the R-wave, 100 milliseconds prior to the peak of the R-wave, 95 milliseconds prior to the peak of the R-wave, 90 milliseconds prior to the peak of the R-wave, 85 milliseconds prior to the peak of the R-wave, 80 milliseconds prior to the peak of the R-wave, 75 milliseconds prior to the peak of the R-wave, 60 milliseconds prior to the peak of the R-wave, 55 milliseconds prior to the peak of the R-wave, 50 milliseconds prior to the peak of the R-wave, 45 milliseconds prior to the peak of the R-wave, 40 milliseconds prior to the peak of the R-wave, 35 milliseconds prior to the peak of the R-wave, 30 milliseconds prior to the peak of the R-wave, 25 milliseconds prior to the peak of the R-wave, 20 milliseconds prior to the peak of the R-wave, 15 milliseconds prior to the peak of the R-wave, 10 milliseconds prior to the peak of the R-wave, 5 milliseconds prior to the peak of the R-wave, or synchronized to the peak of the R-wave.

Figure 5F:
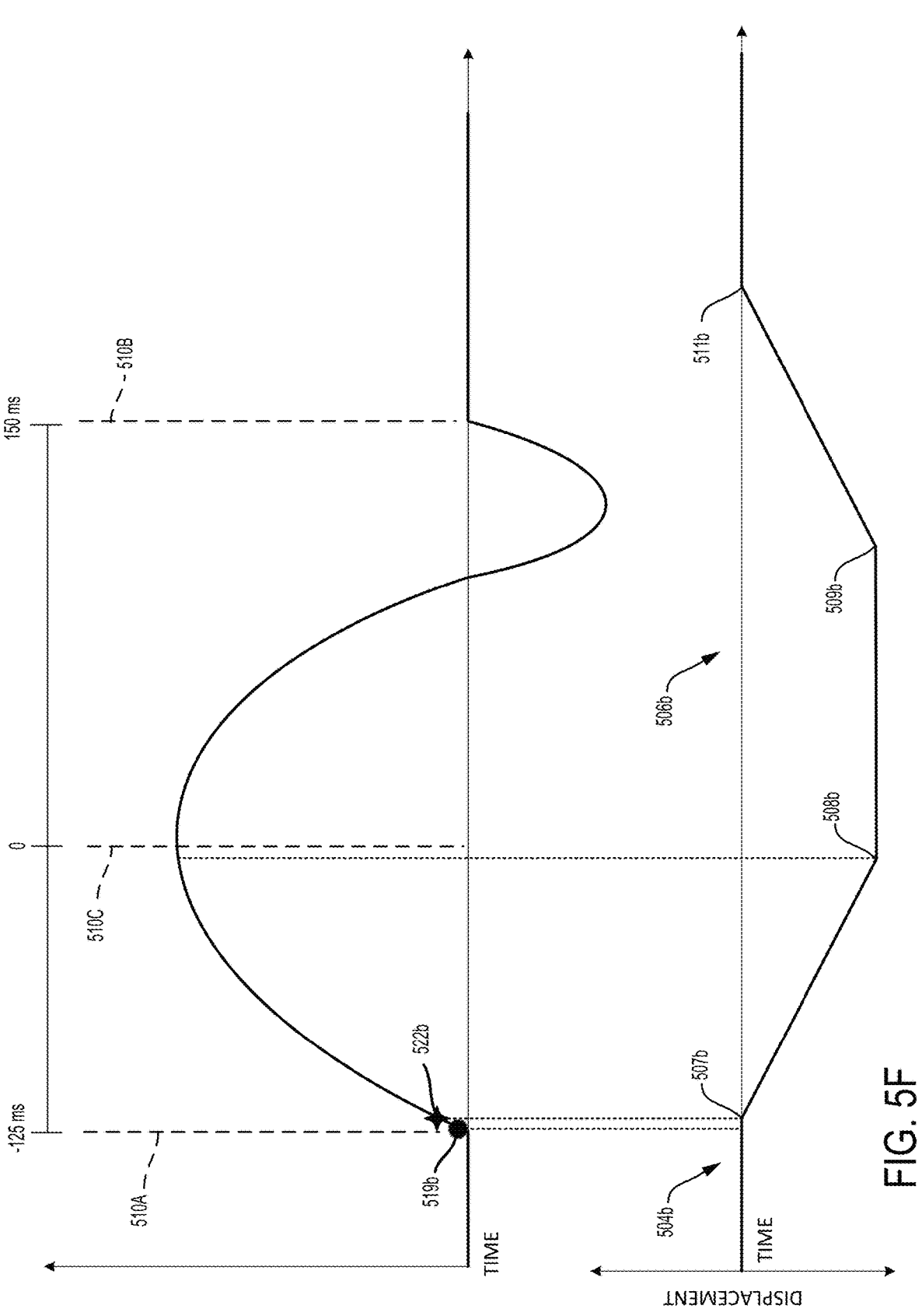
FIG. 5F illustrates an alternative example of synchronizing chest compressions after the peak of the R-wave according to another embodiment.

FIG. 5F is similar to FIG. 5D, but this figure illustrates an example for synchronizing the chest compression immediately after detection of a QRS complex. As illustrated, the peak of the R-wave 510C may be referred to in FIG. 5F as a reference point "time zero" (or time 0) and may be determined as the highest point (voltage) recorded during the detected QRS complex. Additionally, a displacement waveform 504b includes a chest compression cycle 506b.

In one embodiment, upon determination of the fiducial 519b, the processor 123 of the medical device 114 causes the automated chest compressor 108 to immediately initiate the synchronized chest compression 522. As illustrated, this enables the chest compression 506b to be further "lengthened." For example, the downstroke (507b to 508b) may be lengthened to approximately 150 ms, the hold (508b to 509b) may be lengthened to 125 ms, and the upstroke (509b to 511b) may also be lengthened to 125 ms. In this example, the downstroke occurs through the majority of the R-wave. Likewise, the chest compression could be lengthened or shortened.

In alternative embodiments, (after determination of the QRS fiducial point) the delay to when the target compression depth is reached (as designated by point 508b of the compression waveform) may be: 150 milliseconds or less after the peak of the R-wave (as designed by reference point 510C), 145 milliseconds or less after the peak of the R-wave, 140 milliseconds or less after the peak of the R-wave, 135 milliseconds or less after the peak of the R-wave, 130 milliseconds or less after the peak of the R-wave, 125 milliseconds or less after the peak of the R-wave, 120 milliseconds or less after the peak of the R-wave, 115 milliseconds or less after the peak of the R-wave, 110 milliseconds or less after the peak of the R-wave, 105 milliseconds or less after the peak of the R-wave, 100 milliseconds or less after the peak of the R-wave, 95 milliseconds or less after the peak of the R-wave, 90 milliseconds or less after the peak of the R-wave, 85 milliseconds or less after the peak of the R-wave, 80 milliseconds or less after the peak of the R-wave, 75 milliseconds or less after the peak of the R-wave, 70 milliseconds or less after the peak of the R-wave, 65 milliseconds or less after the peak of the R-wave, 60 milliseconds or less after the peak of the R-wave, 55 milliseconds or less after the peak of the R-wave, 50 milliseconds or less after the peak of the R-wave, 45 milliseconds or less after the peak of the R-wave, 40 milliseconds or less after the peak of the R-wave, 35 milliseconds or less after the peak of the R-wave, 30 milliseconds or less after the peak of the R-wave, 25 milliseconds or less after the peak of the R-wave, 20 milliseconds or less after the peak of the R-wave, 15 milliseconds or less after the peak of the R-wave, 10 milliseconds or less after the peak of the R-wave, or 5 milliseconds or less after the peak of the R-wave.

Figure 5G:
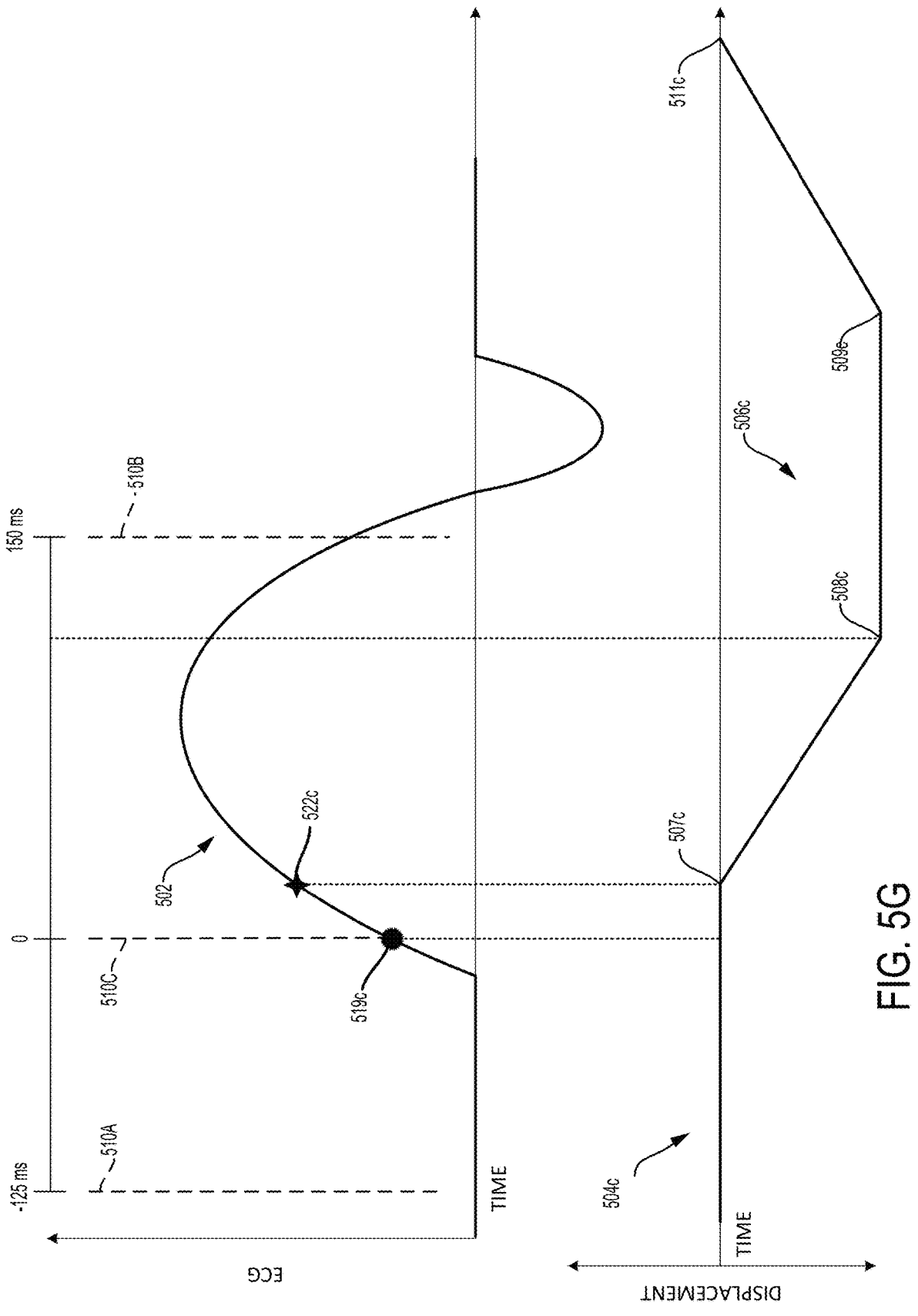
FIG. 5G illustrates an example in which the time window is based on the fiducial point.

FIG. 5G illustrates an example in which the time window is based on the fiducial point 519c. This embodiment is similar to previous embodiments, such as FIG. 5D. However, in this embodiment, the time window for determining synchronization is based on a fiducial point 519c (i.e., when the QRS complex is detected), rather than the peak of the R-wave as in other embodiments.

Example 1: Evaluating the Hemodynamic
Consequence of Synchronized Chest Compressions
to Cardiac Electrical Activity in a Swine Model of
Pseudo-Pulseless Electrical Activity A scientific study was performed by a portion of the inventors on a swine to evaluate the effect of varying coupling intervals of synchronization of chest compression and pseudo-pulseless electrical activity (p-PEA) on blood flow and pressure in a swine asphyxial model of p-PEA. A hypothesis tested in the study was whether prolonged delays in the coupling interval of a chest compression with intrinsic electrical activity during p-PEA would worsen blood flows and pressures generated by the chest compression. Conversely, another hypothesis tested was whether short delays in the coupling interval of the chest compression with intrinsic electrical activity during P-PEA would improve blood flows and pressures generated by chest compression.

Put another way, the study tested whether short delays in the synchronization of the chest compression with the intrinsic electrical activity during p-PEA would improve the blood flows and pressures generated by the chest compression. The study mimicked a common form of respiratory cardiac arrest with an advanced cardiac life support response. The conditions included an induced asphyxial event which significantly reduced the fraction of inspired oxygen (FiO2) and subsequently reduced blood pressures to approximately 40/20 mmHg (millimeters of mercury). This was followed by synchronized chest compression and improved FiO2. Additionally, rescue defibrillations were provided if ventricular fibrillation or tachycardia occurred. The primary data being collected were aortic blood pressure, right atrial blood pressure, and carotid blood flow. Secondary data points were jugular vein blood flow, intracranial pressure (ICP), cerebral perfusion pressure (CPP), and end-tidal carbon dioxide (EtCO2).

A porcine model of p-PEA and resuscitation in domestic pigs, weighing 30±3 kg, was utilized for the study. The porcine model was selected because it is an established model and has been used successfully for more than 20 years to investigate the treatment of cardiac arrest and methods of resuscitation. Specifically, the following measurements were taken: cerebral oxygenation (StO2) was measured with a commercially available near-infrared spectroscopy (NIRS) tissue oximetry device; intracranial pressure was measured with a Millar pressure catheter in the soft tissue of the left parietal lobe of the brain; cerebral perfusion pressure (CerPP) was calculated as mean arterial pressure (from the aortic pressure signal) minus mean intracranial pressure, aortic and right atrial pressure was measured with Millar catheters and allowed for estimation of coronary perfusion pressure (CPP), which was calculated as the difference between diastolic pressure in the aorta and the diastolic pressure in the right atrium; EtCO2 was monitored to confirm intubation and as a measure of pulmonary gas exchange during the experiment; blood flows were monitored at the carotid artery and jugular vein. Other measurements included: Electrocardiography (ECG), pulse oximetry, and body temperature (temperature probe in the rectum).

The experimental procedure included anesthesia maintained with isoflurane during experimental preparation. Arterial blood gas was taken prior to the start of the experiment and analyzed. During the experiment, anesthesia was maintained as a continuous rate infusion with either Fentanyl, Propofol or Ketamine/midazolam. Mechanical ventilation was provided with a volume and rate limited ventilator. The depth of anesthesia was monitored by assessing heart rate, blood pressure, respiration, mandibular jaw tone, and absence of canthal reflex. Continuous monitoring of physiological parameters during anesthesia and throughout the experiment included cerebral oxygenation, aortic and right blood pressure, intracranial pressure, ECG, EtCO2, pulse oximetry, body temperature (temperature probe in the rectum), and carotid and jugular blood flow.

Prior to induction of P-PEA, baseline values were collected. A bolus of rocuronium (or another substitute paralytic) was given 30 seconds prior to the induction of P-PEA to prevent gasping. Additional boluses of the paralytic were given to prevent gasping as needed. P-PEA was induced via decreases in the minute ventilation and the gas mixture of O2/N2 such that a FiO2 of 6% was achieved. The onset of P-PEA was defined as an aortic systolic pressure≤40 mmHg recorded by the aortic catheter in the presence of an organized cardiac rhythm. Chest compressions were performed by a custom stepper motor based system that is under full computer control. Mechanical ventilations were performed by a Harvard ventilator (e.g., the Harvard Large Animal Ventilator, Model 613).

Figure 6:
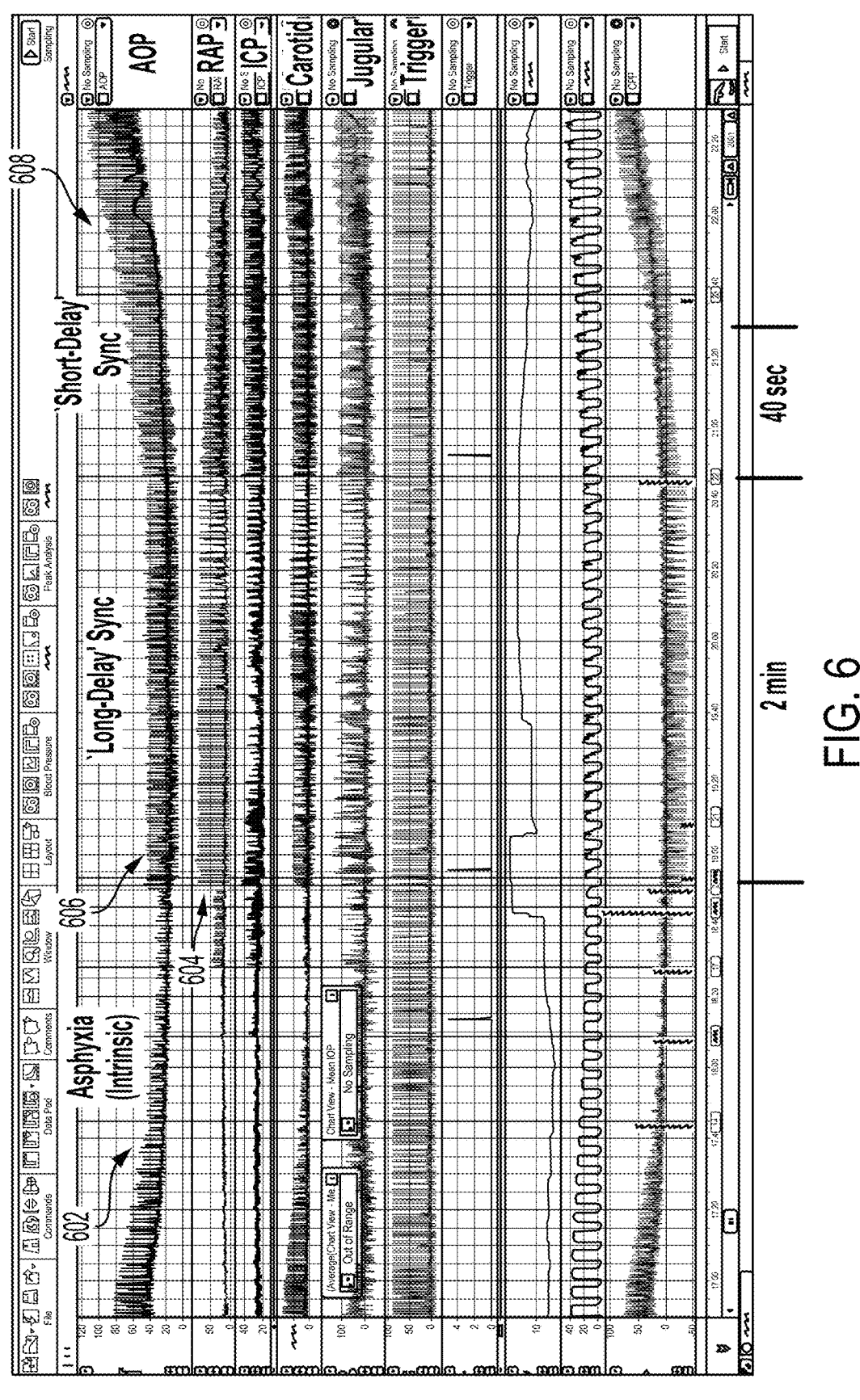
FIGS. 6-8 illustrate data from a scientific study showing the hemodynamic effects of chest compressions synchronized according to various delay periods.
Figure 7:
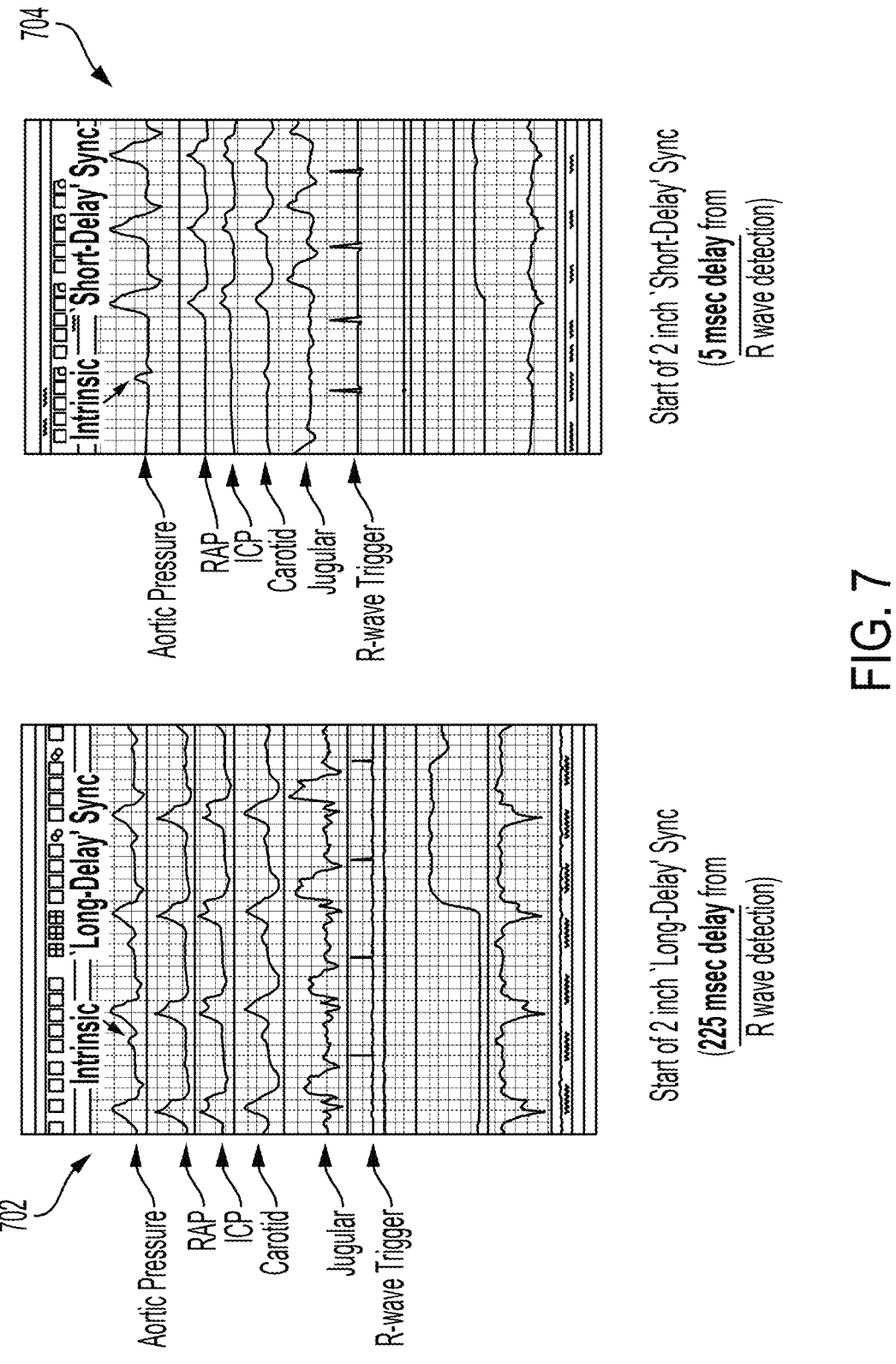
Figure 8:
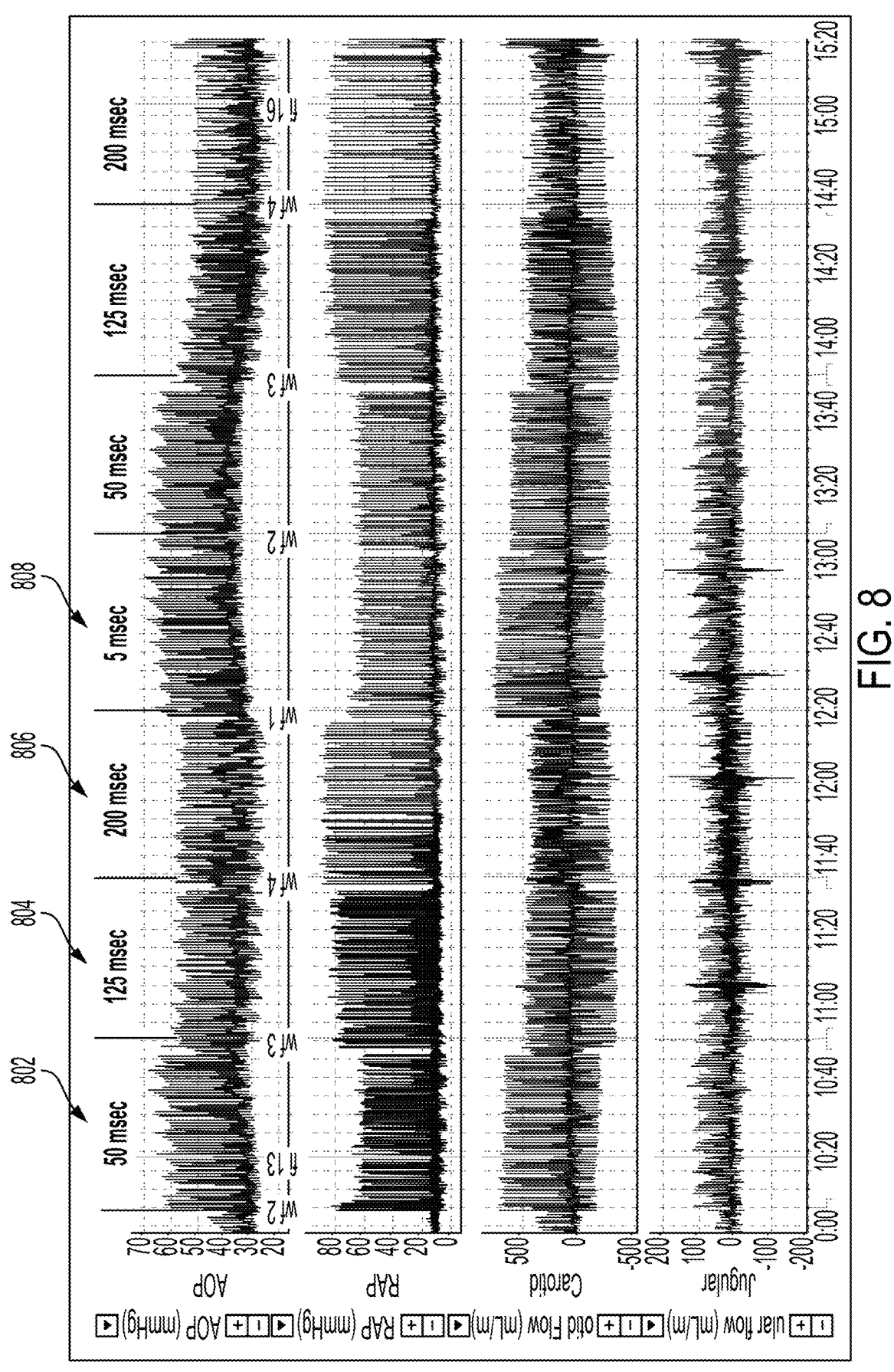

It was expected that each experiment would include at least three asphyxial insults. The synchronized chest compressions had four different timings/delays (as shown in FIGS. 6-8 below) from the R-wave and defined as waveform 1=5 milliseconds, waveform 2=50 milliseconds, waveform 3=125 milliseconds, and waveform 4=200 milliseconds.

The asphyxial and resuscitation protocol of test subject includes, first, baseline values were recorded, then respiration was reduced to a rate of 0 breaths per min and reduce FiO2 to 6% via mixing nitrogen into the airway. Then wait until target aortic systolic blood pressure of 40 mmHg was achieved. After achieving target aortic systolic BP, wait three minutes if it is asphyxial insult #1, two minutes if it is asphyxial insult #2, and one minute if it is asphyxial insult #3. Next, increase FiO2 to approximately 12% and test synchronized chest compressions (waveforms 1-4; detailed above) in 45-second epochs for a maximum of six minutes. If the animal was not resuscitated (defined as systolic BP>80 mmHg) after six minutes, a rescue protocol will be initiated to revive the patient.

Waveforms will be tested in four different groups:

Group 1 (N=3): 5 ms test waveform 1, 2, 3, 4, 1, 2, 3, 4

Group 2 (N=3): 50 ms test waveform 2, 3, 4, 1, 2, 3, 4, 1

Group 3 (N=3): 125 ms test waveform 3, 4, 1, 2, 3, 4, 1, 2

Group 4 (N=3): 200 ms test waveform 4, 1, 2, 3, 4, 1, 2, 3

A plurality of measurements including hemodynamic data, EtCO2 (end tidal carbon dioxide), and ECG was continuously measured and recorded on a PC-based data acquisition system (PowerLab and LabChart, ADInstruments Inc., Colorado Springs, CO). A blood flow sensor placed on the jugular vein and carotid artery blood vessels provided a measure of blood flow. Cerebral oxygenation (via NIRS) was measured from a stand-alone device. The FiO2 data was measured by a stand-alone device.

FIG. 6 illustrates a graph that shows the improved hemodynamics achieved with a short synchronized delay in the setting of pseudo-PEA (P-PEA) in test animal subjects. Building on these animal studies, it is apparent that synchronization of chest compression to the R-wave of a QRS with a short delay from the detection of the R-wave (e.g., between 5 and 15 milliseconds, and preferably no longer than 100 milliseconds) improves the quality of chest compression (as measured by blood pressures and flows generated from the chest compression) over non-synchronized chest compressions and/or when chest compressions are performed more than 100 milliseconds after the peak of a detected R-wave.

Reference numeral 602 illustrates the aortic pressure (AOP) declining as part of the induced asphyxia in the patient. Reference numeral 604 illustrates increasing right atrial pressure (RAP) that occurs in P-PEA. This effect is harmful and is not life-sustaining. If the trend was allowed to continue, heart failure would result due to lack of perfusion.

Reference numeral 606 illustrates the effect of synchronized chest compressions with a long delay (225 milliseconds): AOP and RAP pressures are increased with the synchronized chest compressions, but over the course of the two minutes, the hemodynamics of the subject does not improve.

Reference numeral 608 shows the beneficial effect of using a short synchronized delay (within approximately 5 milliseconds of R-wave detection). Within just 40 seconds, the aortic pressure AOP starts to markedly increase, while the right atrial pressure simultaneously decreases indicating reduced venous congestion. Both carotid flow and jugular flow (labeled carotid and jugular, respectively) were also observed to increase in the presence of the short synchronized delay indicating improved blood flow to and from the brain.

The section labeled "Trigger" represents all of the identified QRS complexes detected by the medical device used in the study. That is, every time a QRS was detection a "Trigger" was generated. However, it may be more accurate to describe the Trigger signals as detection signals.

FIG. 7 is a magnified portion of the signals illustrated in FIG. 7. This figure further illustrates the improved hemodynamics achieved with a short synchronized delay (e.g., 5 milliseconds; shown in section 704) compared to the longer synchronized delay (225 milliseconds; shown in section 702). If looking at section 702 and AOP pressure, it is appreciated that the long synchronized delay causes a pressure increase from the compression well after the intrinsic cardiac contraction. This compression occurs during diastole (i.e., when the heart trying to relax and refill with blood). This causes a large increase in right atrial pressure. Compared to section 704, however, the short synchronized delay (5 milliseconds) provides a chest compression synchronized with the R-wave of the subject's intrinsic cardiac contraction. The result is a larger overall aortic pressure and a reduced right atrial pressure. This helps illustrate the value of performing short synchronized delay compressions in the setting of P-PEA. That is, the synchronized chest compression according to the shortened delay timings helped enhance the subject's hemodynamics.

FIG. 8 is another example illustrating the improved hemodynamics achieved with a short synchronized delay of chest compression in a subject suffering P-PEA. Similar to previous examples, delays greater than 100 milliseconds (e.g., 125 milliseconds and 200 milliseconds 804, 806 respectively) yields more negative results for the test subject (e.g., decreasing AOP, increasing RAP, decreasing carotid flow). In contrast, delays less than 100 milliseconds (e.g., 5 and 50 milliseconds, 802, 808 respectively), yield more positive results (e.g., increasing AOP, decreasing RAP, and increasing carotid flow). This figure provides further indication of the benefit proving chest compressions less than 100 milliseconds after the peak of the R-wave (preferably as short as possible after the peak of the R-wave).

Example 2: Hemodynamic Comparison of Pseudo-Pulseless Electrical Activity, Pseudo-Pulseless Electrical Activity Treated with Standard Chest Compression, and Pseudo-Pulseless Electrical Activity Treated with Synchronized Chest Compression Another scientific study was performed by a portion of the inventors on a swine to evaluate the effect of chest compressions and synchronized chest compressions on the hemodynamics of pseudo-pulseless electrical activity (p-PEA). This study was designed to test the hypotheses that standard chest compression resulted in better hemodynamics than untreated p-PEA and that synchronized compressions resulted in better hemodynamics than standard CPR.

A porcine model of p-PEA and resuscitation in domestic pigs, weighing 30±3 kg, was utilized for the study. The porcine model was selected because it is an established model and has been used successfully for more than 20 years to investigate the treatment of cardiac arrest and methods of resuscitation. The study mimicked a common form of respiratory cardiac arrest with an advanced cardiac life support response. The experimental procedure included anesthesia maintained with isoflurane during experimental preparation. Arterial blood gas was taken prior to the start of the experiment and analyzed. During the experiment, anesthesia was maintained as a continuous rate infusion with either Fentanyl, Propofol or Ketamine/midazolam. Mechanical ventilation was provided with a volume and rate limited ventilator. The depth of anesthesia was monitored by assessing heart rate, blood pressure, respiration, mandibular jaw tone, and absence of canthal reflex. Continuous monitoring of physiological parameters during anesthesia and throughout the experiment included cerebral oxygenation, aortic and right blood pressure, intracranial pressure, ECG, EtCO2, pulse oximetry, body temperature (temperature probe in the rectum), and carotid and jugular blood flow.

Prior to induction of P-PEA, baseline values were collected. A bolus of rocuronium (or another substitute paralytic) was given 30 seconds prior to the induction of P-PEA to prevent gasping. Additional boluses of the paralytic were given to prevent gasping as needed. P-PEA was induced via decreases in the minute ventilation and the gas mixture of O2/N2 such that a FiO2 of 6% was achieved. The onset of P-PEA was defined as an aortic systolic pressure≤50 mmHg recorded by the aortic catheter in the presence of an organized cardiac rhythm. Chest compressions were performed by a custom stepper motor based system that is under full computer control. Mechanical ventilations were performed by a Harvard ventilator (e.g., the Harvard Large Animal Ventilator, Model 613).

Once the target aortic blood pressure was achieved the FiO2 was raised to 10% and the animal received 8 periods of 45-second treatments according to the following pattern repeated twice: Treatment 1, untreated, Treatment 2, untreated. In half the animals, Treatment 1 was synchronized chest compressions and Treatment 2 was unsynchronized chest compressions. In the other animals, the order was reversed. After completion of the 8 cycles, the FiO2 was increased to 100% and the animal was resuscitated. In the event of asystole or ventricular fibrillation, a standard resuscitation protocol was followed with standard chest compressions, defibrillation shocks when appropriate, and vasoactive drugs when needed. The primary data being collected were aortic blood pressure, right atrial blood pressure, and carotid blood flow. Secondary data points were jugular vein blood flow, intracranial pressure (ICP), cerebral perfusion pressure (CPP), and end-tidal carbon dioxide (EtCO2).

It was expected that each experiment would include at least three asphyxial insults followed by treatment and resuscitation. Synchronized chest compressions were triggered on the R-wave and delivered without delay. Unsynchronized chest compressions were delivered at a rate of 100 compressions per minute with a 50% duty cycle.

Figure 9A:
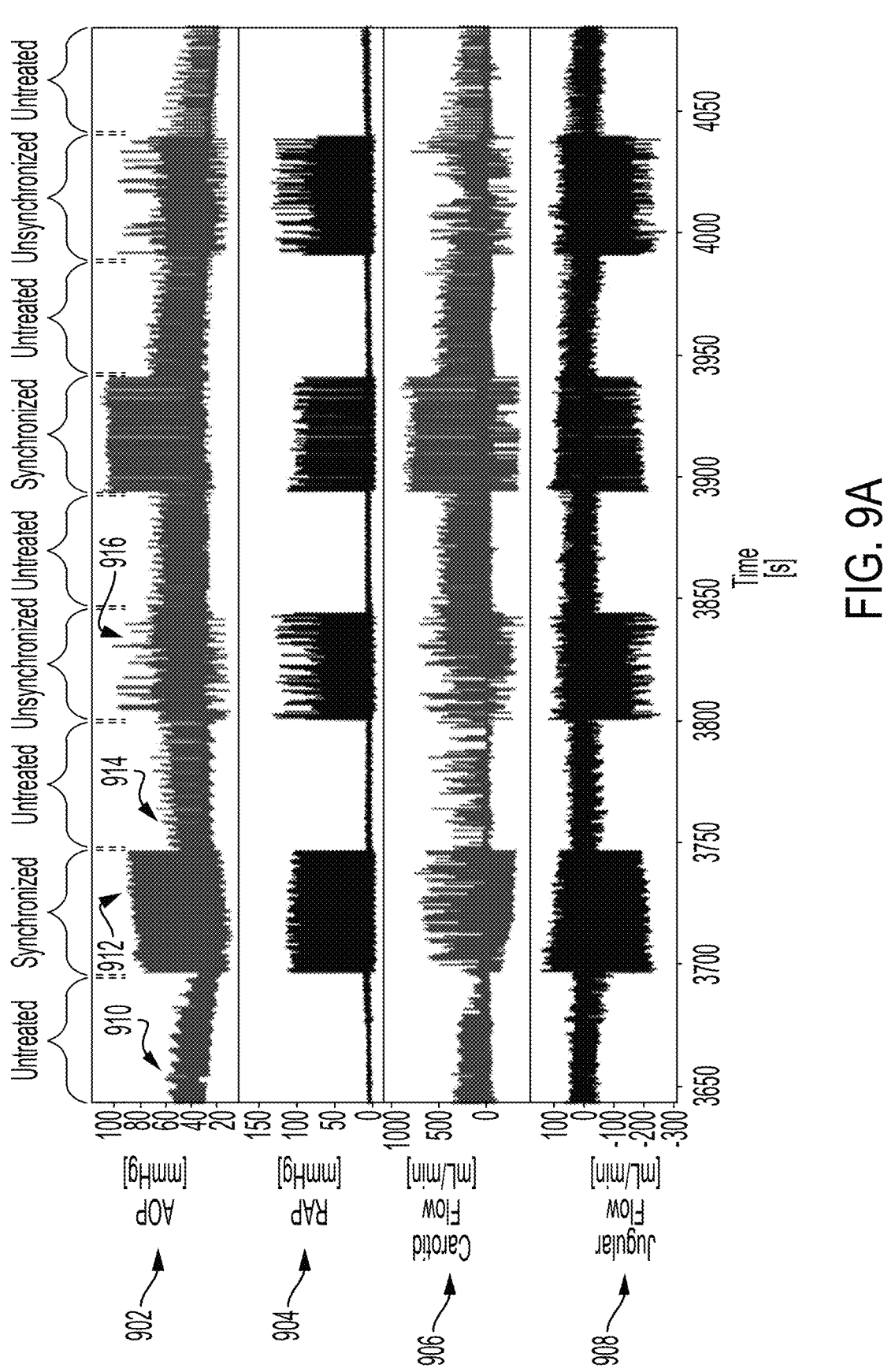
FIG. 9A illustrates data from a scientific study showing the hemodynamic effects of synchronized and unsynchronized chest compressions.

FIG. 9A is a series of time graphs illustrating a portion of the data from the above-described study and demonstrates the improved hemodynamics resulting from synchronized chest compressions compared to unsynchronized chest compressions (and non-treatment). Specifically, reference numeral 902 illustrates the measured aortic pressure (AOP)

data, reference numeral 904 illustrates the measured right atrial pressure (RAP) data, reference numeral 906 illustrates the measured carotid flow data, and reference numeral 908 illustrates the measured jugular flow data during the above-described protocol.

In some cases, the PEA condition is found in cardiac arrest victims who have been defibrillated often following extended periods of fibrillation or asystole. The extended periods of fibrillation or asystole result in the myocardium being depleted of its energy stores, its contractility being degraded resulting in a PEA condition. This is particularly the case when ROSC occurs as a direct result of electrical defibrillation. In one example, synchronized compressions may be initiated as soon as an organized rhythm is detected subsequent to the delivery of the defibrillation shock. In this example, the test for unconscious hypotension in step 316 (of FIG. 3) is not needed for the post-defibrillation shock, and step 316 may provide a message or other prompt for the user to confirm whether the patient is exhibiting an organized ECG, for example, a message that reads: "Organized ECG?"

As illustrated, for a representative portion of data collected, compression and non-compression protocols are labeled: Synchronized, Unsynchronized, and Untreated. In this example set of data, due to the induced asphyxia in the test subject, the AOP 902 was observed to deteriorate during the region 910 (labeled "Untreated") in which no chest compressions were provided. As no compressions were being provided to the subject, the corresponding measured RAP values 916 were observed to be near zero. If this trend was allowed to continue (with no chest compressions provided), then heart failure and death would likely be the result due to a lack of blood flow arising from the inability of the heart to transport blood through the body.

Region 912 (labeled "Synchronized") illustrates the effect of synchronized chest compressions (i.e., chest compressions synchronized to the intrinsic heartbeats of the subject) on the patient. As illustrated, the AOP data 912 was observed to increase substantially. Moreover, there is the start of a general upward trend in the AOP data 912 (e.g., peaks starting at approximately 75 mmHg and increasing toward 90 mmHg) further illustrate how the hemodynamics of the subject was improving in response to the synchronized chest compressions. Similarly, both carotid flow data 906 and jugular flow data 908 were also observed to have improved as well in response to the synchronized chest compressions, as exhibited by the dramatic increase in flows. The corresponding RAP data 904 was also observed to substantially increase as well with the synchronized chest compressions. However, this increase is typically the result of the chest compressions, as normal RAP values are often 2-6 mmHG. Put another way, the increased RAP peak values are indicative of the manner in which chest compressions being applied (this will be detailed in more depth below with respect to FIGS. 10A and 10B). If the synchronized compressions had been continued (and the asphyxiation been discontinued), the subject was observed to be trending toward achieving ROSC.

The next sequence in the testing procedure was to discontinue treatment as shown by region 914 (labeled "Untreated"). As expected, the AOP peak 914 drops significantly and RAP 904 was also observed to drop back to essentially zero (indicating a lack of chest compressions). The next step in the procedure was to perform unsynchronized compressions, denoted by region 916 (labeled "Unsynchronized"). While treating the subject with unsynchronized chest compressions resulted in an overall improvement as compared to non-treatment, the synchronized chest compressions denoted by region 912 provided consistently higher AOP values.

As shown in FIG. 9A, the hemodynamic effects for the synchronized compressions as compared to the unsynchronized compressions were noticeably different. For instance, the AOP, RAP, carotid low and jugular flow for unsynchronized compressions were observed to exhibit a greater level of variability than that for the synchronized compressions. Such variability when unsynchronized compressions are provided may be due to the fact that the unsynchronized compressions in this example are provided at a set rate while the subject's heart is variable. More specifically, during unsynchronized chest compressions, chest compressions are applied at a predefined rate (e.g., 100 compressions per minute). However, the test subject's heart rate varies. Consequently, some chest compressions may appear synchronized with the intrinsic heart rate of the subject on occasion, this coordination is simply the result of chest compressions and the patient's intrinsic heart rate temporarily aligning. This sporadic, naturally occurring coordination gives rise to the more randomly occurring positive peaks in the unsynchronized section. It should also be noted that the unsynchronized compressions were observed to create randomly occurring yet significant downward spikes in AOP which is not seen with untreated or synchronized compressions. This observation serves to further illustrate the random potentially detrimental effects of unsynchronized compressions (compared to synchronized chest compressions).

Example 3: Evaluating the Hemodynamic
Consequence of AHA Guideline Compliant Chest
Compressions to Cardiac Electrical Activity in a
Swine Model of Pseudo-Pulseless Electrical
Activity A scientific study was performed on a swine model to evaluate the effect of chest compressions on the hemodynamics of pseudo-pulseless electrical activity (p-PEA). The hypothesis was that the time interval between a chest compression and the ventricular contraction during pseudo electro-mechanical dissociation (P-EMD, which is also known as p-PEA) would influence the hemodynamics created by the chest compression. Unsynchronized chest compressions compliant with AHA current guidelines at 2.0-inch chest compression depth and 100 compressions per minute were applied to the P-PEA swine model.

Mean arterial pressure, aortic systolic pressure, diastolic pressure, right atrial pressure, coronary perfusion pressure, and ECG were measured. The results are displayed in the Table below and in FIG. 9C. The location of R-waves in the ECG and peak aortic pressures were detected via signal processing. A nearest-neighbor analysis was conducted to determine the time-gap between the R-wave and the peak aortic pressure, as provided in the figure below. The calculated time interval ('t'; measured in milliseconds) in this example is defined as $t\_peakAOP-t\_rwave$ between nearest-neighbor peak pressures and R-waves. Peak aortic pressures that had more than one R-wave nearest neighbor were excluded from the analysis, resulting in 1,761 analyzed chest compressions.

Time intervals were then divided into quartiles, and hemodynamic parameters were compared between the quartiles using a repeated measure ANOVA (analysis of variance) with Bonferroni correction. Statistical significance was defined as a p-value lower than 0.05.

The time interval quartiles were then defined as:

$$Q1: t \geq -110 \text{ ms};$$

$$Q2: -110 \text{ ms} \geq t > -0.01 \text{ ms};$$

$$Q3: -0.010. \text{ ms} \geq t > 110 \text{ ms; and}$$

$$Q4: t \geq 110 \text{ ms}.$$

The measured results were:

| Metric (mmHg) | Quartile 1 (ms) $t \geq -110$ ms | Quartile 2 (ms) $-110 \geq t > -0.01$ | Quartile 3 (ms) $-0.01 \geq t > 110$ | Quartile 4 (ms) $t \geq 110$ |
|---|---|---|---|---|
| Mean Arterial Pressure | 33.4 ± 0.5 | 38.2 ± 0.5 | 40.1 ± 0.5 * | 34.7 ± 0.5 |
| Aortic Systolic Pressure | 68.4 ± 0.6 | 73.3 ± 0.6 * | 75.5 ± 0.6 * | 72.5 ± 0.6 |
| Aortic Diastolic Pressure | 15.7 ± 0.5 | 20.4 ± 0.5 * | 20.3 ± 0.5 * | 14.6 ± 0.5 |
| Right Atrial Pressure | 40.3 ± 0.3 | 39.9 ± 0.2 | 38.2 ± 0.3 | 35.1 ± 0.2 * |
| Coronary Perfusion Pressure | 13.0 ± 0.5 | 15.7 ± 0.4 * | 14.7 ± 0.4 * | 11.6 ± 0.4 |
| Intra-Cranial Pressure | 29.0 ± 0.1 | 29.3 ± 0.1 | 28.7 ± 0.1 | 28.1 ± 0.1 * |
| Cerebral Perfusion Pressure | 33.2 ± 0.5 | 37.8 ± 0.5 * | 38.6 ± 0.5 * | 33.7 ± 0.5 |
| Carotid Blood Flow | 0.56 ± 0.01 | 0.65 ± 0.01 | 0.86 ± 0.01 * | 0.72 ± 0.01 |
| Jugular Blood Flow | 0.25 ± 0.01 | 0.33 ± 0.01 * | 0.35 ± 0.01 * | 0.30 ± 0.01 |

Note:
a '*' indicates, "statistically different from other condition."

Figures 9B, 9C:
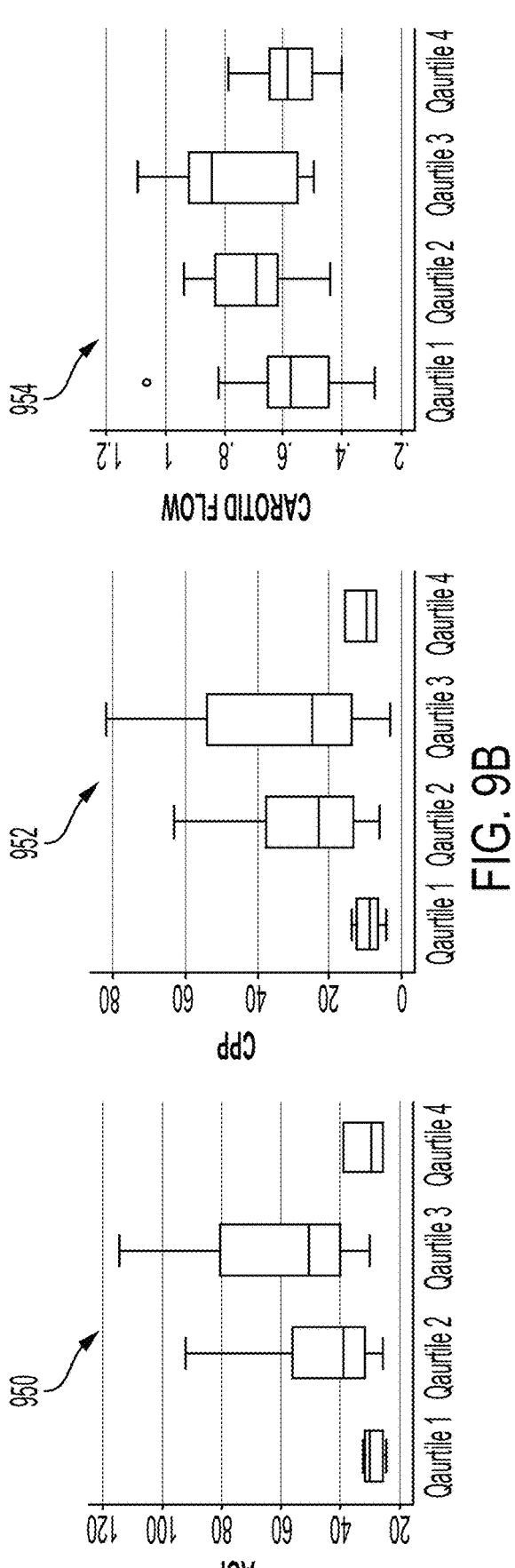
FIG. 9B illustrates data from a scientific study showing the effects of chest compressions synchronized at various intervals relative to an R-wave.
FIG. 9C illustrates pressure measurements recorded during the chest compressions of the scientific study detailed in FIGS. 9A and 9B.

FIG. 9B is a visual representation (i.e., box plots) of the data from FIG. 9C and the above table. In general, a box plot is a method for comparing information that has been divided into separate groups. In the illustrated example, the data are the measured pressure values, and the groups (i.e., the quartiles) are the different time-windows; with time zero being the peak of the R-wave. As shown, FIG. 9B includes separate graphs for aortic pressure (AOP) 950, coronary perfusion pressure (CPP) 952, and carotid blood flow 954. Additionally, the whiskers of the box plots indicate the upper and lower bounds. In short, a larger box is better because a larger box indicates higher measured pressures, which translates into better hemodynamics for the test subject.

The results suggest that quartiles 2 and 3 had the best results. That is, a chest compression that generates peak aortic pressure (e.g., when the chest compression has reached the target depth) within the time windows from approximately 100 ms before to approximately 100 ms after the R-wave are preferable to chest compressions outside of that those windows. Additionally, the data appears to indicate that there may even be a slight benefit to having the peak pressure generated after the R-Wave (i.e., Quartile 3). Accordingly, the data further provides evidence that shorter time gaps within a particular window of time relative to the peak of the R-Wave during which chest compressions are applied (e.g., reaching the target depth of compression), both before and after the peak of the R-wave, are associated with improved hemodynamics.

FIG. 10A shows a series of time graphs illustrating synchronized data obtained from the study detailed above with respect to FIG. 9A. Specifically, the graphs depict the relationships between detected QRS complexes (in the ECG data labeled ECG 1010), chest compressions (labeled Position 1016), the measured right atrial pressure (labeled RAP 1014), and the measured aortic pressure (labeled AOP 1012) when compressions are synchronized to the intrinsic heartbeat of the subject.

In more detail, ECG data 1010 is obtained via ECG sensors attached to the test subject. In this example, the ECG data appears inverted, which is an artifact of electrode placement. Thus, traditionally positive values are negative, and the traditionally negative values are positive. For example, the R-waves, which are often displayed as a positive value or peak (e.g., as shown in FIG. 5A) appear as downward peaks in this data. Accordingly, while it may appear the detection signals 1002a-g are triggered on a wave other than the R-wave (which may appear traditionally as negative), they were triggered on the R-wave.

Each time an R-wave is detected, a detection signal 1002a-g is generated. In response to the detection signals 1002a-g, the chest compressor initiated a chest compression 1007a-g on the test subject. The continuous measure of the position of the chest compressions 1007a-g was captured via one or more accelerometers attached to the subject. As illustrated, the detection signals 1002a-g immediately precede the initiated chest compressions 1007a-g, which provide evidence that the chest compressions 1007a-g were initiated in response to the detection of the R-waves.

As detailed previously, RAP values are typically observed to be fairly low (e.g., 2-6 mmHG) for natural heartbeats. Consequently, a much large RAP value is indicative of a chest compression. As seen in the RAP data 1014, all of the shown RAP values reach approximately 100 mmHG or more. These relatively high values are indicative of pressures caused by chest compressions.

Furthermore, dotted lines 1008a-g represent the points in time when the downstroke portion of the chest compressions 1007a-g reached a target chest compression depth (i.e., target depth). As illustrated, the RAP peaks, AOP peaks, and the point when the compressions were at target depth are all aligned. Specifically, as the chest compressions 1007a-g are synchronized to the intrinsic heart rate of the subject in this portion of the data, the target depth (dotted lines 1008a-g), peaks of right atrial pressures (RAP) 1006a-g, and the peaks of the aortic pressures (AOP) 1004a-g are all aligned for each chest compression, as would be expected. This coordination of the compression and peak pressures illustrates the hemodynamic benefit of synchronization of the chest compression 1007a-g with the detected heartbeats. As will be seen in FIG. 10B, unsynchronized chest compressions lack this alignment between the target depth and AOP peaks.

In the study from which this data was obtained, the target depth was set to 2 inches. In general, the target depth is simply how deep the chest compressor was set to compress the chest of the subject during each chest compression. However, for detection purposes (i.e., tolerance in detecting when the target depth is reached), the target depth was determined to have been reached the target depth upon meeting or exceeding approximately 90% of the target depth (e.g., a 90% point). This 90% point provides a range for which the measured depth is determined to have reached the target depth. In alternative embodiments, the target depth may be determined to have been reached upon to meeting or exceeding approximately 75%, 80%, 85%, 95%, 98%, 99% of the target depth.

Additional evidence that the chest compressions 1007a-g are synchronized with the intrinsic heartbeats is shown non-uniform spacing of the chest compression in the position data 1016. This non-uniformity in the spacing of position data indicates that the chest compressions 1007a-g are not occurring a predefined rate, but rather are timed according to when the QRS complex is detected.

FIG. 10B is a series of time graphs illustrating unsynchronized data from the study detailed with respect to FIG. 9A and illustrates the lack of time alignment between a detected QRS complex (e.g., ECG data 1028) and chest compressions (position data 1034).

The most obvious indication of lack of time alignment is the fact that there are only six detected heartbeats (i.e., detection signals 1020a-f), but there are 7 chest compressions 1025a-g. Additionally, whereas the timing of the chest compressions in FIG. 10A was non-uniform (due to the chest compressions occurring in response to detected QRS complexes), here, the chest compressions 1025a-g are all evenly spaced apart indicating consistent timing. This uniform timing is because the chest compressions are performed at a predefined rate (e.g. 100 compressions per minute) and occur regardless of if or when detection signals 1020a-f are generated. Whereas in FIG. 10A, a detection signal (1002a-g) caused a chest compression, that is not the case in FIG. 10B. In this example, the chest compressions and heartbeats occur independently of each other. As illustrated, and will be explained in greater detail below, the detection signals 1020a-f occur at various points throughout chest compression 1025a-g (unlike in FIG. 10A where the chest compressions immediately followed a detection signal).

Referring to when chest compression 1025a of FIG. 10B occurs, the pressure generated by this compression results in a RAP peak 1024a and an AOP peak 1022a. As this chest compression 1025a does not occur during the timing of a heartbeat, the AOP value is generally lower in value compared to AOP peaks in which the compression happened to occur at a time point when a QRS complex had appeared. A similar effect is observed when the third chest compression 1025c occurs. Specifically, AOP peak 1022c is generated, however, the magnitude of the AOP peak 1022c is less than that which would typically be observed when chest compressions are time aligned with the intrinsic heartbeat.

Referring to chest compression 1025b of FIG. 10B, as discussed above, due to the variable nature of when the test subject's heartbeats occurred, some chest compressions would naturally occur during a period in which the intrinsic heartbeat also occurs. This naturally occurring timing is illustrated when the detection signal 1020a for an R-wave and chest compression 1025b are marked, and is shown as the time at which the target chest compression depth is reached 1026b is substantially aligned with the RAP peak 1024b, which is also substantially aligned with the AOP peak 1022b.

The lack of time alignment between the QRS complex and chest compressions becomes apparent in subsequent compressions. For instance, in FIG. 10B, chest compressions 1025d, 1025e, 1025f occurred at times that were not well aligned with intrinsic heart beats. Referring to the AOP data 1030, rather than generating a single, rather strong AOP peaks (as demonstrated by peaks 1004a-g of FIG. 10A and peak 1022b of FIG. 10B in which the chest compressions were well timed), the timing of the fourth chest compression 1025d results in "double peaks." These double peaks (i.e., 1021a and 1022d; 1021b and 1022e; and 1021c and 1022f) generally result in less forward blood flow from the heart as compared to compressions that are properly timed with the heartbeat.

In more detail, upon detection of a heartbeat, the detection signal 1020b is generated. A RAP peak 1023a is generated, which is small in value as expected for a natural heartbeat, and corresponds with the AOP peak 2021a. While the heartbeat is occurring, chest compression 1025d was initiated. Accordingly, due to the compression 1025d, the resulting RAP peak 1024d is generated and is higher than the RAP peak 1023a resulting from the natural heartbeat, and a "secondary" AOP peak 1022d also results. This process of the chest compressor and heartbeat of the patient being out of alignment repeats itself again with respect to detections signals 1020c and 1020d, and chest compressions 1025e and 1025f, respectively.

Lastly, as shown with respect to AOP peaks 1022f, 1021d, 1022g, and 1021e, the effects of being significantly out of time alignment for several chest compressions can cause "cascading" drops in AOP pressure. In more detail, during the upstroke of chest compression 1025f, a heartbeat occurs (and a detection signal 1020e is generated). However, a possible theory is that this intrinsic heartbeat occurs when the heart is already in diastole (i.e., attempting to refill with blood from the pressure change resulting from chest compression 1025f). Accordingly, a weak AOP peak 1021d is measured because the heart was unable to completely refill with blood after the chest compression 1025f. The heart once again goes into diastole from the intrinsic heartbeat (identified by detection signal 1020e). Then, the next chest compression 1025g occurs and interrupts the refilling and ejects the blood again resulting in peak 1022g. As the heart was unable to completely refill after the intrinsic heartbeat (identified by detection signal 1020e), another relatively weak AOP peak 1022g is generated.

And yet again, a heartbeat (identified by detection signal 1020f) occurs in the middle of diastole (from the chest compression 1025g). The result is an even weaker AOP value at AOP peak 1021e. In short, due to a series of compressions and heartbeats being significantly out of synch (e.g., greater than 200 ms before or after the peak of the R-wave), the effectiveness of each subsequent chest compressions diminishes, and is observed to continue to diminish until the chest compressions are applied according to desirable timing relative to intrinsic heartbeats (e.g., 1020a, and 1025b) and/or until the compressions occur as such large enough intervals so as not to interfere with one another (e.g. 1025a and 1020a).

As detailed previously, the subject's heartbeat was variable. Consequently, the detrimental effects of the chest compressions being significantly out of synchronization (e.g., e.g., greater than 200 ms before or after the peak of the R-wave) typically only lasts for short periods of time. However, as shown in FIG. 9A (e.g., with unsynchronized data 916), the detrimental effects may occur, often repeatedly, in the future when the chest compressions and heartbeats become significantly unsynchronized again. Conversely, proper synchronization of the chest compression with intrinsic heart beats so that the target compression depth is reached at the appropriate time relative to the QRS complex (e.g., within 150 ms before or after the peak of the R-wave, within 100 ms before or after the peak of the R-wave), in accordance with the present disclosure results in overall improved hemodynamics.

Other Considerations:

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices described herein may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the present system. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one present system may be disclosed.

Other embodiments are within the scope of the present system. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A system for providing chest compressions to a patient during cardiopulmonary resuscitation, the system comprising:

at least one electrocardiogram (ECG) sensor configured to obtain ECG signals of the patient;

at least one hemodynamic activity sensor configured to detect hemodynamic activity of the patient;

an automated chest compressor configured to provide chest compressions to the patient, the automated chest compressor being at least one of: piston based or compression belt based; and at least one processor, memory and associated circuitry of a defibrillator device communicatively coupled with the at least one ECG sensor and the automated chest compressor, the at least one processor configured to:

receive and analyze the ECG signals of the patient, receive and analyze signals from the at least one hemodynamic activity sensor, determine whether the patient is in asystole based on the analysis of the ECG, in response to determining that the patient is in asystole, transmit a signal to the automated chest compressor to begin delivering chest compressions, in response to determining that the patient is not in asystole, determine whether a shockable cardiac rhythm is detected based on the analysis of the ECG signals, in response to determining that a shockable cardiac rhythm is detected, initiate shock protocol, automatically estimate a refractory period following a heartbeat for excluding R-wave identification based on the analyzed ECG signals and for withholding chest compressions during the estimated refractory period, adjust the estimated refractory period for withholding chest compressions such that a faster heart rate results in a smaller estimated refractory period and a slower heart rate results in a longer estimated refractory period, in response to determining that no shockable cardiac rhythm is detected, determine, based on the analysis of the ECG and hemodynamic signals, whether the patient is in a condition of unconscious hypotension with organized ECG, analyze, in response to a determination that the patient is in the condition of unconscious hypotension with organized ECG, the received ECG signals to detect a QRS complex, detect a slope of an ECG waveform comprising the QRS complex, after the estimated refractory period for withholding chest compressions, identify an R-wave within the QRS complex based on the detected slope for initiating a chest compression timed according to the detected R-wave and at a predetermined time relative to the QRS complex, and generate an output to cause the automated chest compressor to initiate the chest compressions outside of the estimated refractory period and at the predetermined time relative to the detected QRS complex based on detection of a leading edge of the R-wave of the QRS complex.

2. The system of claim 1, wherein the automated chest compressor is configured to apply the chest compression such that a target depth of the chest compression is achieved within a predetermined period of time relative to the QRS complex.

3. The system of claim 2, wherein the predetermined period of time relative to the QRS complex is within a range of approximately 125 milliseconds before a peak of an R-wave to 150 milliseconds after the peak of the R-wave.

4. The system of claim 2, wherein the predetermined period of time relative to the QRS complex is within a range of approximately 100 milliseconds before a peak of an R-wave to 100 milliseconds after the peak of the R-wave.

5. The system of claim 2, wherein the predetermined period of time relative to the QRS complex is within a range of approximately 75 milliseconds before a peak of an R-wave to 75 milliseconds after the peak of the R-wave.

6. The system of claim 2, wherein the target depth is a compression depth between 2 inches and 2.4 inches.

7. The system of claim 1, wherein the predetermined time relative to the QRS complex is within a range of from approximately 125 milliseconds before a peak of the R-wave of the QRS complex to 150 milliseconds after the peak of the R-wave.

8. The system of claim 7, wherein the at least one processor is configured to generate the output to apply the chest compression synchronized with the R-wave comprising initiating the chest compression 80 milliseconds or less before the peak of the R-wave.

9. The system of claim 7, wherein the at least one processor is configured to generate the output to apply the chest compression synchronized with the R-wave comprising initiating the chest compression 15 milliseconds or less before the peak of the R-wave.

10. The system of claim 7, wherein the at least one processor is configured to generate the output to apply the chest compression synchronized with the R-wave comprising initiating the chest compression 10 milliseconds or less before the peak of the R-wave.

11. The system of claim 1, wherein the predetermined time relative to the QRS complex is within a range of from approximately 100 milliseconds before a peak of the R-wave to 100 milliseconds after the peak of the R-wave.

12. The system of claim 1, wherein the at least one processor is configured to detect the QRS complex by identification of at least one of: a Q-wave, a P-wave, and the leading edge of the R-wave prior to occurrence of a peak of the R-wave.

13. The system of claim 1, wherein the at least one hemodynamic activity sensor includes at least one of: an invasive blood pressure sensor, pulse oximetry sensor, a Doppler ultrasonography sensor, a plethysmography sensor, a phonocardiography sensor, an echocardiography sensor, and a transthoracic impedance sensor.

14. The system of claim 13, wherein the at least one hemodynamic activity sensor includes a radio frequency sensor.

15. The system of claim 1, wherein the automated chest compressor comprises a compression belt and a belt tensioner configured to tighten the compression belt around the thorax of the patient in order to compress the thorax of the patient at a resuscitative rate.

16. The system of claim 1, wherein the automated chest compressor is a piston-based system that comprises:
   a piston,
   a piston driver,
   support structures for supporting the piston and piston driver, and
   a compression pad affixed to the piston.

17. The system of claim 1, further comprising a patient monitor, the patient monitor including an output device to generate audible or visual feedback to a rescuer.

18. The system of claim 17, wherein the visual feedback includes display of at least one of a patient's heart rate, blood pressure, ECG waveform, aortic pressure (AOP), right atrial Pressure (RAP), intracranial pressure (ICP), carotid blood flow, jugular blood flow, and an indication of an applied chest compression.

19. The system of claim 1, wherein the at least one processor is configured to:
   determine a fiducial point based on the detected QRS complex, and
   generate the output to apply the chest compression synchronized with the fiducial point comprising initiating the chest compression within a range from approximately 125 milliseconds before the fiducial point to 150 milliseconds after the fiducial point.

20. The system of claim 19, wherein the at least one processor is configured to generate the output to apply chest compression synchronized with the fiducial point comprising initiating the chest compression within 100 milliseconds or less after the fiducial point.

21. The system of claim 19, wherein the at least one processor is configured to generate the output to apply the chest compression synchronized with the fiducial point comprising initiating the chest compression within 75 milliseconds or less after the fiducial point.

22. The system of claim 19, wherein the at least one processor is configured to generate the output to apply the chest compression synchronized with the fiducial point comprising initiating the chest compression within 50 milliseconds or less before the fiducial point.

23. The system of claim 1, comprising initiating the chest compression, wherein the leading edge of the R-wave occurs prior to a peak of the R-wave.

24. The system of claim 1, comprising initiating the chest compression at the predetermined time relative to the detected QRS complex, the predetermined time being after detection of the leading edge of the R-wave of the QRS complex and before a peak of the R-wave.

25. The system of claim 1, wherein the at least one hemodynamic activity sensor comprises a sensor for use in at least one of: pulse oximetry, Doppler ultrasonography, plethysmography, phonocardiography, echocardiography, and transthoracic impedance.

26. The system of claim 1, wherein the at least one hemodynamic activity sensor comprises a radio frequency sensor.

27. The system of claim 1, wherein the at least one processor is configured to generate an output to cause the automated chest compressor to hold the chest compression at a target compression depth for a predetermined hold time period after the target compression depth is reached.

28. The system of claim 27, wherein the target compression depth is a maximum compression depth.

29. The system of claim 28, wherein the predetermined hold time period comprises at least a portion of a systole period.

30. The system of claim 29, wherein the predetermined hold time period comprises no portion of a diastole period.

31. The system of claim 27, wherein the predetermined hold time period is 125 milliseconds.

32. The system of claim 1, wherein the slope is of the leading edge of the R-wave of the QRS complex.

33. The system of claim 1, wherein the detection of the R-wave comprises performing a differentiation to obtain information about the slope over time.

34. The system of claim 33, wherein the detection of the R-wave comprises using the obtained information about the slope over time in identifying a peak of the R-wave.

35. The system of claim 1, wherein the detection of the R-wave comprises performing an integration to obtain information about the slope and a width of the QRS complex.

36. The system of claim 35, wherein the detection of the R-wave comprises using the obtained information about the slope and the width of the QRS complex in identifying a peak of the R-wave.

37. The system of claim 1, wherein the at least one processor is configured to:
   determine a fiducial point in the QRS complex, wherein the fiducial point occurs at a point in the QRS complex preceding a peak of the R-wave of the QRS complex; and
   generate the output to apply the chest compression synchronized with the fiducial point.

38. The system of claim 37, wherein the fiducial point occurs at the point in the QRS complex, wherein the point in the QRS complex is in the leading edge of the R-wave of the QRS complex.

39. The system of claim 37, wherein the at least one processor is configured to generate the output to apply the chest compression synchronized with the fiducial point, comprising initiating the chest compression within a range from approximately 125 milliseconds before the fiducial point to approximately 150 milliseconds after the fiducial point.

40. The system of claim 1, wherein detecting the R-wave of the QRS complex comprises using a threshold decay rate of the ECG waveform in filtering out noise.

41. The system of claim 40, wherein the detecting the R-wave of the QRS complex comprises detecting whether an R-wave detection threshold has been exceeded, wherein detecting whether the R-wave detection threshold has been exceeded comprises using the threshold decay rate of the ECG waveform.

42. The system of claim 1, wherein the estimated refractory period is based on the patient's heart rate.

43. The system of claim 1, wherein the estimated refractory period is between 10-200 milliseconds.

44. The system of claim 1, wherein the at least one processor is further configured to determine a heart rate of the patient based on the analyzed ECG signals.

* * * * *